US012023376B1

(12) United States Patent
Korber et al.

(10) Patent No.: US 12,023,376 B1
(45) Date of Patent: Jul. 2, 2024

(54) CONSERVED REGION T CELL VACCINES FOR CORONAVIRUS AND METHODS OF USE

(71) Applicants: Triad National Security, LLC, Los Alamos, NM (US); The Trustees of The University of Pennsylvania, Philadelphia, PA (US); Beth Israel Deaconess Medical Center, Inc., Boston, MA (US); Oxford University Innovation Limited, Oxford (GB)

(72) Inventors: Bette T. M. Korber, Los Alamos, NM (US); James Theiler, Los Alamos, NM (US); Dan Barouch, Boston, MA (US); Drew Weissman, Philadelphia, PA (US); Tomas Hanke, Oxford (GB)

(73) Assignees: Triad National Security, LLC, Los Alamos, NM (US); Oxford University Innovation Limited, Oxford (GB); The Trustees of the University of Pennsylvania, Philadelphia, PA (US); Beth Israel Deconess Medical Center, Inc., Boston, MA (US)

(*) Notice: Subject to any disclaimer, the term of this patent is extended or adjusted under 35 U.S.C. 154(b) by 220 days.

(21) Appl. No.: 17/234,590

(22) Filed: Apr. 19, 2021

Related U.S. Application Data

(60) Provisional application No. 63/011,816, filed on Apr. 17, 2020.

(51) Int. Cl.

| | |
|---|---|
| ***A61K 39/215*** | (2006.01) |
| ***A61K 9/51*** | (2006.01) |
| ***A61K 48/00*** | (2006.01) |
| ***A61P 31/14*** | (2006.01) |
| ***C07K 14/005*** | (2006.01) |
| ***C12N 7/00*** | (2006.01) |
| ***C12N 9/12*** | (2006.01) |
| ***C12N 9/14*** | (2006.01) |
| ***C12N 15/86*** | (2006.01) |
| *A61K 39/00* | (2006.01) |

(52) U.S. Cl.
CPC .......... *A61K 39/215* (2013.01); *A61K 9/5123* (2013.01); *A61P 31/14* (2018.01); *C07K 14/005* (2013.01); *C12N 7/00* (2013.01); *C12N 9/127* (2013.01); *C12N 9/14* (2013.01); *C12N 15/86* (2013.01); *C12Y 207/07048* (2013.01); *C12Y 306/04013* (2013.01); *A61K 2039/5254* (2013.01); *A61K 2039/53* (2013.01); *A61K 48/00* (2013.01); *C12N 2750/14143* (2013.01); *C12N 2770/18022* (2013.01); *C12N 2770/18034* (2013.01)

(58) Field of Classification Search
None
See application file for complete search history.

(56) References Cited

U.S. PATENT DOCUMENTS

| | | | |
|---|---|---|---|
| 9,670,152 | B2 | 6/2017 | Payne et al. |
| 10,221,127 | B2 | 3/2019 | Du et al. |
| 2019/0175716 | A1 | 6/2019 | Gilbert et al. |
| 2020/0155691 | A1 | 5/2020 | Derosa et al. |

FOREIGN PATENT DOCUMENTS

| | | |
|---|---|---|
| WO | WO 2017/075531 | 5/2017 |
| WO | WO 2020/214946 | 10/2020 |
| WO | WO 2020/219941 | 10/2020 |

OTHER PUBLICATIONS

Moghimi SM. Allergic Reactions and Anaphylaxis to LNP-Based COVID-19 Vaccines. Mol Ther. Mar. 3, 2021;29(3):898-900. doi: 10.1016/j.ymthe.2021.01.030. Epub Feb. 5, 2021. PMID: 33571463; PMCID: PMC7862013. (Year: 2021).*

GenBank accession NC_045512.2 (Mar. 30, 2020) (Year: 2020).*

Gao W, Tamin A, Soloff A, D'Aiuto L, Nwanegbo E, Robbins PD, Bellini WJ, Barratt-Boyes S, Gambotto A. Effects of a SARS-associated coronavirus vaccine in monkeys. Lancet. Dec. 6, 2003;362(9399):1895-6. doi: 10.1016/S0140-6736(03)14962-8. PMID: 14667748; PMCID: PMC7112457. (Year: 2003).*

Teigler JE, Iampietro MJ, Barouch DH. Vaccination with adenovirus serotypes 35, 26, and 48 elicits higher levels of innate cytokine responses than adenovirus serotype 5 in rhesus monkeys. J Virol. Sep. 2012;86(18):9590-8. doi: 10.1128/JVI.00740-12. Epub Jul. 11, 2012. PMID: 22787208; PMCID: PMC3446581. (Year: 2012).*

Dicks et al., "A Novel Chimpanzee Adenovirus Vector with Low Human Seroprevalence: Improved Systems for Vector Derivation and Comparative Immunogenicity," *PloS One*, 7(7):e40385, 2012 (12 pages).

Hassett et al., "Optimization of Lipid Nanoparticles for Intramuscular Administration of mRNA Vaccines," *Molecular Therapy: Nucleic Acids*, vol. 15, doi.org/10.1016/j.omtn.2019.01.013, 2019 (11 pages).

Li et al., "Emergence of SARS-COV-2 through recombination and strong purifying selection," *Sci. Adv.*, 6:eabb9153, 2020 (11 pages).

Ondondo et al., "Novel Conserved-region T-cell Mosaic Vaccine With High Global HIV-1 Coverage Is Recognized by Protective Responses in Untreated Infection," *Molecular Therapy*, vol. 24, No. 4, pp. 832-842, 2016.

Pardi et al., "Characterization of HIV-1 Nucleoside-Modified mRNA Vaccines in Rabbits and Rhesus Macaques," *Molecular Therapy: Nucleic Acids*, vol. 15, pp. 36-47, 2019.

(Continued)

*Primary Examiner* — Benjamin P Blumel
*Assistant Examiner* — Jeffrey Mark Sifford
(74) *Attorney, Agent, or Firm* — Klarquist Sparkman, LLP

(57) ABSTRACT

Immunogenic compositions and methods of their use in eliciting immune responses to coronaviruses, such as SARS-CoV-2 are provided.

15 Claims, 25 Drawing Sheets

Specification includes a Sequence Listing.

(56) References Cited

OTHER PUBLICATIONS

Pardi et al., "Nucleoside-modified mRNA immunization elicits influenza virus hemagglutinin stalk-specific antibodies," *Nature Communications*, 9:3361, 2018 (12 pages).
Theiler and Korber, "Graph-based optimization of epitope coverage for vaccine antigen design," *Statistics in Medicine*, vol. 37, pp. 181-194, 2018.
Theiler et al., "Epigraph: A Vaccine Design Tool Applied to an HIV Therapeutic Vaccine and a Pan-Filovirus Vaccine," *Scientific Reports*, 6:33987, 2016 (15 pages).

* cited by examiner

FIG. 8E
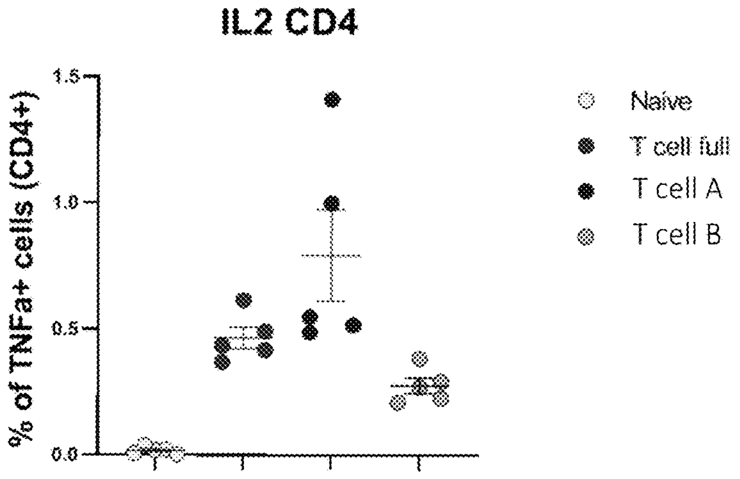
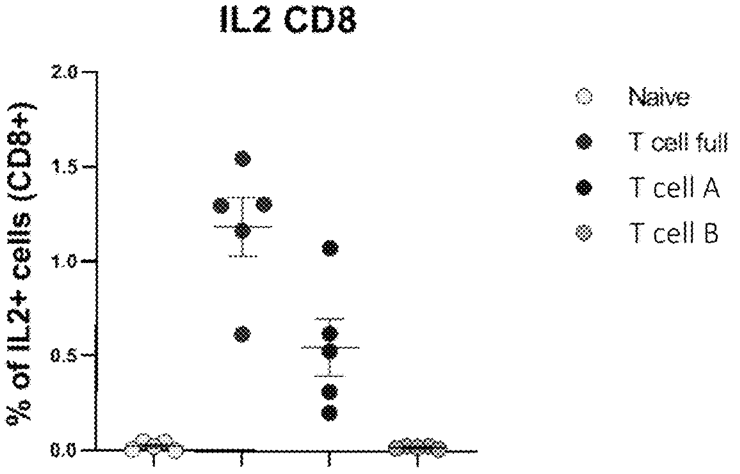
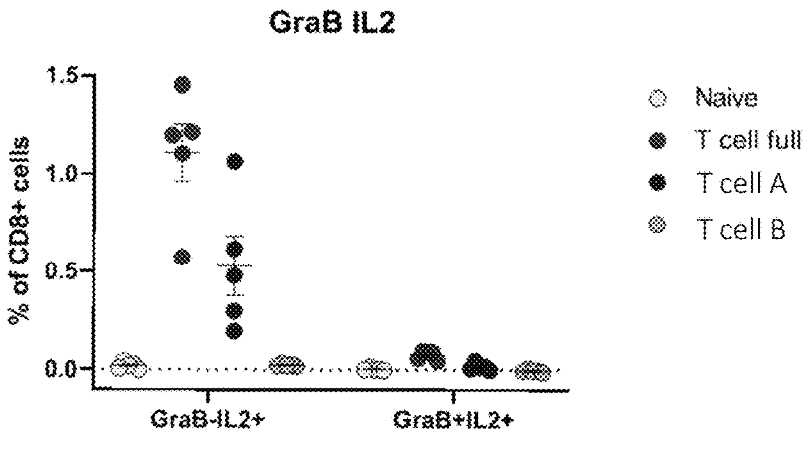

FIG. 11

```
      NC_045512 NCLDDRCILHCANFNVLFSTVFPPTSFGPLVRKIFVDGVPFVVSTGYHFRELGVVHNQDV  60
Region-1-EG-2.1 --S--------S-----------L---------M--------I-----------L-----
Region-1-EG-2.2 -------V---------------F----------C-----------H--------Y----

      NC_045512 NLHSSRLSFKELLVYAADPAMHAASGNLLLDKRTTCFSVAALTNNVAFQTVKPGNFNKDF  120
Region-1-EG-2.1 ---------N------------T-----------M----------------R--------
Region-1-EG-2.2 ----F--------L--------V--------R-------------F--------------

      NC_045512 YDFAVSKGFFKEGSSVELKHFFFAQDGNAAISDYDYYRYNLPTMCDIRQLLFVVEVVDKY  180
Region-1-EG-2.1 ---V----------F--------------V-------------I--------------N-
Region-1-EG-2.2 ----L---------P--------V----------E---------F--------F------

      NC_045512 FDCYDGGCINANQVIVNNLDKSAGFPFNKWGKARLYYDSMSYEDQDALFAYTKRNVIPTI  240
Region-1-EG-2.1 -----------S----------------------F--------------V----------
Region-1-EG-2.2 --------------T----------------------E--------V---------T---

      NC_045512 TQMNLKYAISAKNRARTVAGVSICSTMTNRQFHQKLLKSIAATRGATVVIGTSKFYGGWH  300
Region-1-EG-2.1 --------------S--------F--------Y--------S---------I--------
Region-1-EG-2.2 ----------V---------------I----------------G----------------

      NC_045512 NMLKTVYSDVENPHLMGWDYPKCDRAMPNMLRIMASLVLARKHTTCCSLSHRFYRLANEC  360
Region-1-EG-2.1 -----I--------F--------------I--------F--------I--------S---
Region-1-EG-2.2 -I-----------Y-------------------V----------M-----------T---

      NC_045512 AQVLSEMVMCGGSLYVKPGGTSSGDATTAYANSVFNICQAVTANVNALLSTDGNKIADKY  420
Region-1-EG-2.1 ------I-----------------E--------------S--------------------
Region-1-EG-2.2 --------I----------------------------F--------T-----------N-

      NC_045512 VRNLQHRLYECLYRNRDVDTDFVNEFYAYLRKHFSMMILSDDAVVCFNSTYASQGLVASI  480
Region-1-EG-2.1 I--------A---------I---------------I----------V---------L---
Region-1-EG-2.2 ---------G--------Y--------T--------I--------------V--------

      NC_045512 KNFKSVLYYQNNVFMSEAKCWTETDLTKGPHEFCSQHTMLVKQGDDYVVLPYPDPSRILG  540
Region-1-EG-2.1 ------------I----------I------------------H-------S---------
Region-1-EG-2.2 R----------------V--------I-----------I----------F----------

      NC_045512 AGCFVDDIVKTDGTLMIERFVSLAIDAYPLTKHPNQEYADVFHLYLQYIRKLHDELTGHM  600
Region-1-EG-2.1 --------L---------------------I-----------R----------Y------
Region-1-EG-2.2 -------V--------V------------F---------Y---------K---------I

      NC_045512 LDMYSVMLTNDNTSRYWEPEFYEAMYTPHTVLQAVGACVLCNSQTSLRCGACIRRPFLCC  660
Region-1-EG-2.1 --I----------L--------D-------------V-------------V---------
Region-1-EG-2.2 --------I---------S--------S--------S--------L--------K-----

      NC_045512 KCCYDHVISTSHKLVLSVNPYVCNAFGCDVTDVTQLYLGGMSYYCKSHKPPISFPLCANG  720
Region-1-EG-2.1 E---------L--------------L---------------N--------S---------
Region-1-EG-2.2 ------I--------F--------V-----------C---------P----------V--

      NC_045512 QVFGLYKNTCVGSDNVTDFNAIATCDWTNAGDYILANTCTERLKLFAAETLKATEETFKL  780
Region-1-EG-2.1 H---------F----------------I-----------I-------------I------
Region-1-EG-2.2 ----------A-----------S--------------A-----------M----------

      NC_045512 SYGIATVREVLSDRELHLSWEVGKPRPPLNRNYVFTGYRVTKNSKVQIGEYTFEKGDYGD  840
Region-1-EG-2.1 -----I----------Y-----------F----------L---------D--------V-
Region-1-EG-2.2 ---V---------K---------R--------------H--------T--------Y---

      NC_045512 AVVYRGTTTYKLNVGDYFVLTSHTVMPLSAPTLVPQEHYVRITGLYPTLNISDEFSSNVA  900
Region-1-EG-2.1 ----------R--------------I----------D----------------D------
Region-1-EG-2.2 ------I-----------L------------I----------I---------Y-------
```

FIG. 11 (cont.)

```
     NC_045512 NYQKVGMQKYSTLQGPPGTGKSHFAIGLALYYPSARIVYTACSHAAVDALCEKALKYLPI  960
Region-1-EG-2.1 ------I---------------Y---------L--------------YT--------F--
Region-1-EG-2.2 --------R-------------------S--------M-------------D--------

     NC_045512 DKCSRIIPARARVECFDKFKVNSTLEQYVFCTVNALPETTADIVVFDEISMATNYDLSVV  1020
Region-1-EG-2.1 -------------D--------L--------------D-------------T--------
Region-1-EG-2.2 -----------L--------L-------------------V----------T--------

     NC_045512 NARLRAKHYVYIGDPAQLPAPRTLLTKGTLEPEYFNSVCRLMKTIGPDMFLGTCRRCPAE  1080
Region-1-EG-2.1 ----C---------S----------I--------------F-----------------S-
Region-1-EG-2.2 -V---------V----------------I------------I---------R--------

     NC_045512 IVDTVSALVYDNKL  1094
Region-1-EG-2.1 ------------R-
Region-1-EG-2.2 ----L---------
```

FIG. 13

```
             NC_045512 NCLDDRCILHCANFNVLFSTVFPPTSFGPLVRKIFVDGVPFVVSTGYHFRELGVVHNQDV  60
SARBECO-CoV-2-EG-3.1 -----------------------L------------------------------------
SARBECO-CoV-2-EG-3.2 ------------------------------------------------------------

             NC_045512 NLHSSRLSFKELLVYAADPAMHAASGNLLLDKRTTCFSVAALTNNVAFQTVKPGNFNKDF  120
SARBECO-CoV-2-EG-3.1 -I--------------------------------------------S-------------
SARBECO-CoV-2-EG-3.2 -I------------------------------------------S---------------

             NC_045512 YDFAVSKGFFKEGSSVELKHFFFAQDGNAAISDYDYYRYNLPTMCDIRQLLFVVEVVDKY  180
SARBECO-CoV-2-EG-3.1 ------------------------------------------------------------
SARBECO-CoV-2-EG-3.2 ------------------------------------------------------------

             NC_045512 FDCYDGGCINANQVIVNNLDKSAGFPFNKWGKARLYYDSMSYEDQDALFAYTKRNVIPTI  240
SARBECO-CoV-2-EG-3.1 --------------------------------------------------------L---
SARBECO-CoV-2-EG-3.2 --------------------------------------------------------L---

             NC_045512 TQMNLKYAISAKNRARTVAGVSICSTMTNRQFHQKLLKSIAATRGATVVIGTSKFYGGWH  300
SARBECO-CoV-2-EG-3.1 -----------------------------------------------------------N
SARBECO-CoV-2-EG-3.2 -----------------------------------------------------------N

             NC_045512 NMLKTVYSDVENPHLMGWDYPKCDRAMPNMLRIMASLVLARKHTTCCSLSHRFYRLANEC  360
SARBECO-CoV-2-EG-3.1 -----------T-------------------------------S---N------------
SARBECO-CoV-2-EG-3.2 -----------S-------------------------------N---N------------

             NC_045512 AQVLSEMVMCGGSLYVKPGGTSSGDATTAYANSVFNICQAVTANVNALLSTDGNKIADKY  420
SARBECO-CoV-2-EG-3.1 --------------------------------------------------------G---
SARBECO-CoV-2-EG-3.2 ------------------------------------------------------------

             NC_045512 VRNLQHRLYECLYRNRDVDTDFVNEFYAYLRKHFSMMILSAAAVVCFNSTYASQGLVASI  480
SARBECO-CoV-2-EG-3.1 I------------------HE--D----------------------Y--N--A-------
SARBECO-CoV-2-EG-3.2 ----------------------------------------------Y--N--A-------

             NC_045512 KNFKSVLYYQNNVFMSEAKCWTETDLTKGPHEFCSQHTMLVKQGDDYVYLPYPDPSRILG  540
SARBECO-CoV-2-EG-3.1 ----A----------------------R--------------------------------
SARBECO-CoV-2-EG-3.2 ---------------------------R--------------------------------

             NC_045512 AGCFVDDIVKTDGTLMIERFVSLAIDAYPLTKHPNQEYADVFHLYLQYIRKLHDELTGHM  600
SARBECO-CoV-2-EG-3.1 ------------------------------------------------------------
SARBECO-CoV-2-EG-3.2 ------------------------------------------------------------

             NC_045512 LDMYSVMLTNDNTSRYWEPEFYEAMYTPHTVLQAVGACVLCNSQTSLRCGACIRRPFLCC  660
SARBECO-CoV-2-EG-3.1 -----------S------------------I-----------------------------
SARBECO-CoV-2-EG-3.2 ------------------------------------------------------------

             NC_045512 KCCYDHVISTSHKLVLSVNPYVCNAPGCDVTDVTQLYLGGMSYYCKSHKPPISFPLCANG  720
SARBECO-CoV-2-EG-3.1 -------------------------T--------------------A-------------
SARBECO-CoV-2-EG-3.2 ----------------------------------------------L-------------

             NC_045512 QVFGLYKNTCVGSDNVTDFNAIATCDWTNAGDYILANTCTERLKLFAAETLKATEETFKL  780
SARBECO-CoV-2-EG-3.1 ------------------------------------------------------------
SARBECO-CoV-2-EG-3.2 ------------------------------------------------------------
```

FIG. 13 (cont.)

```
         NC_045512 SYGIATVREVLSDRELHLSWEVGKPRPPLNRNYVFTGYRVTKNSKVQIGEYTFEKGDYGD  840
SARBECO-CoV-2-EG-3.1 ----------------Y----------------------------T--------------
SARBECO-CoV-2-EG-3.2 ------------------------------------------------------------

         NC_045512 AVVYRGTTTYKLNVGDYFVLTSHTVMPLSAPTLVPQEHYVRITGLYPTLNISDEFSSNVA  900
SARBECO-CoV-2-EG-3.1 ----------------------------------------------------E-------
SARBECO-CoV-2-EG-3.2 ------------------------------------------------------------

         NC_045512 NYQKVGMQKYSTLQGPPGTGKSHFAIGLALYYPSARIVYTACSHAAVDALCEKALKYLPI  960
SARBECO-CoV-2-EG-3.1 ----I-------------------------------------------------------
SARBECO-CoV-2-EG-3.2 ----I-------------------------------------------------------

         NC_045512 DKCSRIIPARARVECFDKFKVNSTLEQYVFCTVNALPETTADIVVFDEISMATNYDLSVV  1020
SARBECO-CoV-2-EG-3.1 ------------------------------------------------------------
SARBECO-CoV-2-EG-3.2 ------------------------------------------------------------

         NC_045512 NARLRAKHYVYIGDPAQLPAPRTLLTKGTLEPEYFNSVCRLMKTIGPDMFLGTCRRCPAE  1080
SARBECO-CoV-2-EG-3.1 ------------------------------------------------------------
SARBECO-CoV-2-EG-3.2 ------------------------------------------------------------

         NC_045512 IVDTVSALVYDNKL  1094
SARBECO-CoV-2-EG-3.1 --------------
SARBECO-CoV-2-EG-3.2 --------------
```

FIG. 15

```
      NC_045512 GGKPCIKVATVQSKMSDVKCTSVVLLSVLQQLRVESSSKLWAQCVQLHNDILLAKDTTEA  60
Region-2-EG-2.1 -----V--------I-----------L---------L--------------I--------
Region-2-EG-2.2 --------------T-------------F--------F----------------R-----

      NC_045512 FEKMVSLLSVLLSMQGAVDINKLCEEMLDNRATLQAIASEFSSLPSYAAFATAQEAYEQA  120
Region-2-EG-2.1 -G-------------R----------I--------S--------S-------------R-
Region-2-EG-2.2 -----------F----------F---------I----------------L----------

      NC_045512 VANGDSEVVLKKLKKSLNVAKSEFDRDAAMQRKLEKMADQAMTQMYKQARSEDKRAKVTS  180
Region-2-EG-2.1 --------F----------------C---------N------------V-----------
Region-2-EG-2.2 -V---------N-------------L-----------S-----------K--------I-

      NC_045512 AMQTMLFTMLRKLDNDALNNIINNARDGCVPLNIIPLTTAAKLMVVIPDYNTYKNTCDGT  240
Region-2-EG-2.1 ---I--------F--------V--------------F----------S-----------I
Region-2-EG-2.2 ---------F------------D--------------I--------T--------M----

      NC_045512 TFTYASALWEIQQVVDADSKIVQLSEISMDNSPNLAWPLIVTALRANSAVKLQNNELSPV  300
Region-2-EG-2.1 ------------H----------F--------S--------I------------------
Region-2-EG-2.2 --I------------N----------V------------V---------I---------I

      NC_045512 ALRQMSCAAGTTQTACTDDNALAYYNTTKGGRFVLALLSDLQDLKWARFPKSDGTGTIYT  360
Region-2-EG-2.1 V---------------I----------I-----------N-----------------V--
Region-2-EG-2.2 -----------I----------V-----------F--------------S---------I

      NC_045512 ELEPPCRFVTDTPKGPKVKYLYFIKGLNNLNRGMVLGSLAATVRLQAGNATEVPANSTVL  420
Region-2-EG-2.1 ------G--------L--------R--------I--------------K--------I--
Region-2-EG-2.2 ------------L------------R---------------I--------I---------

      NC_045512 SFCAFAVDAAKAYKDYLASGGQPITNCVKMLCTHTGTGQAITVTPEANMDQESFGGASCC  480
Region-2-EG-2.1 ------I----------V----------------I--------I----------------
Region-2-EG-2.2 F--------S--------------I-----------I------------E----------

      NC_045512 LYCRCHIDHPNPKGFCDLKGKYVQIPTTCANDPVGFTLKNTVCTVCGMWKGYGCSCDQLR  540
Region-2-EG-2.1 M---------D----------------I--------I---------S------------C
Region-2-EG-2.2 ---------S----------R--------V--------------I---------G-----
```

FIG. 16

```
NC_045512 GGKPCIKVATVQSKMSDVKCTSVVLLSVLQQLRVESSSKLWAQCVQLHNDILLAKDTTEA  60
     EG-1 ------------------------------------------------------------
     EG-2 ------------------------------------------------------------

NC_045512 FEKMVSLLSVLLSMQGAVDINKLCEEMLDNRATLQAIASEFSSLPSYAAFATAQEAYEQA  120
     EG-1 ---------------------R---------------------------Y----------
     EG-2 ---------------------R--------------------------------------

NC_045512 VANGDSEVVLKKLKKSLNVAKSEFDRDAAMQRKLEKMADQAMTQMYKQARSEDKRAKVTS  180
     EG-1 -S-----------------------H----------------------------------
     EG-2 ------------------------------------------------------------

NC_045512 AMQTMLFTMLRKLDNDALNNIINNARDGCVPLNIIPLTTAAKLMVVIPDYNTYKNTCDGT  240
     EG-1 ----------------------------------------------V---G--------N
     EG-2 ----------------------------------------------V----------E-S

NC_045512 TFTYASALWEIQQVVDADSKIVQLSEISMDNSPNLAWPLIVTALRANSAVKLQNNELSPV  300
     EG-1 ---------------------------N--------------------------------
     EG-2 ----------------------P----N----Q---------------------------

NC_045512 ALRQMSCAAGTTQTACTDDNALAYYNTTKGGRFVLALLSDLQDLKWARFPKSDGTGTIYT  360
     EG-1 ----------------NE--------NS------------H-------------------
     EG-2 ---------------------------S--------------------------------

NC_045512 ELEPPCRFVTDTPKGPKVKYLYFIKGLNNLNRGMVLGSLAATVRLQAGNATEVPANSTVL  420
     EG-1 ------------------------------------------------------------
     EG-2 ------------------------------------------------------------

NC_045512 SFCAFAVDAAKAYKDYLASGGQPITNCVKMLCTHTGTGQAITVTPEANMDQESFGGASCC  480
     EG-1 --------P--------S------------------------------------------
     EG-2 ---------S---R----------------------------------------------

NC_045512 LYCRCHIDHPNPKGFCDLKGKYVQIPTTCANDPVGFTLKNTVCTVCGMWKGYGCSCDQLR  540
     EG-1 --------------Y-E---------------------R---------------------
     EG-2 --------------------------------------R---------------------
```

CONSERVED REGION T CELL VACCINES FOR CORONAVIRUS AND METHODS OF USE

CROSS REFERENCE TO RELATED APPLICATIONS

This application claims the benefit of U.S. Provisional Application No. 63/011,816, filed Apr. 17, 2020, which is incorporated herein by reference in its entirety.

ACKNOWLEDGMENT OF GOVERNMENT SUPPORT

This invention was made with government support under Contract No. 89233218CNA000001 awarded by the U.S. Department of Energy/National Nuclear Security Administration. The government has certain rights in the invention.

FIELD

This disclosure relates to conserved region T cell vaccines for coronaviruses, particularly SARS-CoV-2, and methods of use.

BACKGROUND

COVID-19 is a severe respiratory disease first reported in China in late December 2019. Severe acute respiratory syndrome coronavirus 2 (SARS-CoV-2) is the etiological agent of COVID-19, and is a new member of the diverse genus *Betacoronavirus*. It rapidly became epidemic in China, spread globally, and has had an unparalleled and devastating impact on humanity. Three factors combine to make this disease so dangerous: human beings have no immunological experience with this virus, leaving us vulnerable to infection; it is highly transmissible (estimates for Ro range between 2-5); and it has a high mortality rate (estimates range between 0.5-5%).

SUMMARY

Provided herein are immunogenic compositions and methods of their use in eliciting immune responses to coronaviruses, such as SARS-CoV-2.

Methods of eliciting an immune response to a coronavirus in a subject are provided. In some embodiments, the methods include administering to the subject a composition comprising one or more polypeptides with at least 95% sequence identity (such as at least 99% sequence identity) to any one of SEQ ID NOs: 1-14 and 18 or a composition comprising one or more nucleic acids encoding one or more polypeptides with at least 95% sequence identity (such as at least 99% sequence identity) to any one of SEQ ID NOs: 1-14 and 18, thereby eliciting an immune response to the coronavirus. In some examples, the one or more polypeptides include or consist of the amino acid sequence of any one of SEQ ID NOs: 1-14 and 18.

In some embodiments, the methods include administering to the subject one or more (such as 1, 2, 3, or more) of the polypeptides, or one or more nucleic acids (such as 1, 2, 3, or more) nucleic acids encoding the polypeptides. In particular examples, the methods include administering to the subject the following polypeptides (or nucleic acids encoding the following polypeptides): SEQ ID NO: 5 and SEQ ID NO: 6; or SEQ ID NO: 5, SEQ ID NO: 6, and SEQ ID NO: 7; or SEQ ID NO: 5 and SEQ ID NO: 8; or SEQ ID NO: 5, SEQ ID NO: 8, and SEQ ID NO: 9; or SEQ ID NO: 10; or SEQ ID NO: 10 and SEQ ID NO: 11; or SEQ ID NO: 10, SEQ ID NO: 11, and SEQ ID NO: 12; or SEQ ID NO: 10 and SEQ ID NO: 13; or SEQ ID NO: 10, SEQ ID NO: 13, and SEQ ID NO: 14.

In particular embodiments, the nucleic acid encoding the one or more polypeptides is mRNA, which in some embodiments is formulated in a lipid nanoparticle. In some non-limiting examples, the lipid nanoparticle is ALC-0315. In other embodiments, the nucleic acid is included in an adenovirus vector administered to the subject. In some examples, the adenovirus vector is an Ad5, Ad26, Ad35, or Ad52 adenovirus vector or a ChAdO×1 or ChAdO×2 adenovirus vector.

Also provided are immunogenic compositions including one or more polypeptides with at least 95% sequence identity (such as at least 99% sequence identity) to any one of SEQ ID NOs: 1-14 and 18 or a nucleic acid encoding a polypeptide with at least 95% sequence identity (such as at least 99% sequence identity) to any one of SEQ ID NOs: 1-14 and 18; and a pharmaceutically acceptable carrier. In some examples, the one or more polypeptides include or consist of the amino acid sequence of any one of SEQ ID NOs: 1-14 and 18.

In some embodiments, the composition includes one or more (such as 1, 2, 3, or more) of the polypeptides, or one or more nucleic acids (such as 1, 2, 3, or more) nucleic acids encoding the polypeptides. In particular examples, the composition includes the following polypeptides (or nucleic acids encoding the following polypeptides): SEQ ID NO: 5 and SEQ ID NO: 6; or SEQ ID NO: 5, SEQ ID NO: 6, and SEQ ID NO: 7; or SEQ ID NO: 5 and SEQ ID NO: 8; or SEQ ID NO: 5, SEQ ID NO: 8, and SEQ ID NO: 9; or SEQ ID NO: 10; or SEQ ID NO: 10 and SEQ ID NO: 11; or SEQ ID NO: 10, SEQ ID NO: 11, and SEQ ID NO: 12; or SEQ ID NO: 10 and SEQ ID NO: 13; or SEQ ID NO: 10, SEQ ID NO: 13, and SEQ ID NO: 14.

In particular embodiments, the composition includes one or more mRNA encoding the one or more polypeptides, which in some embodiments is formulated in a lipid nanoparticle. In some non-limiting examples, the lipid nanoparticle is ALC-0315. Also provided are methods of eliciting an immune response to a coronavirus in a subject, including administering the composition to the subject.

Also provided are vectors including nucleic acids encoding one or more polypeptides with at least 95% sequence identity (such as at least 99% sequence identity) to any one of SEQ ID NOs: 1-14 and 18. In some examples, the vector includes a nucleic acid encoding the amino acid sequence of any one of SEQ ID NOs: 1-14 and 18. In particular examples, the vector is an adenovirus vector, such as an Ad5, Ad26, Ad35, or Ad52 adenovirus vector or a ChAdO×1 or ChAdO×2 vector. Also provided are immunogenic compositions including a disclosed vector and a pharmaceutically acceptable carrier and methods of eliciting an immune response to a coronavirus in a subject, including administering the composition to the subject.

The foregoing and other features of the disclosure will become more apparent from the following detailed description, which proceeds with reference to the accompanying figures.

BRIEF DESCRIPTION OF THE DRAWINGS

FIGS. 8A-8F show T cell cytokine responses from Balb/c (FIGS. 8A-8C) and BL/6 (FIG. 8D-8F) immunized with mRNA-LNP vaccines as indicated. "T cell full" includes the nucleic acid of SEQ ID NO: 15; "T cell A" includes the nucleic acid of SEQ ID NO: 16; and "T cell B" includes the nucleic acid of SEQ ID NO: 17. Representative experiments are shown.

FIG. 11 is an alignment of SEQ ID NOs: 1 (NC_045512), 6 (Region-1-EG-2.1), and 7 (Region 1-EG-2.2)

FIG. 13 is an alignment of SEQ ID NOs: 1 (NC_045512), 8 (SARBECO-CoV-2-EG-3.1), and 9 (SARBECO-CoV-2-EG-3.2).

FIG. 15 is an alignment of SEQ ID NO: 10 (NC_045512), 11 (Region-2-EG-2.1), and 12 (Region-2-EG-2.2).

FIG. 16 is an alignment of SEQ ID NO: 10 (NC_045512), 13 (EG-1), and 14 (EG-2).

SEQUENCE LISTING

Figure 1:
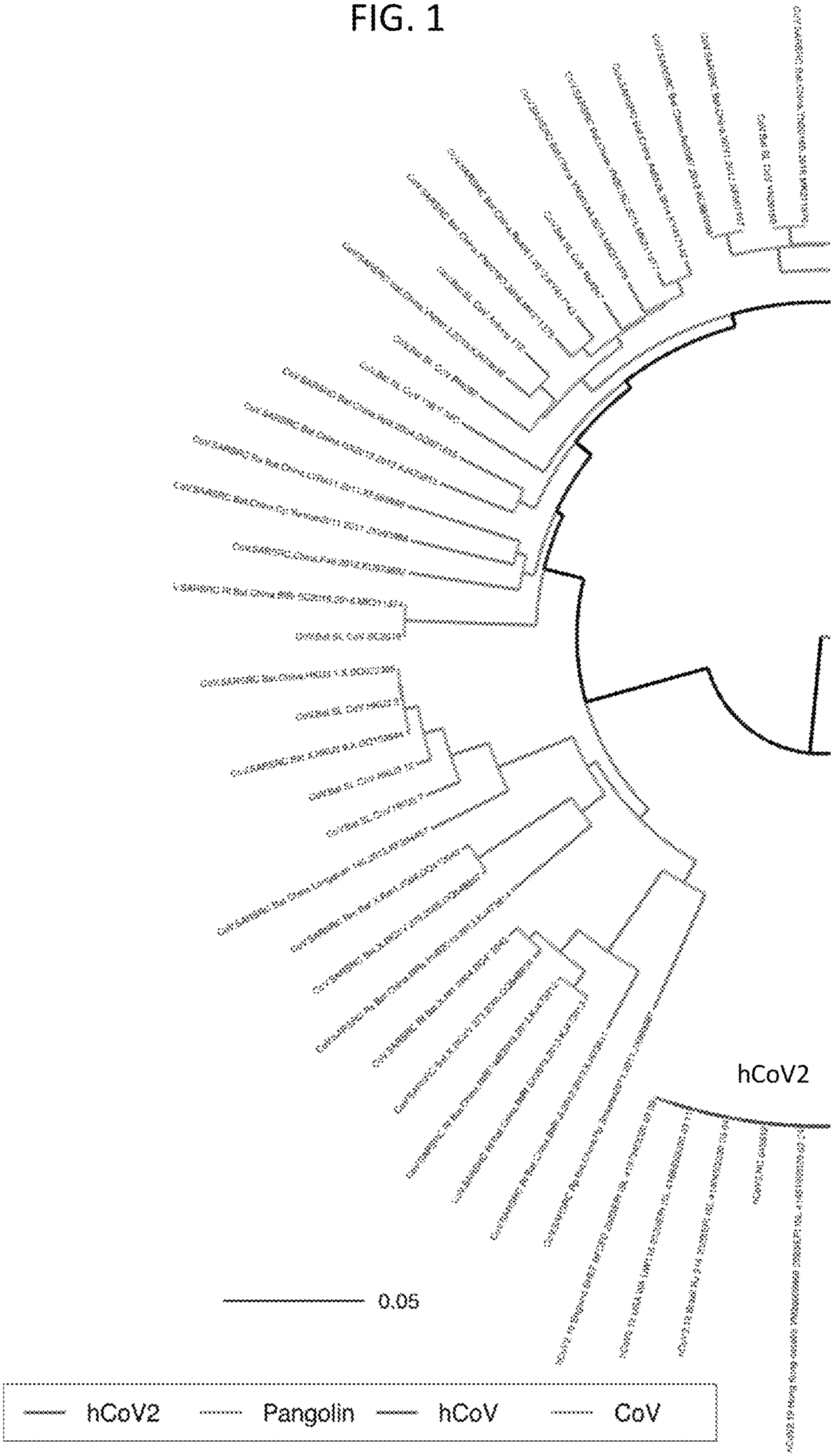
FIG. 1 is a tree illustrating the baseline Sarbecovirus alignment used to define conserved regions. The alignment includes 82 diverse Sarbecoviruses and a single MERS virus, including 49 diverse bat viruses, 14 SARS-CoV-2 pandemic sequences (representative of the sampling available in April 2020), 14 from the SARS-CoV-1 pandemic, and 5 pangolin viruses.
Figure 1:
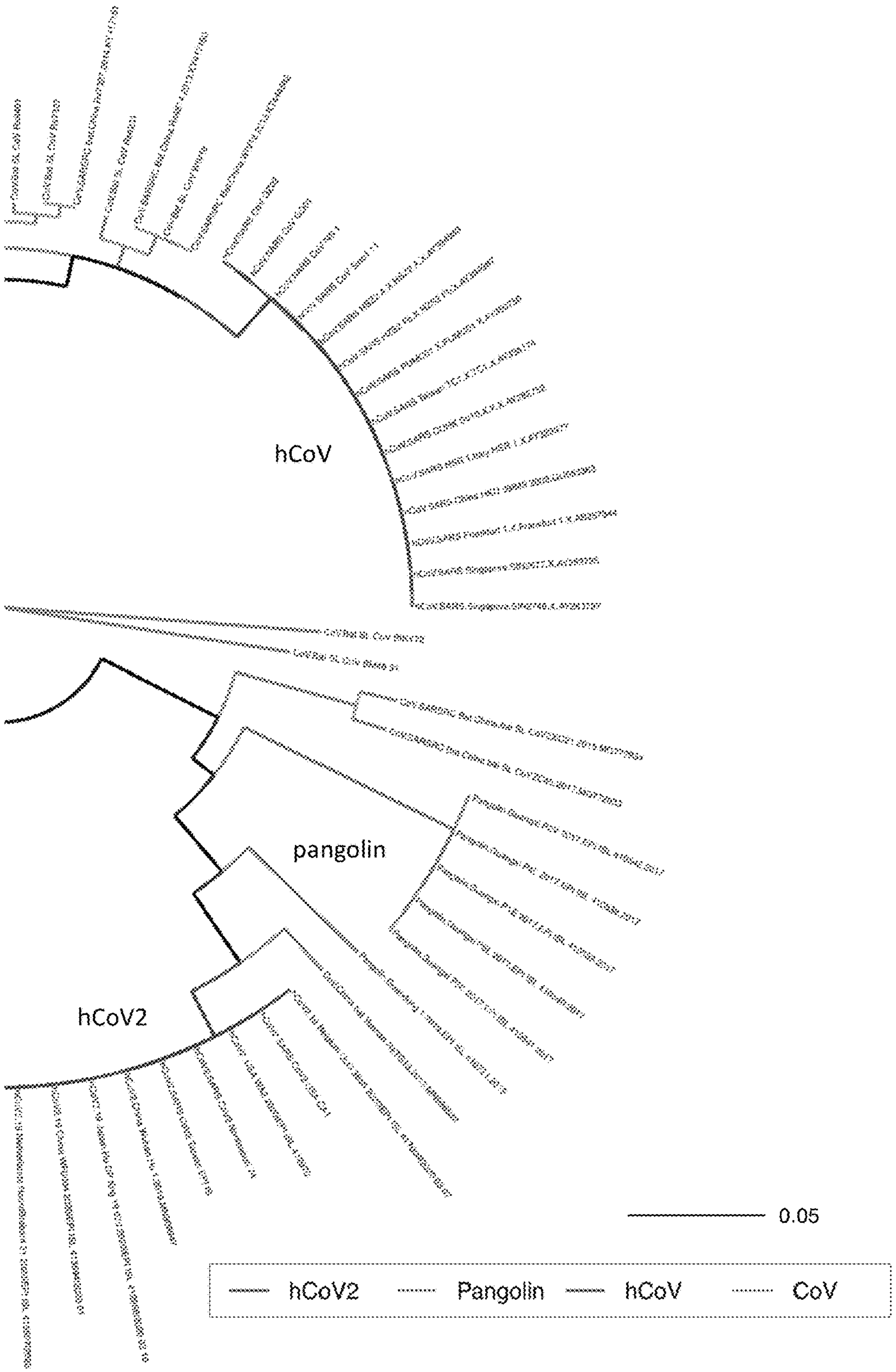

Any nucleic acid and amino acid sequences provided herein and in the accompanying Sequence Listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Apr. 19, 2021, and is 110,695 bytes, which is incorporated by reference herein.

```
SEQ ID NO: 1 is the amino acid sequence of an exemplary
conserved region SARS-COV-2 polypeptide spanning
RNA-dependent RNA polymerase helicase proteins.
NCLDDRCILHCANFNVLFSTVFPPTSFGPLVRKIFVDGVPFVVSTGYHFRELG

VVHNQDVNLHSSRLSFKELLVYAADPAMHAASGNLLLDKRTTCFSVAALTNNVAFQ

TVKPGNFNKDFYDFAVSKGFFKEGSSVELKHFFFAQDGNAAISDYDYYRYNLPTMC

DIRQLLFVVEVVDKYFDCYDGGCINANQVIVNNLDKSAGFPFNKWGKARLYYDSMS

YEDQDALFAYTKRNVIPTITQMNLKYAISAKNRARTVAGVSICSTMTNRQFHQKLL

KSIAATRGATVVIGTSKFYGGWHNMLKTVYSDVENPHLMGWDYPKCDRAMPNMLRI

MASLVLARKHTTCCSLSHRFYRLANECAQVLSEMVMCGGSLYVKPGGTSSGDATTA

YANSVFNICQAVTANVNALLSTDGNKIADKYVRNLQHRLYECLYRNRDVDTDFVNE

FYAYLRKHFSMMILSDDAVVCFNSTYASQGLVASIKNFKSVLYYQNNVEMSEAKCW

TETDLTKGPHEFCSQHTMLVKQGDDYVYLPYPDPSRILGAGCFVDDIVKTDGTLMI
```

-continued

ERFVSLAIDAYPLTKHPNQEYADVFHLYLQYIRKLHDELTGHMLDMYSVMLTNDNT

SRYWEPEFYEAMYTPHTVLQAVGACVLCNSQTSLRCGACIRRPFLCCKCCYDHVIS

TSHKLVLSVNPYVCNAPGCDVTDVTQLYLGGMSYYCKSHKPPISFPLCANGQVFGL

YKNTCVGSDNVTDFNAIATCDWTNAGDYILANTCTERLKLFAAETLKATEETFKLS

YGIATVREVLSDRELHLSWEVGKPRPPLNRNYVFTGYRVTKNSKVQIGEYTFEKGD

YGDAVVYRGTTTYKLNVGDYFVLTSHTVMPLSAPTLVPQEHYVRITGLYPTLNISD

EFSSNVANYQKVGMQKYSTLQGPPGTGKSHFAIGLALYYPSARIVYTACSHAAVDA

LCEKALKYLPIDKCSRIIPARARVECFDKFKVNSTLEQYVFCTVNALPETTADIVV

FDEISMATNYDLSVVNARLRAKHYVYIGDPAQLPAPRTLLTKGTLEPEYFNSVCRL

MKTIGPDMFLGTCRRCPAEIVDTVSALVYDNKL

SEQ ID NO: 2 is the amino acid sequence of an exemplary conserved region SARS-COV-2 polypeptide from RNA-dependent RNA polymerase.

FQTVKPGNFNKDFYDFAVSKGFFKEGSSVELKHFFFAQDGNAAISDYDYYRYN

LPTMCDIRQLLFVVEVVDKYFDCYDGGCINANQVIVNNLDKSAGFPFNKWGKARLY

YDSMSYEDQDALFAYTKRNVIPTITQMNLKYAISAKNRARTVAGVSICSTMTNRQF

HQKLLKSIAATRGATVVIGTSKFYGGWHNMLKTVYSDVE

SEQ ID NO: 3 is the amino acid sequence of an exemplary conserved region SARS-COV-2 polypeptide from helicase.

EFSSNVANYQKVGMQKYSTLQGPPGIGKSHFAIGLALYYPSARIVYTACSHAA

VDALCEKALKYLPIDKCSRIIPARARVECFDKFKVNSTLEQYVFCTVNALPETTAD

IVVFDEISMATNYDLSVVNARLRAKHYVYIGDPAQLPAPRTLLTKGTLEPEYFNSV

CRLMKTIGPDMFLGTCRRCPAEIVDTVSALVYDNKL

SEQ ID NO: 4 is the amino acid sequence of an exemplary conserved region SARS-COV-2 polypeptide spanning nsp6 through nsp10 proteins.

GGKPCIKVATVQSKMSDVKCTSVVLLSVLQQLRVESSSKLWAQCVQLHNDILL

AKDTTEAFEKMVSLVLLSMQGAVDINKLCEEMLDNRATLQAIASEFSSLPSYAAFA

TAQEAYEQAVANGDSEVVLKKLKKSLNVAKSEFDRDAAMORKLEKMADQAMTQMYK

QARSEDKRAKVTSAMQTMLFTMLRKLDNDALNNIINNARDGCVPLNIIPLTTAAKL

MVVIPDYNTYKNTCDGTTFTYASALWEIQQVVDADSKIVQLSEISMDNSPNLAWPL

IVTALRANSAVKLQNNELSPVALRQMSCAAGITQTACTDDNALAYYNTTKGGRFVL

ALLSDLQDLKWARFPKSDGTGTIYTELEPPCRFVTDTPKGPKVKYLYFIKGLNNLN

RGMVLGSLAATVRLQAGNATEVPANSTVLSFCAFAVDAAKAYKDYLASGGQPITNC

VKMLCTHTGTGQAITVTPEANMDQESFGGASCCLYCRCHIDHPNPKGFCDLKGKYV

QIPTTCANDPVGFTLKNTVCTVCGMWKGYGCSCDQLR

SEQ ID NO: 5 is the amino acid sequence of a modified conserved region SARS-COV-2 polypeptide spanning RNA-dependent RNA polymerase and helicase proteins (Region 1), including a polymerase inactivating mutation (SDD to SAA at amino acids 464-466).

NCLDDRCILHCANFNVLFSTVFPPTSFGPLVRKIFVDGVPFVVSTGYHFRELG

VVHNQDVNLHSSRLSFKELLVYAADPAMHAASGNLLLDKRTTCFSVAALTNNVAFQ

TVKPGNFNKDFYDFAVSKGFFKEGSSVELKHFFFAQDGNAAISDYDYYRYNLPTMC

DIRQLLFVVEVVDKYFDCYDGGCINANQVIVNNLDKSAGFPFNKWGKARLYYDSMS

YEDQDALFAYTKRNVIPTITQMNLKYAISAKNRARTVAGVSICSTMTNRQFHQKLL

KSIAATRGATVVIGTSKFYGGWHNMLKTVYSDVENPHLMGWDYPKCDRAMPNMLRI

-continued

MASLVLARKHTTCCSLSHRFYRLANECAQVLSEMVMCGGSLYVKPGGTSSGDATTA

YANSVFNICQAVTANVNALLSTDGNKIADKYVRNLQHRLYECLYRNRDVDTDFVNE

FYAYLRKHFSMMILSAAAVVCFNSTYASQGLVASIKNFKSVLYYQNNVEMSEAKCW

TETDLTKGPHEFCSQHTMLVKQGDDYVYLPYPDPSRILGAGCFVDDIVKTDGTLMI

ERFVSLAIDAYPLTKHPNQEYADVFHLYLQYIRKLHDELTGHMLDMYSVMLTNDNT

SRYWEPEFYEAMYTPHTVLQAVGACVLCNSQTSLRCGACIRRPFLCCKCCYDHVIS

TSHKLVLSVNPYVCNAPGCDVTDVTQLYLGGMSYYCKSHKPPISFPLCANGQVFGL

YKNTCVGSDNVTDFNAIATCDWTNAGDYILANTCTERLKLFAAETLKATEETFKLS

YGIATVREVLSDRELHLSWEVGKPRPPLNRNYVFTGYRVTKNSKVQIGEYTFEKGD

YGDAVVYRGTTTYKLNVGDYFVLTSHTVMPLSAPTLVPQEHYVRITGLYPTLNISD

EFSSNVANYQKVGMQKYSTLQGPPGTGKSHFAIGLALYYPSARIVYTACSHAAVDA

LCEKALKYLPIDKCSRIIPARARVECFDKFKVNSTLEQYVFCTVNALPETTADIVV

FDEISMATNYDLSVVNARLRAKHYVYIGDPAQLPAPRTLLTKGTLEPEYFNSVCRL

MKTIGPDMFLGTCRRCPAEIVDTVSALVYDNKL

SEQ ID NO: 6 is the amino acid sequence of a SARS-COV-2 Region 1 optimized polypeptide (Region 1 SARS-COV2-EG-2.1):

NCSDDRCILHCSNFNVLFSTVFPLTSFGPLVRKMFVDGVPFVISTGYHFRELG

VLHNQDVNLHSSRLSFNELLVYAADPAMHTASGNLLLDKRTMCFSVAALTNNVAFQ

TVRPGNFNKDFYDFVVSKGFFKEGSFVELKHFFFAQDGNAVISDYDYYRYNLPTIC

DIRQLLFVVEVVDNYFDCYDGGCINASQVIVNNLDKSAGFPFNKWGKARFYYDSMS

YEDQDALFVYTKRNVIPTITQMNLKYAISAKNRSRTVAGVSIFSTMTNRQFYQKLL

KSIASTRGATVVIGISKFYGGWHNMLKTIYSDVENPHFMGWDYPKCDRAMPNILRI

MASLVFARKHITCCILSHRFYRLSNECAQVLSEIVMCGGSLYVKPGGTSSGEATTA

YANSVFNICQSVTANVNALLSTDGNKIADKYIRNLQHRLYACLYRNRDVDIDFVNE

FYAYLRKHFSIMILSAAAVVCVNSTYASQGLLASIKNFKSVLYYQNNIFMSEAKCW

TEIDLTKGPHEFCSQHTMLVKHGDDYVYLSYPDPSRILGAGCFVDDILKTDGTLMI

ERFVSLAIDAYPLIKHPNQEYADVERLYLQYIRKLHYELTGHMLDIYSVMLTNDNT

LRYWEPEFYDAMYTPHTVLQAVGVCVLCNSQTSLRCGVCIRRPFLCCECCYDHVIS

TLHKLVLSVNPYVCNALGCDVTDVTQLYLGGMNYYCKSHKPSISFPLCANGHVFGL

YKNTCFGSDNVTDFNAIATCDWINAGDYILANTCIERLKLFAAETLKAIEETFKLS

YGIAIVREVLSDRELYLSWEVGKPRPPFNRNYVFTGYRLTKNSKVQIGDYTFEKGD

YVDAVVYRGTTTYRLNVGDYFVLTSHTVIPLSAPTLVPQDHYVRITGLYPTLNISD

DFSSNVANYQKVGIQKYSTLQGPPGTGKSYFAIGLALYYLSARIVYTACSHAAVYT

LCEKALKYFPIDKCSRIIPARARVDCFDKFKVNLTLEQYVFCTVNALPDTTADIVV

FDEISMTTNYDLSVVNARLCAKHYVYIGDSAQLPAPRTLLIKGTLEPEYFNSVCRF

MKTIGPDMFLGTCRRCPSEIVDTVSALVYDNRL

SEQ ID NO: 7 is the amino acid sequence of an additional SARS-COV-2 optimized Region 1 polypeptide (Region 1 SARS-COV-2-EG-2.2):

NCLDDRCVLHCANFNVLFSTVFPFTSFGPLVRKICVDGVPFVVSTGHHFRELG

VVYNQDVNLHSFRLSFKELLLYAADPAMHVASGNLLLDRRTTCESVAALTNNFAFQ

TVKPGNFNKDFYDFALSKGFFKEGSPVELKHFFFVQDGNAAISDYEYYRYNLPTMF

DIRQLLFVFEVVDKYFDCYDGGCINANQVTVNNLDKSAGFPFNKWGKARLYYESMS

-continued

YEDQDVLFAYTKRNVTPTITQMNLKYAISVKNRARTVAGVSICSTITNRQFHQKLL

KSIAATGGATVVIGTSKFYGGWHNILKTVYSDVENPYLMGWDYPKCDRAMPNMLRI

VASLVLARKHTMCCSLSHRFYRLTNECAQVLSEMVICGGSLYVKPGGTSSGDATTA

YANSVFNIFQAVTANVNILLSTDGNKIADNYVRNLQHRLYGCLYRNRDVYTDFVNE

FYTYLRKHFSMIILSAAAVVCFNSTYVSQGLVASIRNFKSVLYYQNNVEMSEVKCW

TETDLIKGPHEFCSQHTILVKQGDDYVYFPYPDPSRILGAGCFVDDVVKTDGTLMV

ERFVSLAIDAYPFTKHPNQEYAYVFHLYLQYIKKLHDELTGHILDMYSVMLINDNT

SRYWESEFYEAMYTSHTVLQAVGSCVLCNSQTLLRCGACIRKPFLCCKCCYDHIIS

TSHKLVFSVNPYVCNVPGCDVTDVTQLCLGGMSYYCKPHKPPISFPLCVNGQVFGL

YKNTCAGSDNVTDFNAISTCDWTNAGDYILANACTERLKLFAAEMLKATEETFKLS

YGVATVREVLSDKELHLSWEVGRPRPPLNRNYVFTGYHVTKNSKVQTGEYTFEKGY

YGDAVVYRGITTYKLNVGDYFLLTSHTVMPLSAPILVPQEHYVRIIGLYPTLNISY

EFSSNVANYQKVGMQRYSTLQGPPGTGKSHFAIGLSLYYPSARIMYTACSHAAVDA

LCDKALKYLPIDKCSRIIPARALVECFDKFKLNSTLEQYVFCTVNALPETTVDIVV

FDEISMTTNYDLSVVNVRLRAKHYVYVGDPAQLPAPRTLLTKGILEPEYFNSVCRL

IKTIGPDMFLRTCRRCPAEIVDTLSALVYDNKL

SEQ ID NO: 8 is the amino acid sequence of a sarbecovirus optimized region 1 polypeptide (Region 1 SARBECO-EG-2.1):

NCLDDRCILHCANFNVLFSTVFPLTSFGPLVRKIFVDGVPFVVSTGYHFRELG

VVHNQDVNIHSSRLSFKELLVYAADPAMHAASGNLLLDKRTTCFSVAALTNNVSFQ

TVKPGNFNKDFYDFAVSKGFFKEGSSVELKHFFFAQDGNAAISDYDYYRYNLPTMC

DIRQLLFVVEVVDKYFDCYDGGCINANQVIVNNLDKSAGFPFNKWGKARLYYDSMS

YEDQDALFAYTKRNVLPTITQMNLKYAISAKNRARTVAGVSICSTMINRQFHQKLL

KSIAATRGATVVIGTSKFYGGWNNMLKTVYSDVETPHLMGWDYPKCDRAMPNMLRI

MASLVLARKHSTCCNLSHRFYRLANECAQVLSEMVMCGGSLYVKPGGTSSGDATTA

YANSVFNICQAVTANVNALLSTDGNKIGDKYIRNLQHRLYECLYRNRDVDHEFVDE

FYAYLRKHFSMMILSAAAVVCYNSNYAAQGLVASIKNFKAVLYYQNNVFMSEAKCW

TETDLTRGPHEFCSQHTMLVKQGDDYVYLPYPDPSRILGAGCFVDDIVKTDGTLMI

ERFVSLAIDAYPLTKHPNQEYADVFHLYLQYIRKLHDELTGHMLDMYSVMLTNDST

SRYWEPEFYEAMYTPHTILQAVGACVLCNSQTSLRCGACIRRPFLCCKCCYDHVIS

TSHKLVLSVNPYVCNATGCDVTDVTQLYLGGMSYYCKAHKPPISFPLCANGQVFGL

YKNTCVGSDNVTDFNAIATCDWTNAGDYILANTCTERLKLFAAETLKATEETFKLS

YGIATVREVLSDRELYLSWEVGKPRPPLNRNYVFTGYRVTKNSKTQIGEYTFEKGD

YGDAVVYRGITTYKLNVGDYFVLTSHTVMPLSAPTLVPQEHYVRITGLYPTLNISE

EFSSNVANYQKIGMQKYSTLQGPPGTGKSHFAIGLALYYPSARIVYTACSHAAVDA

LCEKALKYLPIDKCSRIIPARARVECFDKFKVNSTLEQYVFCTVNALPETTADIVV

FDEISMATNYDLSVVNARLRAKHYVYIGDPAQLPAPRTLLTKGTLEPEYFNSVCRL

MKTIGPDMFLGTCRRCPAEIVDTVSALVYDNKL

SEQ ID NO: 9 is the amino acid sequence of an additional sarbecovirus optimized Region 1 polypeptide (Region 1 SARBECO-EG-2.2):

NCLDDRCILHCANFNVLFSTVFPPTSFGPLVRKIFVDGVPFVVSTGYHFRELG

VVHNQDVNIHSSRLSFKELLVYAADPAMHAASGNLLLDKRTTCFSVAALINSVAFQ

-continued

TVKPGNFNKDFYDFAVSKGFFKEGSSVELKHFFFAQDGNAAISDYDYYRYNLPTMC

DIRQLLFVVEVVDKYFDCYDGGCINANQVIVNNLDKSAGFPFNKWGKARLYYDSMS

YEDQDALFAYTKRNVLPTITQMNLKYAISAKNRARTVAGVSICSTMTNRQFHQKLL

KSIAATRGATVVIGTSKFYGGWNNMLKTVYSDVESPHLMGWDYPKCDRAMPNMLRI

MASLVLARKHNTCCNLSHRFYRLANECAQVLSEMVMCGGSLYVKPGGTSSGDATTA

YANSVFNICQAVTANVNALLSTDGNKIADKYVRNLQHRLYECLYRNRDVDTDFVNE

FYAYLRKHFSMMILSAAAVVCYNSNYAAQGLVASIKNFKSVLYYQNNVFMSEAKCW

TETDLTRGPHEFCSQHTMLVKQGDDYVYLPYPDPSRILGAGCFVDDIVKTDGTLMI

ERFVSLAIDAYPLTKHPNQEYADVFHLYLQYIRKLHDELTGHMLDMYSVMLTNDNT

SRYWEPEFYEAMYTPHTVLQAVGACVLCNSQTSLRCGACIRRPFLCCKCCYDHVIS

TSHKLVLSVNPYVCNAPGCDVTDVTQLYLGGMSYYCKLHKPPISFPLCANGQVFGL

YKNTCVGSDNVTDFNAIATCDWTNAGDYILANTCTERLKLFAAETLKATEETFKLS

YGIATVREVLSDRELHLSWEVGKPRPPLNRNYVFTGYRVTKNSKVQIGEYTFEKGD

YGDAVVYRGTTTYKLNVGDYFVLTSHTVMPLSAPTLVPQEHYVRITGLYPTLNISD

EFSSNVANYQKIGMQKYSTLQGPPGTGKSHFAIGLALYYPSARIVYTACSHAAVDA

LCEKALKYLPIDKCSRIIPARARVECFDKFKVNSTLEQYVFCTVNALPETTADIVV

FDEISMATNYDLSVVNARLRAKHYVYIGDPAQLPAPRTLLTKGTLEPEYFNSVCRL

MKTIGPDMFLGTCRRCPAEIVDTVSALVYDNKL

SEQ ID NO: 10 is the amino acid sequence of an alternative exemplary conserved region SARS-COV-2 polypeptide spanning nsp6 through nsp10 proteins (Region 2)

GGKPCIKVATVQSKMSDVKCTSVVLLSVLQQLRVESSSKLWAQCVQLHNDILL

AKDTTEAFEKMVSLLSVLLSMQGAVDINKLCEEMLDNRATLQAIASEFSSLPSYAA

FATAQEAYEQAVANGDSEVVLKKLKKSLNVAKSEFDRDAAMORKLEKMADQAMTQM

YKQARSEDKRAKVISAMQTMLFTMLRKLDNDALNNIINNARDGCVPLNIIPLTTAA

KLMVVIPDYNTYKNTCDGTTFTYASALWEIQQVVDADSKIVQLSEISMDNSPNLAW

PLIVTALRANSAVKLQNNELSPVALRQMSCAAGTTQTACTDDNALAYYNTTKGGRF

VLALLSDLQDLKWARFPKSDGTGTIYTELEPPCRFVTDTPKGPKVKYLYFIKGLNN

LNRGMVLGSLAATVRLQAGNATEVPANSTVLSFCAFAVDAAKAYKDYLASGGQPIT

NCVKMLCTHTGTGQAITVTPEANMDQESFGGASCCLYCRCHIDHPNPKGFCDLKGK

YVQIPTTCANDPVGFTLKNTVCTVCGMWKGYGCSCDQL

SEQ ID NO: 11 is the amino acid sequence of a SARS-COV-2 Region 2 optimized polypeptide (Region 2 SARS-COV2-EG-2.1):

GGKPCVKVATVQSKISDVKCTSVVLLLVLQQLRVESLSKLWAQCVQLHNDIIL

AKDTTEAFGKMVSLLSVLLSMQRAVDINKLCEEILDNRATLQSIASEFSSLSSYAA

FATAQEAYERAVANGDSEVFLKKLKKSLNVAKSEFDCDAAMQRKLENMADQAMTQM

YKQVRSEDKRAKVTSAMQIMLFTMLRKFDNDALNNIVNNARDGCVPLNIIPFTTAA

KLMVVISDYNTYKNTCDGITFTYASALWEIQHVVDADSKIVQFSEISMDNSSNLAW

PLIVIALRANSAVKLQNNELSPVVLRQMSCAAGTTQTACIDDNALAYYNTIKGGRF

VLALLSNLQDLKWARFPKSDGTGTVYTELEPPCGFVTDTPKGLKVKYLYFIRGLNN

LNRGIVLGSLAATVRLQAGKATEVPANSIVLSFCAFAIDAAKAYKDYLVSGGQPIT

NCVKMLCTHIGTGQAITVIPEANMDQESFGGASCCMYCRCHIDHPDPKGFCDLKGK

YVQIPTICANDPVGFILKNTVCTVCSMWKGYGCSCDQLC

-continued

SEQ ID NO: 12 is the amino acid sequence of an additional SARS-COV-2 optimized Region 2 polypeptide (Region 2 SARS-COV2-EG-2.2):

GGKPCIKVATVQSKTSDVKCTSVVLLSVFQQLRVESSFKLWAQCVQLHNDILL

ARDTTEAFEKMVSLLSVLFSMQGAVDINKFCEEMLDNRAILQAIASEFSSLPSYAA

LATAQEAYEQAVVNGDSEVVLKNLKKSLNVAKSEFDLDAAMQRKLEKMSDQAMTQM

YKQAKSEDKRAKVISAMQTMLFTMFRKLDNDALNNIIDNARDGCVPLNIIPLITAA

KLMVVTPDYNTYKNMCDGTTFIYASALWEIQQVVNADSKIVQLSEVSMDNSPNLAW

PLVVTALRANSAIKLQNNELSPIALRQMSCAAGTIQTACTDDNALVYYNTTKGGRF

VFALLSDLQDLKWARFSKSDGTGTIYIELEPPCRFVTDTLKGPKVKYLYFIKRLNN

LNRGMVLGSLAAIVRLQAGNAIEVPANSTVLFFCAFAVDASKAYKDYLASGGQPII

NCVKMLCTHTGIGQAITVTPEANMEQESFGGASCCLYCRCHIDHSNPKGFCDLKGR

YVQIPTTCVNDPVGFTLKNTVCTICGMWKGYGCGCDQLR

SEQ ID NO: 13 is the amino acid sequence of a sarbecovirus Region 2 optimized polypeptide (Region 2 SARBECO-EG-2.1):

GGKPCIKVATVQSKMSDVKCTSVVLLSVLQQLRVESSSKLWAQCVQLH

NDILLAKDTTEAFEKMVSLLSVLLSMQGAVDINRLCEEMLDNRATLQAIAS

EFSSLPSYAAYATAQEAYEQAVSNGDSEVVLKKLKKSLNVAKSEFDHDAA

MQRKLEKMADQAMTQMYKQARSEDKRAKVTSAMQTMLFTMLRKLDND

ALNNIINNARDGCVPLNIIPLTTAAKLMVVVPDYGTYKNTCDGNTFTYASA

LWEIQQVVDADSKIVQLSEINMDNSPNLAWPLIVTALRANSAVKLQNNELS

PVALRQMSCAAGTTQTACNEDNALAYYNNSKGGRFVLALLSDHQDLKWA

RFPKSDGTGTIYTELEPPCRFVTDTPKGPKVKYLYFIKGLNNLNRGMVLGSL

AATVRLQAGNATEVPANSTVLSFCAFAVDPAKAYKDYLSSGGQPITNCVK

MLCTHTGTGQAITVTPEANMDQESFGGASCCLYCRCHIDHPNPKGYCELKG

KYVQIPTTCANDPVGFTLRNTVCTVCGMWKGYGCSCDQLR

SEQ ID NO: 14 is the amino acid sequence of an additional sarbecovirus region 2 optimized polypeptide (Region 2 SARBECO-EG-2.2):

GGKPCIKVATVQSKMSDVKCTSVVLLSVLQQLRVESSSKLWAQCVQLH

NDILLAKDTTEAFEKMVSLLSVLLSMQGAVDINRLCEEMLDNRATLQAIAS

EFSSLPSYAAFATAQEAYEQAVANGDSEVVLKKLKKSLNVAKSEFDRDAA

MQRKLEKMADQAMTQMYKQARSEDKRAKVTSAMQTMLFTMLRKLDND

ALNNIINNARDGCVPLNIIPLTTAAKLMVVVPDYNTYKNTCEGSTFTYASAL

WEIQQVVDADSKIVPLSEINMDNSQNLAWPLIVTALRANSAVKLQNNELSP

VALRQMSCAAGTTQTACTDDNALAYYNTSKGGRFVLALLSDLQDLKWAR

FPKSDGTGTIYTELEPPCRFVTDTPKGPKVKYLYFIKGLNNLNRGMVLGSLA

ATVRLQAGNATEVPANSTVLSFCAFAVDASKAYRDYLASGGQPITNCVKM

LCTHTGTGQAITVTPEANMDQESFGGASCCLYCRCHIDHPNPKGFCDLKGK

YVQIPTTCANDPVGFTLRNTVCTVCGMWKGYGCSCDQLR

SEQ ID NO: 15 is an exemplary nucleic acid sequence encoding the protein of SEQ ID NO: 5.

SEQ ID NO: 16 is an exemplary nucleic acid sequence encoding the protein of SEQ ID NO: 3.

SEQ ID NO: 17 is an exemplary nucleic acid sequence encoding the protein of SEQ ID NO: 2.

SEQ ID NO: 18 is the amino acid sequence of COVconsv.

DETAILED DESCRIPTION

T-cell responses play an important part in viral clearance of influenza during infection, and are critical for mediating clearance of coronavirus and other acute viral infections of the lung. Furthermore, vaccine elicited cytotoxic T lymphocyte (CTL) responses can protect mice from lethal challenges with SARS coronavirus (CoV). Disclosed here are immunogenic polypeptides and nucleic acids encoding such polypeptides, designed using regions of the virus that are very highly or even totally conserved in the current outbreak, but are also highly conserved among other CoVs, thus identifying regions of the virus that are potentially vulnerable to immune attack. Provided are compositions and methods for eliciting T-cell responses to a spectrum of diverse viruses in a subject, with the targeted diversity coverage selected to include Sarbecoviruses in bats, pangolins, and humans, or alternatively the viral diversity that has evolved within the SARS-CoV-2 global pandemic. The methods include administering to the subject a composition comprising one or more of the disclosed polypeptides or one or more nucleic acids encoding the disclosed polypeptides. The specific regions of the coronavirus proteome targeted include the most conserved regions in the viral proteome across a diverse sampling of Sarbecoviruses.

Sarbecoviruses are a highly diverse subgenus of the family Coronaviridae. Sarbecoviruses are common in bats and also found in pangolins and other mammals, and members of this subgenus have twice have entered the human population, the SARS CoV-1 epidemic nearly two decades ago, and the current SARS CoV-2 epidemic. The intent of defining highly conserved regions was two-fold. First, if these regions were immunogenic when delivered in a vaccine, and could elicit effective T cell responses that could prevent disease, the responses would be highly likely to be cross-reactive and potentially able to protect vaccinated individuals and allow a rapid response should another Sarbecovirus undergo zoonosis in the future. Second, it is believed that protein regions that are highly conserved among diverse population are under fitness constraints and would not be able to readily escape immune responses. Furthermore, T cell responses may be a factor in the disease severity outcome for people infected with SARS-CoV-2, and vaccine-elicited responses T cell responses to epitopes in highly conserved regions of the virus across Sarbecoviruses would not readily be able to evade the response through viral escape. Thus vaccine-elicited responses to conserved regions may be beneficial in terms of disease outcomes in the more limited diversity setting of SARS-CoV-2.

This conserved region approach, where a long stretch of contiguous amino acids are used, is believed to likely be optimal for a T-cell vaccine strategy, because it maximizes the number of potential epitopes that can be targeted, and if T cell responses are elicited, because they are by definition from conserved regions, such T cell responses are highly likely to be cross-reactive with variants, and also to be difficult to escape without a fitness cost. The cross-reactive potential confers value at the population level. The fitness cost of escape may help contain the virus in vivo. CTL responses in natural COVID-19 infection may help with improving disease outcomes, and CTL escape variants that arise in vivo may be associated with more serious outcomes, but would seldom be transmitted as they would arise after the period of high transmissibility early in infection. Thus even if escape mutations in CTL epitopes are rarely observed at the population level, they may still be relevant to disease outcome. Therefore, a vaccine that re-directed the response to conserved epitope(s) with a high mutation cost for escape could be valuable. Larger regions are utilized rather than alternative strategies that target a series of known epitopes, very short extremely conserved regions, or topologically constrained epitopes within short fragments, because longer conserved stretches will contain many more overlapping potential epitopes, and they are more likely to be targeted multiple times by most people.

The specific components in some embodiments include artificial sequences derived using the Epigraph algorithm (designated herein as sequences named "EG"), and these are designed to be complementary to, and in some instances used in combination with, the natural ancestral sequence of the COVID-19 pandemic that was first identified in Wuhan, China.

I. Terms

Unless otherwise noted, technical terms are used according to conventional usage. Definitions of common terms in molecular biology may be found in *Lewin's Genes* X, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics,* 3$^{rd}$ Edition, Springer, 2008 (ISBN: 1402067534), and other similar references, Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety, as are the GenBank® Accession numbers. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Adjuvant: A vehicle or composition used to enhance antigenicity. Adjuvants include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L and 41 BBL. Adjuvants can be used in combination with the disclosed conserved region polypeptides and nucleic acids.

Administration: The introduction of a composition into a subject by a chosen route. For example, if the chosen route is intramuscular, the composition (such as a disclosed antigen) is administered by introducing the composition intramuscularly into a subject.

Coronavirus: A family of positive-sense, single-stranded RNA viruses that can infect humans and non-human animals. The viral envelope is comprised of a lipid bilayer containing the viral membrane (M), envelope (E) and spike (S) proteins. Most coronaviruses cause mild to moderate upper respiratory tract illness, such as the common cold. However, three coronaviruses have emerged that can cause more serious illness and death in humans: severe acute respiratory syndrome coronavirus (SARS-CoV), SARS-CoV-2, and Middle East respiratory syndrome coronavirus (MERS-CoV). Other coronaviruses that infect humans include human coronavirus HKU1 (HKU1-CoV), human coronavirus OC43 (OC43-CoV), human coronavirus 229E (229E-CoV), human coronavirus NL63 (NL63-CoV). SARS-CoV-1, SARS-CoV-2, and related bat and pangolin viruses are members of the subgenus Sarbecovirus (group 2b).

Immunogen: A compound, composition, or substance that can stimulate the production of antibodies or a T cell response in a subject, including compositions that are injected or absorbed into a subject. An immunogen reacts with the products of specific humoral or cellular immunity, including those induced by heterologous antigens, such as the disclosed antigens. "Epitope" or "immunogenic determinant" refers to the region of an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance.

Examples of immunogens include, but are not limited to, peptides, lipids, polysaccharides, and nucleic acids containing antigenic determinants, such as those recognized by an immune cell. In some examples, immunogens include peptides derived from a pathogen of interest. In specific examples, an immunogen is derived from a coronavirus, for example, one or more coronavirus polypeptides or a fragment thereof, such as at least a portion of one or more of RNA-dependent RNA polymerase, helicase, and nsp6-10 proteins or variants thereof.

Immunogenic polypeptide: A protein or a portion thereof that is capable of inducing an immune response in a subject, such as a subject infected or at risk of infection with a pathogen. Administration of an immunogenic polypeptide or its coding sequence derived from a pathogen of interest can induce an immune response. Administration of an immunogenic polypeptide or its coding sequence can in some examples lead to protective immunity against a pathogen of interest. In some examples, an immunogenic polypeptide is a polypeptide including one or more conserved regions from a coronavirus proteome, for example, a polypeptide including one or more conserved regions.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a $CD4^+$ T cell response or a $CD8^+$ T cell response.

Immunogenic composition: A composition comprising an immunogenic polypeptide or a nucleic acid encoding an immunogenic polypeptide that induces a measurable immune response, for example, a measurable CTL response against virus expressing the immunogenic polypeptide or a portion thereof, a measurable helper T cell response, or a measurable B cell response (such as production of antibodies) against the immunogenic polypeptide or a portion thereof. In one example, an "immunogenic composition" is composition including one or more conserved region polypeptides from a coronavirus, such as the conserved regions disclosed herein. It further refers to isolated nucleic acids encoding an immunogenic polypeptide, such as a nucleic acid (for example, a vector or an mRNA) that can be used to express the immunogenic polypeptide (and thus be used to elicit an immune response against the polypeptide or a portion thereof).

For in vitro use, an immunogenic composition may consist of at least one (such as two or more) isolated polypeptide, peptide epitope, or nucleic acids encoding the polypeptide or peptide epitope. For in vivo use, the immunogenic composition will typically include at least one (such as one, two, three, four, five, or more) polypeptide, peptide, or nucleic acid in a pharmaceutically acceptable carrier, and may also include other agents (such as adjuvant(s)). Any particular peptide, such as a disclosed conserved region polypeptide or a nucleic acid encoding the polypeptide, can be readily tested for its ability to induce an immune response by art-recognized assays. Immunogenic compositions can include adjuvants, which are well known to one of skill in the art.

Isolated: An "isolated" biological component (such as a protein, for example a disclosed polypeptide or nucleic acid encoding such a polypeptide) has been substantially separated or purified away from other biological components, such as other chromosomal and extrachromosomal DNA, RNA, and proteins. Proteins, peptides, and nucleic acids that have been "isolated" include proteins purified by standard purification methods. The term also embraces proteins or peptides prepared by recombinant expression in a host cell as well as chemically synthesized proteins, peptides, and nucleic acid molecules. Isolated does not require absolute purity, and can include protein, peptide, or nucleic acid molecules that are at least 50% isolated, such as at least 75%, 80%, 90%, 95%, 98%, 99%, or even 99.9% isolated.

Operably linked: A first nucleic acid is operably linked with a second nucleic acid when the first nucleic acid is placed in a functional relationship with the second nucleic acid. For instance, a promoter is operably linked to a coding sequence if the promoter affects the transcription or expression of the coding sequence. Generally, operably linked nucleic acids are contiguous and, where necessary to join two protein-coding regions, in the same reading frame. In some examples, the operably linked nucleic acids are heterologous, for example, the first and second nucleic acids are from different organisms, different genes, or different polypeptides and the resulting nucleic acid is not naturally occurring.

Pharmaceutically acceptable carriers: The pharmaceutically acceptable carriers useful in this disclosure are known to one of ordinary skill in the art. *Remington: The Science and Practice of Pharmacy*, The University of the Sciences in Philadelphia, Editor, Lippincott, Williams, & Wilkins, Philadelphia, PA, 21st Edition (2005), describes compositions and formulations suitable for pharmaceutical delivery of the proteins, nucleic acids, and other compositions herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions, powder, pill, tablet, or capsule forms, conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: Any compound composed of amino acids, amino acid analogs, chemically bound together. The term polypeptide as used herein includes oligomers of amino acids, amino acid analogs, or small and large peptides, including proteins. Any chain of amino acids, regardless of length or post-translational modification (such as glycosylation or phosphorylation) is referred to as a polypeptide. The term polypeptide applies to amino acid polymers including naturally occurring amino acid polymers and non-naturally occurring amino acid polymers as well as polymers in which one or more amino acid residue is a non-natural amino acid, for example an artificial chemical mimetic of a corresponding naturally occurring amino acid. As used herein, polypeptide also refers to recombinant amino acid polymers, such as polymers including portions that are obtained from different (typically noncontiguous) portions of a genome (such as a coronavirus genome) and/or are obtained from different genomes (such as two or more distinct coronaviruses). A "residue" refers to an amino acid or amino acid mimetic incorporated in a polypeptide by an amide bond or amide bond mimetic.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease. A "prophylactic" treatment is a treatment administered to a subject who does not exhibit signs of a disease or exhibits only early signs for the purpose of decreasing the risk of developing pathology. The prophylactic treatment can be pre-exposure or post-exposure.

Purified: The term purified does not require absolute purity; rather, it is intended as a relative term. Thus, for example, a purified protein is one in which the protein is more enriched than the protein is in its natural environment within a cell. Preferably, a preparation is purified such that the protein represents at least 50% of the protein content of the preparation.

Recombinant nucleic acid or polypeptide: A nucleic acid molecule or polypeptide that is not naturally occurring or has a sequence that is made by an artificial combination of two otherwise separated segments of nucleotide or amino acid sequence. This artificial combination is accomplished by chemical synthesis or, more commonly, by the artificial manipulation of isolated segments of nucleic acids, e.g., by genetic engineering techniques such as those described in Sambrook et al. (ed.), *Molecular Cloning: A Laboratory Manual,* $2^{nd}$ ed., vol. 1-3, Cold Spring Harbor Laboratory Press, Cold Spring Harbor, N Y, 1989. The term "recombinant" includes nucleic acids or polypeptides that have been altered solely by addition, substitution, or deletion of a portion of a natural nucleic acid molecule or peptide.

Sequence identity/similarity: Sequence identity between two or more nucleic acid sequences or between two or more amino acid sequences can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. The NCBI Basic Local Alignment Search Tool (BLAST) is available from several sources, including the National Center for Biological Information (NCBI, National Library of Medicine, Building 38A, Room 8N805, Bethesda, MD 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

In some examples, sequence similarity is assessed by the conservation of epitope-length fragments. The use of this measure of similarity was developed at Los Alamos National Laboratory, and tools are available on the World Wide Web at hiv.lanl.gov.

Subject: Living multi-cellular vertebrate organisms, a category that includes both human and non-human mammals (including non-human primates).

Therapeutically effective amount or Effective amount: The amount of agent, such as nucleic acid, polypeptide, or other therapeutic agent, that is sufficient to prevent, treat (including prophylaxis), reduce, and/or ameliorate the symptoms and/or underlying causes of any of a disorder or disease. In some embodiments, an "effective amount" is sufficient to reduce or eliminate a symptom of a disease, such as coronavirus infection, for example, COVID19. For instance, this can be the amount necessary to inhibit viral replication or to measurably alter outward symptoms of the viral infection. In general, this amount will be sufficient to measurably inhibit virus replication or infectivity.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a $CD8^+$ T cell is a cytotoxic T lymphocyte (CTL). In another embodiment, a $CD8^+$ cell is a suppressor T cell.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Vaccine: A pharmaceutical composition that elicits a prophylactic or therapeutic immune response in a subject. In some cases, the immune response is a protective immune response and can block subsequent infection, in other cases it can limit the pathological impact of an infection by containing the infection. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed polypeptide), a peptide or polypeptide, a virus, a cell, or one or more cellular constituents.

Vector: A nucleic acid molecule that can be introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

II. Immunogenic Compositions

Provided herein are immunogenic compositions and methods of use for eliciting an immune response to a coronavirus (such as SARS-CoV-2) in a subject. In some embodiments, the compositions include optimized viral polypeptides that are computationally derived from naturally-occurring coronavirus proteomes. The optimized viral polypeptides allow for improved virus-specific immunity (e.g., T cell-based immune responses) following administration to a subject. In some embodiments, the composition includes at least two different optimized viral polypeptides for each represented viral polypeptide. Including at least two different optimized viral polypeptides allows for increased coverage and representation of immunogenic epitopes in the composition.

In some embodiments, the immunogenic composition includes one or more (such as 1, 2, 3, or more) polypeptides that are optimized to cover 9-mer diversity in a conserved region of SARS-CoV-2 proteomes. In other embodiments, the immunogenic composition includes one or more (such as 1, 2, 3, or more) polypeptides that are optimized to cover 9-mer diversity in a conserved region of Sarbecovirus proteomes (e.g., "pan-Sarbecovirus"). In other embodiments, the immunogenic composition includes one or more (such as 1, 2, 3, or more) nucleic acids encoding one or more of the disclosed polypeptides.

Exemplary amino acid sequences of coronavirus polypeptides included in the compositions and methods provided herein or encoded by the nucleic acids included in the compositions and methods provided herein include SEQ ID NOs: 1-14 and 18. In some examples, the disclosed polypeptides include, consist essentially of, or consist of an amino acid sequence at least 95% identical to the amino acid sequence of any one of SEQ ID NOs: 1-14 and 18, such as at least 95% identical, at least 96% identical, at least 97% identical, at least 98% identical, at least 99% identical, or even 100% identical to the amino acid sequence of any one of SEQ ID NOs: 1-14 and 18. In some non-limiting embodiments, the components have at least the percent identity shown in Table 1, compared to a naturally occurring (e.g., Wuhan reference strain, GenBank® Accession No. NC_045512) coronavirus, such as the indicated sequences provided herein.

TABLE 1

Exemplary sequence identity of disclosed vaccine polypeptides

| | Region 1 | | Region 2 | |
|---|---|---|---|---|
| | SARS-CoV-2 | Sarbeco | SARS-CoV-2 | Sarbeco |
| Reference | SEQ ID NO: 1 | SEQ ID NO: 1 | SEQ ID NO: 10 | SEQ ID NO: 10 |

TABLE 1-continued

Exemplary sequence identity of disclosed vaccine polypeptides

| | Region 1 | | Region 2 | |
|---|---|---|---|---|
| | SARS-CoV-2 | Sarbeco | SARS-CoV-2 | Sarbeco |
| Epigraph 1 | 96% (SEQ ID NO: 6) | 98% (SEQ ID NO: 8) | 95% (SEQ ID NO: 11) | 97% (SEQ ID NO: 13) |
| Epigraph 2 | 96% (SEQ ID NO: 7) | 99% (SEQ ID NO: 9) | 95% (SEQ ID NO: 12) | 98% (SEQ ID NO: 14) |

In particular embodiments, the disclosed compositions include one or more (such as 1, 2, 3, or more) polypeptides or one or more nucleic acids (such as 1, 2, 3, or more) encoding the polypeptides. In some embodiments, the compositions include one or more polypeptides or nucleic acids encoding polypeptides eliciting T-cell responses to a spectrum of diverse viruses in a subject, with the targeted diversity coverage selected to include the viral diversity that has evolved within the SARS-CoV-2 global pandemic. Thus, in some examples, the compositions include one or more "SARS-CoV-2 Region 1" polypeptides or nucleic acids encoding polypeptides selected from sequences with at least 95% sequence identity (such as at least 95%, at least 96%, at least 97%, at least 98%, at least 99%, or even 100% sequence identity) to SEQ ID NOs: 5-7. In particular examples, the compositions include polypeptides or nucleic acids encoding polypeptides as follows: SEQ ID NO: 5 and SEQ ID NO: 6; or SEQ ID NO: 5, SEQ ID NO: 6, and SEQ ID NO: 7; or SEQ ID NO: 5 and SEQ ID NO: 7. In other examples, the compositions include one or more "SARS-CoV-2 Region 2" polypeptides or nucleic acids encoding polypeptides selected from sequences with at least 95% sequence identity (such as at least 95%, at least 96%, at least 97%, at least 98%, at least 99%, or even 100% sequence identity) to SEQ ID NOs: 10-12. In particular examples, the compositions include polypeptides or nucleic acids encoding polypeptides as follows: SEQ ID NO: 10; or SEQ ID NO: 10 and SEQ ID NO: 11; or SEQ ID NO: 10, SEQ ID NO: 11, and SEQ ID NO: 12; or SEQ ID NO: 10 and SEQ ID NO: 12.

In other embodiments, the compositions include one or more polypeptides or nucleic acids encoding polypeptides eliciting T-cell responses to a spectrum of diverse viruses in a subject, with the targeted diversity coverage selected to include Sarbecoviruses in bats, pangolins, and humans. Thus, in some examples, the compositions include one or more "Sarbecovirus Region 1" polypeptides or nucleic acids encoding polypeptides selected from sequences with at least 95% sequence identity (such as at least 95%, at least 96%, at least 97%, at least 98%, at least 99%, or even 100% sequence identity) to SEQ ID NOs: 5, 8, and 9. In particular examples, the compositions include polypeptides or nucleic acids encoding polypeptides as follows: SEQ ID NO: 5 and SEQ ID NO: 8; or SEQ ID NO: 5, SEQ ID NO: 8, and SEQ ID NO: 9; or SEQ ID NO: 5 and SEQ ID NO: 9. In other examples, the compositions include one or more "Sarbecovirus Region 2" polypeptides or nucleic acids encoding polypeptides selected from sequences with at least 95% sequence identity (such as at least 95%, at least 96%, at least 97%, at least 98%, at least 99%, or even 100% sequence identity) to SEQ ID NOs: 10, 13, and 14. In particular examples, the compositions include polypeptides or nucleic acids encoding polypeptides as follows: SEQ ID NO: 10; or SEQ ID NO: 10 and SEQ ID NO: 13; or SEQ ID NO: 10, SEQ ID NO: 13, and SEQ ID NO: 14; or SEQ ID NO: 10 and SEQ ID NO: 14.

Nucleic acids encoding the disclosed polypeptides (e.g., SEQ ID NOs: 1-14 and 18) are also disclosed herein. Unless otherwise specified, a "nucleic acid encoding a polypeptide" includes all nucleotide sequences that are degenerate versions of each other and encode the same amino acid sequence. For example, a polynucleotide encoding a disclosed immunogenic polypeptide includes a nucleic acid sequence that is degenerate as a result of the genetic code. There are 20 natural amino acids, most of which are specified by more than one codon. Therefore, all degenerate nucleotide sequences are included as long as the amino acid sequence of the polypeptide encoded by the nucleotide sequence is unchanged. In some embodiments, the disclosed polypeptide sequences are back-translated to codon optimized DNA. In particular non-limiting examples, the nucleic acids include the sequences set forth as SEQ ID NOs: 15-17.

In some embodiments, the nucleic acid encoding a disclosed polypeptide is DNA, RNA, or mRNA. In some embodiments, the nucleic acid may include one or more modified, alternative, or synthetic nucleotides or nucleosides. Modified, alternative, or synthetic nucleotides or nucleosides may be included for reasons including but not limited to improving stability of the nucleic acid in which they are incorporated, decreasing potential immunogenicity of, or immune response to, the nucleic acid, or other advantageous properties. In some examples, the nucleic acid includes one or more chemical modifications to the sugar, base, and/or internucleoside linkages. Exemplary modifications to the sugar include, but are not limited to, bridged nucleic acids (such as locked nucleic acid (LNA) and 2',4'-constrained ethyl nucleic acid ((S)-cET)), 2'-O-methyl (OMe), 2'-O-methoxy-ethyl (MOE), 2'-fluoro, cEt and tricyclo (tc)-DNA. Modifications to the internucleoside linkages include, for example, phosphorothioate and phosphoramidate, or peptide nucleic acid. In other examples, the nucleic acid is RNA and may include one or more modified nucleosides, such as $m^5C$ (5-methylcytidine); $m^5U$ (5-methyluridine); $m^6A$ ($N^6$-methyladenosine); $s^2U$ (2-thiouridine); pseudouridine; Um (2'-O-methyluridine); $m^1A$ (1-methyladenosine); $m^2A$ (2-methyladenosine); Am (2'-O-methyladenosine); $ms^2$ $m^6A$ (2-methylthio-$N^6$-methyladenosine); $i^6A$ ($N^6$-isopentenyladenosine); $ms^2i6A$ (2-methylthio-$N^6$ isopentenyladenosine); $io^6A$ ($N^6$-(cis-hydroxyisopentenyl)adenosine); $ms^2i6A$ (2-methylthio-$N^6$-(cis-hydroxyisopentenyl)adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$-threonylcarbamoyladenosine); $hn^6A$ ($N^6$-hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$($N^4$-acetylcytidine); $f^5C$ (5-formylcytidine); $m^5Cm$ (5,2'-O-dimethylcytidine); $ac^4Cm$ ($N^4$-acetyl-2'-O-methylcytidine); $k^2C$ (lysidine); $m^1G$ (1-methylguanosine); $m^2G$ ($N^2$-methylguanosine); $m^7G$ (7-methylguanosine); Gm (2'-O-methylguanosine); $m^{22}G$ ($N^2$,$N^2$-dimethylguanosine); $m^2Gm$ ($N^2$,2'-O-dimethylguanosine); $m^{22}Gm$ ($N^2$,$N^2$,2'-O-trimethylguanosine); Gr(p) (2'-O-ribosylguanosine (phosphate)); yW (wybutosine); $o_2yW$ (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); $preQ_0$ (7-cyano-7-deazaguanosine); $preQ_1$ (7-aminomethyl-7-deazaguanosine); $G^+$ (archaeosine); D (dihydrouridine); $m^5Um$ (5,2'-O-dimethyluridine); $s^4U$ (4-thiouridine); $m^5s^2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $memo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-O-methyluridine); $mcm^5s^2U$ (5-methoxycarbonylmethyl-2-thiouridine); $nm^5s^2U$ (5-aminomethyl-2-thiouridine); $mnm^5U$ (5-methylaminomethyluridine); $mnm^5s^2U$ (5-methylaminomethyl-2-thiouridine); $mnm^5se^2U$ (5-methylaminomethyl-2-selenouridine); $ncm^5U$ (5-carbamoylmethyluridine); $ncm^5Um$ (5-carbamoylmethyl-2'-O-methyluridine); $cmnm^5U$ (5-carboxymethylaminomethyluridine); $cmnm^5Um$ (5-carboxymethylaminomethyl-2'-O-methyluridine); $cmnm^5s^2U$ (5-carboxymethylaminomethyl-2-thiouridine); $m^6{}_2A$ ($N^6$, $N^6$-dimethyladenosine); Im (2'-O-methylinosine); $m^4C$($N^4$-methylcytidine); $m^4Cm$ ($N^4$,2'-O-dimethylcytidine); $hm^5C$ (5-hydroxymethylcytidine); $m^3U$ (3-methyluridine); $cm^5U$ (5-carboxymethyluridine); $m^6Am$ ($N^6$,2'-O-dimethyladenosine); $m^6{}_2Am$ ($N^6$,$N^6$,0-2'-trimethyladenosine); $m^{2,7}G$ ($N^2$,7-dimethylguanosine); $m^{2,2,7}G$ ($N^2$,$N^2$,7-trimethylguanosine); $m^3Um$ (3,2'-O-dimethyluridine); $m^5D$ (5-methyldihydrouridine); $f^5Cm$ (5-formyl-2'-O-methylcytidine); $m^1Gm$ (1,2'-O-dimethylguanosine); $m^1Am$ (1,2'-O-dimethyladenosine); $\tau m^5U$ (5-taurinomethyluridine); $\tau m^5s^2U$ (5-taurinomethyl-2-thiouridine)); imG-14 (4-demethylwyosine); imG2 (isowyosine); $ac^6A$ ($N^6$-acetyladenosine); 1-methylpseudouridine; 5-methoxyuridine; or 5-methylcytidine.

In particular examples, the nucleic acid is mRNA. In some examples, the nucleic acid (such as an mRNA) is formulated with a lipid nanoparticle (LNP). See, e.g., Pardi et al., *Nat. Commun.* 9:3361, 2018; Pardi et al., *Mol. Ther. Nucleic Acids* 15:36-47, 2019; both of which are incorporated herein by reference in their entirety. The mRNA may include one or more modified nucleosides, which in non-limiting examples may be 1-methylpseudouridine, 5-methylcytidine, or both. Additional modified nucleosides that may be used are set out above. Such modifications may reduce innate immune responses that can inhibit synthesis of the encoded immunogen. The mRNA is incorporated in a lipid nanoparticle, which may decrease degradation of the mRNA and/or facilitate cellular uptake, for example, compared to naked mRNA. Exemplary lipid nanoparticles that can be used include, but are not limited to, Lipid H (see, e.g., Hassett et al., *Mol. Ther. Nucleic Acids* 15:1-11, 2019), Acuitas ALC-0315 (see, e.g., International Pat. Publ. WO 2017/075531), imidazole cholesterol ester (ICE) based lipids (see e.g., U.S. Pat. Publ. 2020/0155691), cystine cationic lipids (e.g., International Pat. Publ. No. WO 2020/214946), Lipid 2,2 (8,8)4C CH3 (see, e.g., U.S. Pat. No. 9,670,152), Acuitas A9 (see, e.g., U.S. Pat. No. 10,221,127), and Genevant CL1 (see, e.g., International Pat. Publ. WO 2020/219941).

In other embodiments, a nucleic acid encoding a disclosed polypeptide is incorporated into a vector. In some embodiments, the vector is a viral vector. Viral vectors that can be used to express the disclosed polypeptides include polyoma, e.g., SV40; adenovirus; non-replicating adenoviruses of chimpanzee origin (ChAdV); vaccinia virus; modified vaccinia Ankara (MVA) virus; adeno-associated virus; herpes viruses, including HSV and EBV; Sindbis viruses; alphaviruses; and retroviruses of avian, murine, and human origin. Baculovirus (*Autographa californica* multinuclear polyhedrosis virus; AcMNPV) vectors are also known in the art, and may be obtained from commercial sources (such as PharMingen®, San Diego, Calif.; Protein Sciences Corp., Meriden, Conn.; Stratagene®, La Jolla, Calif.).

In some examples, vector includes a nucleic acid encoding a disclosed protein operably linked to a promoter. In non-limiting examples, the promoter is a cytomegalovirus (CMV) promoter (such as a CMV immediate early promoter), an SV40 promoter, an elongation factor 1α (EF1a) promoter, a phosphoglycerate kinase (PGK) promoter, or a β-actin promoter, such as a chicken β-actin promoter. One of skill in the art can select additional promoters that can be used in the disclosed vectors. In additional examples, the nucleic acid is also operably linked to an enhancer element (such as a CMV enhancer) and/or a polyadenylation signal (such as a β-globin polyadenylation signal or an SV40 polyadenylation signal). Other elements that optionally can be included in the vector include tags (such as 6×His, HA, or other tags for protein detection).

In some embodiments, the vector is an adenovirus vector. In some examples, the adenovirus vector is a recombinant adenovirus vector. In other examples, the adenovirus vector is a replication-competent adenovirus vector. In further examples, the adenovirus vector is a replication-deficient adenovirus vector. In some non-limiting examples, the adenovirus vector is derived from human adenovirus, such as an adenovirus serotype 5 (Ad5), adenovirus serotype 26 (Ad26), adenovirus serotype 35 (Ad35), or adenovirus serotype 52 (Ad52) vector. In other non-limiting examples, the adenovirus is a simian adenovirus (SAdV), such as of chimpanzee origin (ChAdV) or derived from a ChAdV. One potential advantage to using a ChAdV is that there may be lower prevalence of pre-existing antibodies against the vector in the human population. In some examples, the vector is ChAdO×1, which is derived from SAdV isolate Y25 of group E adenoviruses, modified by HAdV-5 E4 Orf4 and Orf6/7 (Ondondo et al., *Mol. Ther.* 24:832-842, 2016). In further examples, the vector is ChAdO×2, which is a C68 genome modified by removal of the E1 and E3 regions, and substitution of the E4 region with E4Orf4, Orf6, and Orf6/7 from HAdV-5 and E4Orf1, Orf2, and Orf3 from SAdV Y25 (see, e.g., US Pat. Publ. 2019/0175716).

Pharmaceutical compositions including the disclosed polypeptides, nucleic acids encoding the polypeptides, and/or vectors are also disclosed herein. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing. The immunogenic compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

Formulated compositions, especially liquid formulations, may contain a bacteriostat to prevent or minimize degradation during storage, including but not limited to effective concentrations (usually 1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The pharmaceutical composition may optionally include an adjuvant to enhance an immune response of the host. Suitable adjuvants are, for example, toll-like receptor agonists, alum, $AlPO_4$, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa®, Hamilton, IN) and IL-12 (Genetics Institute®, Cambridge, MA), may be used as an adjuvant. These adjuvants have the advantage in that they help to stimulate the immune system in a non-specific way, thus enhancing the immune response to a pharmaceutical product. In some embodiments, an adjuvant is not required and is thus not included in the composition, or may be administered to a subject separately from the immunogenic composition.

In some embodiments, the compositions are provided as a sterile composition. The pharmaceutical composition typically contains an effective amount of a disclosed immunogen and can be prepared by techniques known to one of skill in the art. Typically, the amount of immunogen in each dose of the immunogenic composition is selected as an amount which elicits an immune response without significant, adverse side effects.

In some embodiments, the composition can be provided in unit dosage form for use to elicit an immune response in a subject, for example, to prevent or inhibit SARS-CoV-2 infection in the subject. A unit dosage form contains a suitable single preselected dosage for administration to a subject, or suitable marked or measured multiples of two or more preselected unit dosages, and/or a metering mechanism for administering the unit dose or multiples thereof.

In some embodiments, a pharmaceutical composition includes one or more nucleic acids encoding a disclosed polypeptide or a vector including one or more nucleic acids encoding a disclosed polypeptide. A therapeutically effective amount of the nucleic acid(s) can be administered to a subject in order to generate an immune response. In various embodiments, a nucleic acid encoding a biological adjuvant (such as those described above) can be cloned into same vector as a nucleic acid encoding a disclosed polypeptide, or the nucleic acid can be cloned into one or more separate vectors for co-administration. In addition, nonspecific immunomodulating factors such as *Bacillus* Calmette-Guerin (BCG) and levamisole can be co-administered.

III. Methods of Eliciting an Immune Response

The immunogenic polypeptides disclosed herein (such as SEQ ID NOs: 1-14 and 18, or polypeptides having at least 95% sequence identity to SEQ ID NOs: 1-14 and 18) or nucleic acids encoding the disclosed polypeptides can be administered to a subject to elicit an immune response in the subject, such as an immune response to a coronavirus (e.g., SARS-CoV-2). In some embodiments, one or more of the disclosed polypeptides (or one or more nucleic acids encoding the disclosed polypeptides) is administered to a subject with coronavirus infection or at risk of coronavirus infection. In some embodiments, the one or more immunogenic polypeptides or nucleic acids are administered in an amount sufficient to elicit an immune response to coronavirus in the subject. In particular examples, the immune response is a T cell immune response, such as a CTL response.

In particular embodiments, the methods include administering one or more (such as 1, 2, 3, or more) polypeptides or one or more (such as 1, 2, 3, or more) nucleic acids encoding the polypeptides to a subject. In some embodiments, the subject is administered a composition including one or more polypeptides or nucleic acids encoding polypeptides eliciting T-cell responses to a spectrum of diverse viruses in a subject, with the targeted diversity coverage selected to include the viral diversity that has evolved within the SARS-CoV-2 global pandemic. Thus, in some examples, the subject is administered one or more "SARS-CoV-2 Region 1" polypeptides or nucleic acids encoding polypeptides selected from sequences with at least 95% sequence identity (such as at least 95%, at least 96%, at least 97%, at least 98%, at least 99%, or even 100% sequence identity) to SEQ ID NOs: 5-7. In particular examples, the subject is administered polypeptides or nucleic acids encoding polypeptides as follows: SEQ ID NO: 5 and SEQ ID NO: 6; or SEQ ID NO: 5, SEQ ID NO: 6, and SEQ ID NO: 7; or SEQ ID NO: 5 and SEQ ID NO: 7. In other examples, the subject is administered one or more "SARS-CoV-2 Region 2" polypeptides or nucleic acids encoding polypeptides selected from sequences with at least 95% sequence identity (such as at least 95%, at least 96%, at least 97%, at least 98%, at least 99%, or even 100% sequence identity) to SEQ ID NOs: 10-12. In particular examples, the subject is administered a composition including polypeptides or nucleic acids encoding polypeptides as follows: SEQ ID NO: 10; or SEQ ID NO: 10 and SEQ ID NO: 11; or SEQ ID NO: 10, SEQ ID NO: 11, and SEQ ID NO: 12; or SEQ ID NO: 10 and SEQ ID NO: 12.

In other embodiments, the methods include administering to a subject a composition including one or more polypeptides or nucleic acids encoding polypeptides eliciting T-cell responses to a spectrum of diverse viruses in a subject, with the targeted diversity coverage selected to include Sarbecoviruses in bats, pangolins, and humans. Thus, in some examples, the subject is administered a composition including one or more "Sarbecovirus Region 1" polypeptides or nucleic acids encoding polypeptides selected from sequences with at least 95% sequence identity (such as at least 95%, at least 96%, at least 97%, at least 98%, at least 99%, or even 100% sequence identity) to SEQ ID NOs: 5, 8, and 9. In particular examples, the subject is administered a composition including polypeptides or nucleic acids encoding polypeptides as follows: SEQ ID NO: 5 and SEQ ID NO: 8; or SEQ ID NO: 5, SEQ ID NO: 8, and SEQ ID NO: 9; or SEQ ID NO: 5 and SEQ ID NO: 9. In other examples, the subject is administered a composition including one or more "Sarbecovirus Region 2" polypeptides or nucleic acids encoding polypeptides selected from sequences with at least 95% sequence identity (such as at least 95%, at least 96%, at least 97%, at least 98%, at least 99%, or even 100% sequence identity) to SEQ ID NOs: 10, 13, and 14. In particular examples, the subject is administered a composition including polypeptides or nucleic acids encoding polypeptides as follows: SEQ ID NO: 10; or SEQ ID NO: 10 and SEQ ID NO: 13; or SEQ ID NO: 10, SEQ ID NO: 13, and SEQ ID NO: 14; or SEQ ID NO: 10 and SEQ ID NO: 14.

One or more of the disclosed polypeptides or nucleic acids encoding the polypeptides (including vectors including the nucleic acid) or disclosed compositions can be administered by any means known to one of skill in the art, e.g., either locally or systemically, such as by intramuscular, subcutaneous, intradermal, or intravenous injection, but even oral, nasal, or anal administration is contemplated. In one embodiment, administration is by subcutaneous or intramuscular injection. In other embodiments, administration is intranasal or inhaled. In still other embodiments, administration is oral.

To extend the time during which the disclosed polypeptides are available to stimulate a response, the polypeptide or a nucleic acid encoding the polypeptide can be provided as an implant, an oily injection, or as a particulate system. The particulate system can be a microparticle, a microcapsule, a microsphere, a nanoparticle, a nanocapsule, or similar particle. A particulate carrier based on a synthetic polymer has been shown to act as an adjuvant to enhance the immune response, in addition to providing a controlled release.

In one embodiment, a nucleic acid encoding a disclosed immunogenic polypeptide is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the nucleic acid is injected into muscle, although it can also be injected directly into other sites.

The amount of the disclosed immunogenic polypeptide, nucleic acid molecule encoding the immunogenic polypeptide, or vector including the nucleic acid molecule can vary depending upon the specific polypeptide(s), the route and protocol of administration, and the target population. An optimal amount for a particular composition can be ascertained by standard studies involving observation of responses in subjects (such as T cell responses).

In some embodiments, the immunogenic composition is administered in a single dose. In other embodiments, the immunogenic composition is administered as part of a prime-boost immunization protocol. In some examples, the same immunogenic composition is used as the prime dose and as the boost dose. It is also contemplated in some examples that the boost may be the same immunogen as another boost, or the prime. In other examples, a disclosed immunogenic composition is used as the prime dose, and a different coronavirus vaccine (such as a vaccine targeting another coronavirus protein) is administered as the boost dose. Alternatively a disclosed immunogenic composition is used as the boost dose, and a different coronavirus vaccine (such as a vaccine targeting a different coronavirus protein) is administered as the prime dose. In another example, the same immunogen is included in the prime and boost, but a different delivery system is used (for example, a different vector). It is contemplated that there can be several boosts, and that each boost can the same or different from each other and/or from the prime dose.

The prime and the boost can be administered as a single dose or multiple doses, for example, 1, 2, 3, 4, 5, 6 or more doses can be administered to a subject over days, weeks or months. In non-limiting examples, at least one boost is administered about 3-6 weeks following the prime (such as about 3 weeks, 4 weeks, 5 weeks, or 6 weeks later). Multiple boosts can also be given, such one to five, or more. Different dosages can be used in a series of sequential inoculations. For example, a relatively large dose in a primary inoculation and then a boost with relatively smaller doses. The immune response against the selected immunogen can be elicited by one or more inoculations of a subject.

In some embodiments, the subject is administered an adenovirus vector including a nucleic acid encoding one of the disclosed polypeptides. In some examples, the method includes administering a dose of about $10^5$ to about $10^{12}$ viral particles, such as about $10^5$ to about $10^7$ viral particles, about $10^6$ to about $10^8$ viral particles, about $10^7$ to about $10^8$ viral particles, about $10^8$ to about $10^{10}$ viral particles, about $10^9$ to about $10^{11}$ viral particles, or about $10^{10}$ to about $10^{12}$ viral particles. In some examples, the dose is about $1\times10^5$, about $5\times10^5$, about $1\times10^6$, about $5\times10^6$, about $1\times10^7$, about $5\times10^7$, about $1\times10^8$, about $5\times10^8$, about $1\times10^9$, about $5\times10^9$, about $1\times10^{10}$, about $5\times10^{10}$, about $1\times10^{11}$, about $5\times10^{11}$, or about $1\times10^{12}$ viral particles.

In other embodiments, the subject is administered an mRNA-lipid nanoparticle (LNP) composition encoding one of the disclosed polypeptides (see Section II). In some embodiments, the subject is administered about 1-100 μg of the mRNA-LNP (such as about 1-10 μg, about 5-15 μg, about 10-30 μg, about 20-40 μg, about 30-50 μg, about 40-60 μg, about 50-70 μg, about 60-80 μg, about 70-90 μg, or about 80-100 μg). In some examples, the dose is about 1 μg, about 2.5 μg, about 5 μg, about 7.5 μg, about 10 μg, about 12 μg, about 15 μg, about 20 μg, about 25 μg, about 30 μg, about 40 μg, about 50 μg, about 60 μg, about 70 μg, about 80 μg, about 90 μg, or about 100 μg mRNA-LNP.

In some embodiments, a disclosed polypeptide or nucleic acid is administered to the subject simultaneously with the administration of an adjuvant, for example administration of a composition that includes the polypeptide or nucleic acid and one or more adjuvants. In other embodiments, a disclosed polypeptide or nucleic acid is administered to the subject after the administration of an adjuvant and within a sufficient amount of time to elicit the immune response. In further embodiments, the subject is not administered an adjuvant.

Coronavirus (e.g., SARS-CoV-2) infection does not need to be completely inhibited for the disclosed methods to be effective. For example, eliciting an immune response can reduce or inhibit coronavirus infection by a desired amount, for example, by at least 10%, at least 20%, at least 30%, at least 40%, at least 50%, at least 60%, at least 70%, at least 80%, at least 90%, at least 95%, at least 98%, or even at least 100% (elimination or prevention of detectable infected cells), as compared to in the absence of immunization. In additional examples, coronavirus replication can be reduced or inhibited by the disclosed methods, for example, by at least 10%, at least 20%, at least 30%, at least 40%, at least 50%, at least 60%, at least 70%, at least 80%, at least 90%, at least 95%, at least 98%, or even at least 100% (elimination or prevention of detectable replication), as compared to in the absence of the immune response.

This disclosed immunogenic compositions can be used in combination with other immunogenic compositions or vaccines. In some embodiments, the disclosed immunogenic composition is used in combination (either simultaneously or sequentially) with a second coronavirus vaccine, including, a vaccine utilizing a different coronavirus protein immunogen.

EXAMPLES

The following examples are provided to illustrate certain particular features and/or embodiments. These examples should not be construed to limit the disclosure to the particular features or embodiments described.

Example 1

Identification of Conserved Regions of SARS-CoV-2 and Sarbecoviruses

An alignment of the full proteome of several hundred Sarbecoviruses was created, and then this was reduced to a set of 83 viruses that were representative of the diversity (FIG. 1). All overlapping 9-mers throughout the proteome were used to represent potential T Cell epitopes, and 9-mer coverage by the Wuhan reference strain (GenBank® Accession No. NC_045512) and also by Epigraphs were used to define the boundaries of the most conserved area.

Figure 2:
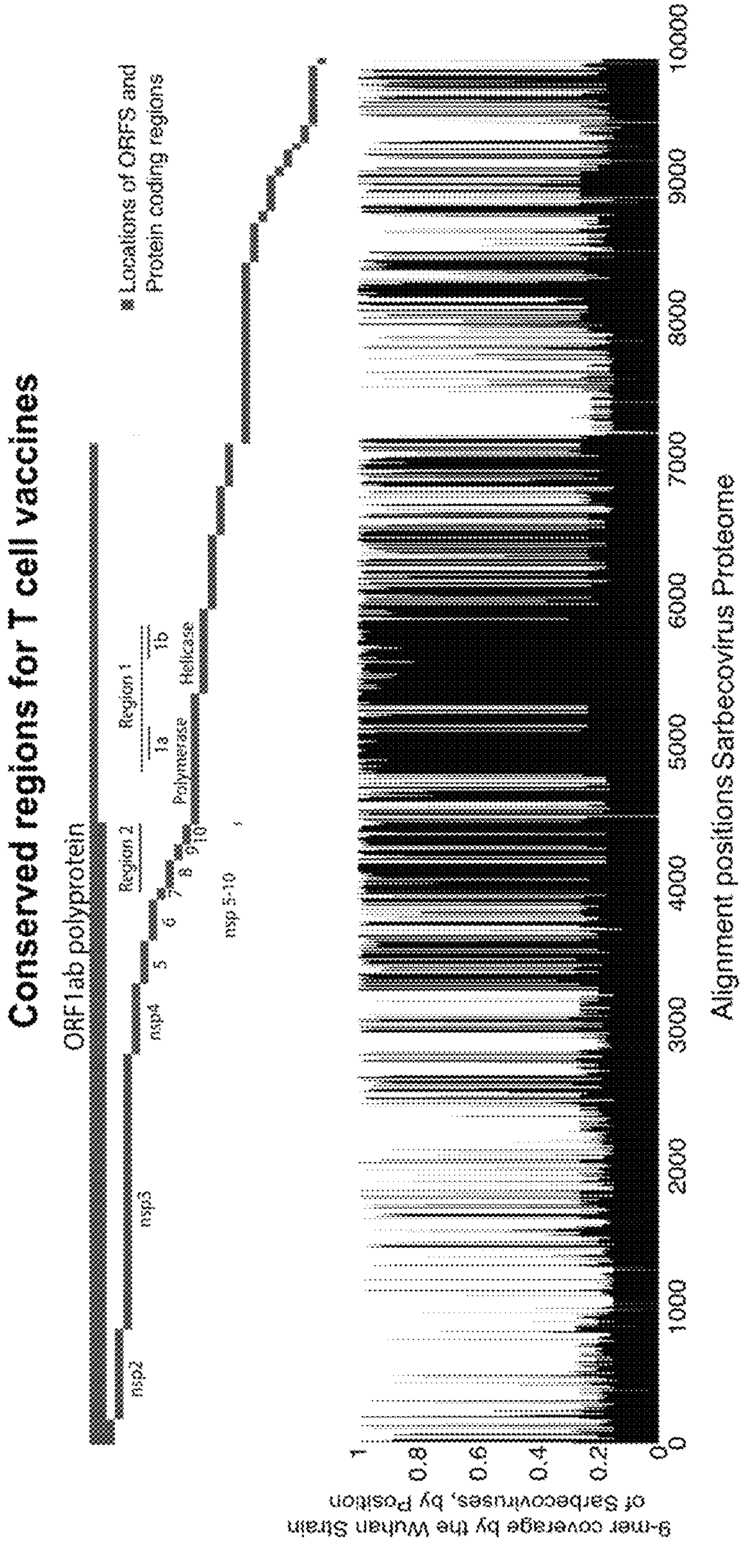
FIG. 2 is a schematic diagram illustrating 9-mer coverage in conserved regions of the *betacoronavirus* proteome. At the top is a schematic of all ORFs, with key proteins labeled. The frequency of perfect matches of each 9-mer to the Wuhan reference strain (GenBank® Accession No. NC-045512) is shown (bottom). Bars approaching 1 indicate nearly invariant 9-mers that match SARS-CoV-2, and dense clustering of these indicates the most conserved regions.
Figure 3:
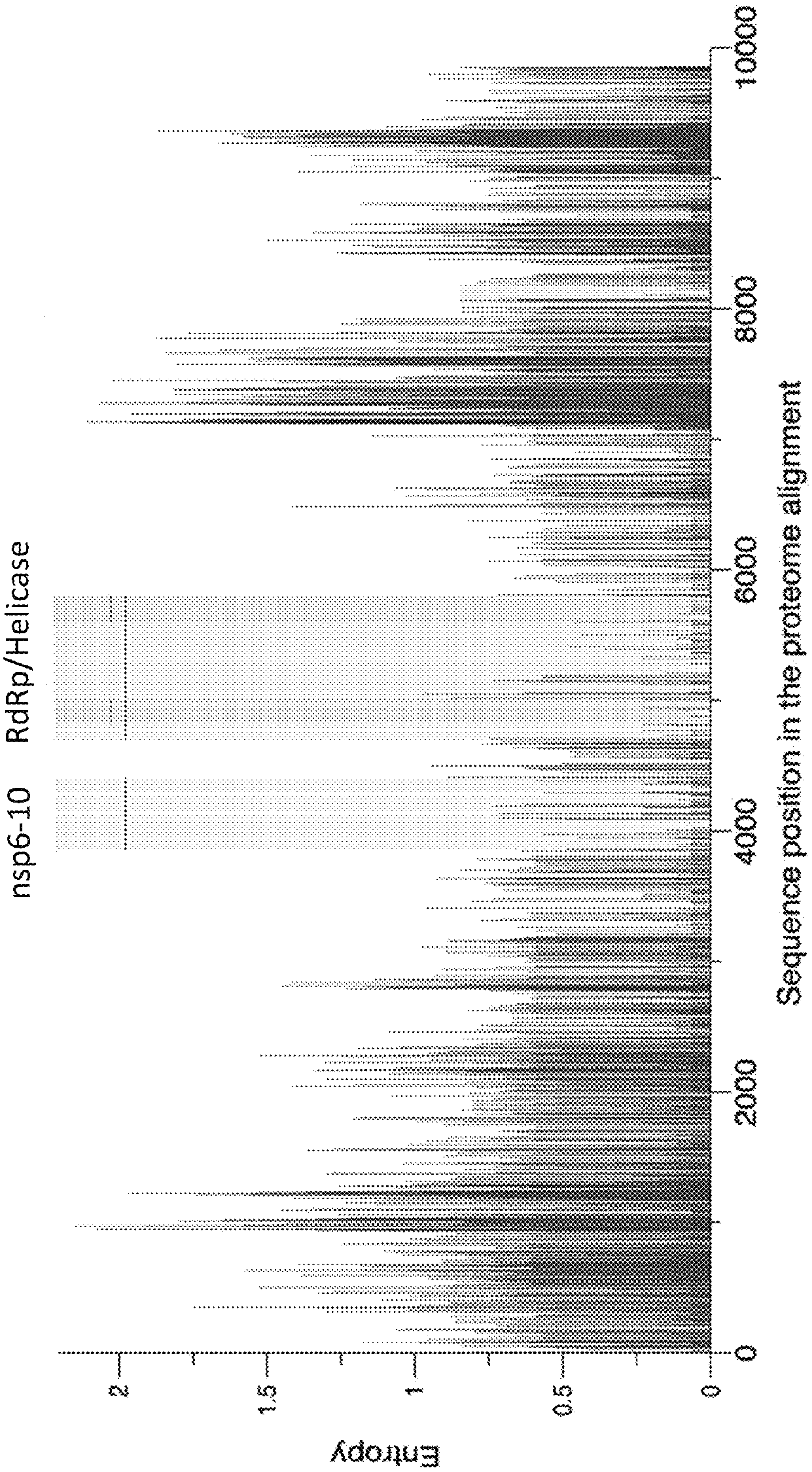
FIG. 3 is a graph showing positional entropy of amino acids in Sarbecovirus proteome alignment.

Adenovirus delivery systems are constrained to have protein inserts no more than 1200 amino acids long, so a region of the proteome of Sarbecoviruses with the greatest conservation spanning less than that upper bound in length, referred to herein as Region 1, was identified. 9-mers are stretches of 9 contiguous amino acids that are used as a surrogate for potential T cell epitopes. Epigraphs were generated to initially explore the potential for 9 mer coverage full proteome used to identify the most conserved regions from a linear CTL epitope perspective (FIG. 2) (Theiler et al., *Sci. Rep.* 6:33987, 2016; Theiler & Korber Stat Med. 2018 Jan. 30; 37(2):181-194). Per position entropy scores were used to aid in defining precise boundaries of the conserved region (FIG. 3). This yielded a protein fragment of 1,094 amino acids spanning positions of 4692-5785 in ORF1ab (positions 300-932 in RNA-dependent RNA polymerase, plus positions 1-461 in Helicase). The most conserved regions in terms of 9-mer coverage within the larger protein fragment were two stretches, Region 1a (positions 407-610 in RNA-dependent RNA polymerase), Region 1b (positions 261-461 in Helicase). The second most conserved region in the Sarbecovirus proteome alignment, positions 3848-4387 in ORF1ab, spanning the end nsp6, all of nsp7-9, and the beginning of nsp10, referred to herein as Region 2, was also identified.

Example 2

Evaluation of Immunogenicity of Adenovirus Vector Delivered SARS-CoV2 Conserved Region Immunogen Mice were immunized as shown in Table 2. A boost was administered at day 28, and samples were collected for analysis at days 28 and 56. S.pp is a stabilized Spike protein. Topt is SEQ ID NO: 1.

TABLE 2

Immunogenicity Study Plan

| Group | Vaccine Regimen |
| --- | --- |
| 1 | Ad26.S.pp |
| 2 | Ad26.S.pp (prime)/RhAd52.S.pp (boost) |
| 3 | Ad26.Topt |
| 4 | Ad26.Topt (prime)/RhAd52.Topt (boost) |
| 5 | Ad26.Topt (prime)/RhAd52.S.pp (boost) |
| 6 | PBS |

Figure 4:
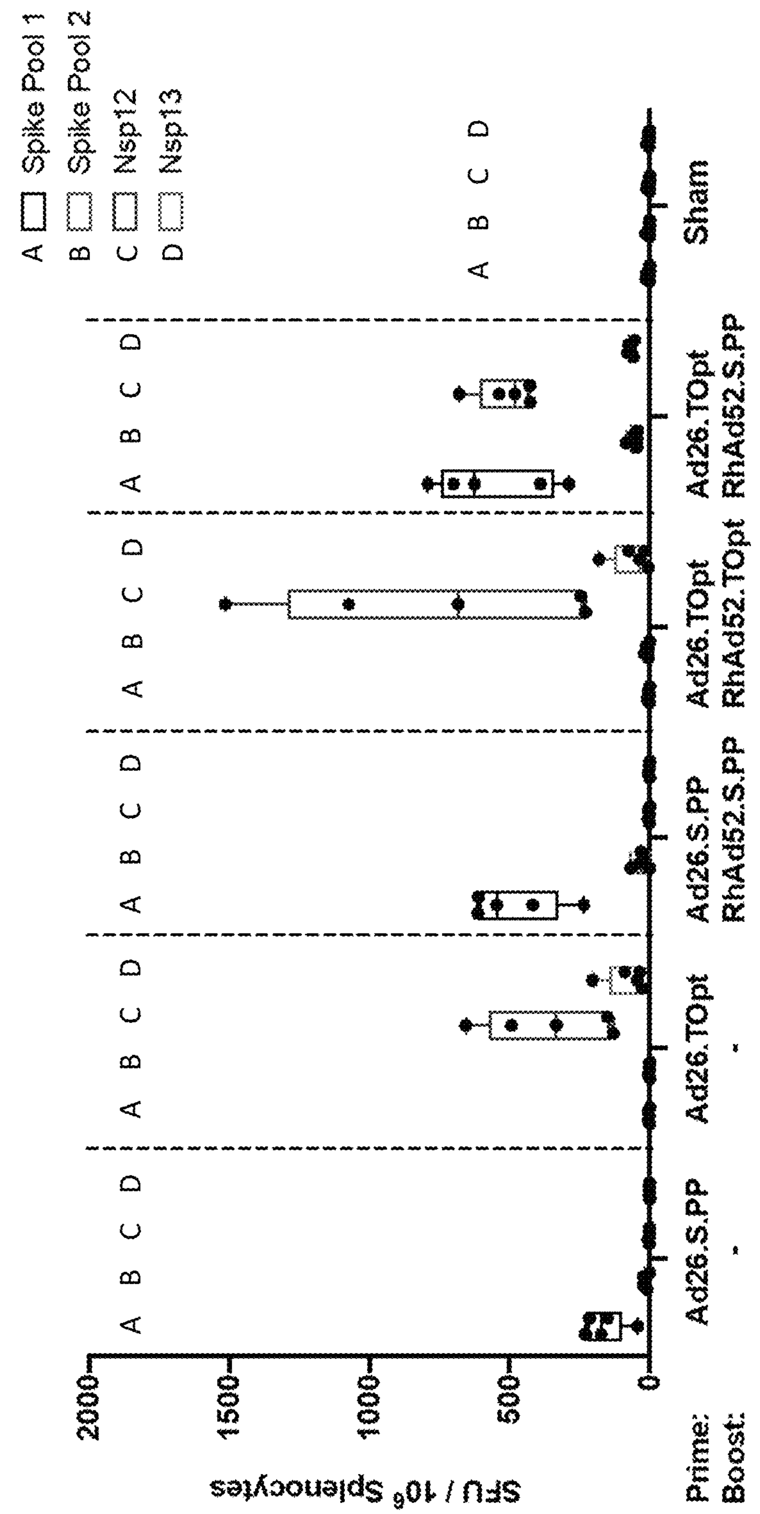
FIG. 4 illustrates interferon γ (IFNγ) response in splenocytes to the indicated proteins in mice vaccinated with the indicated protocols.
Figure 5A:
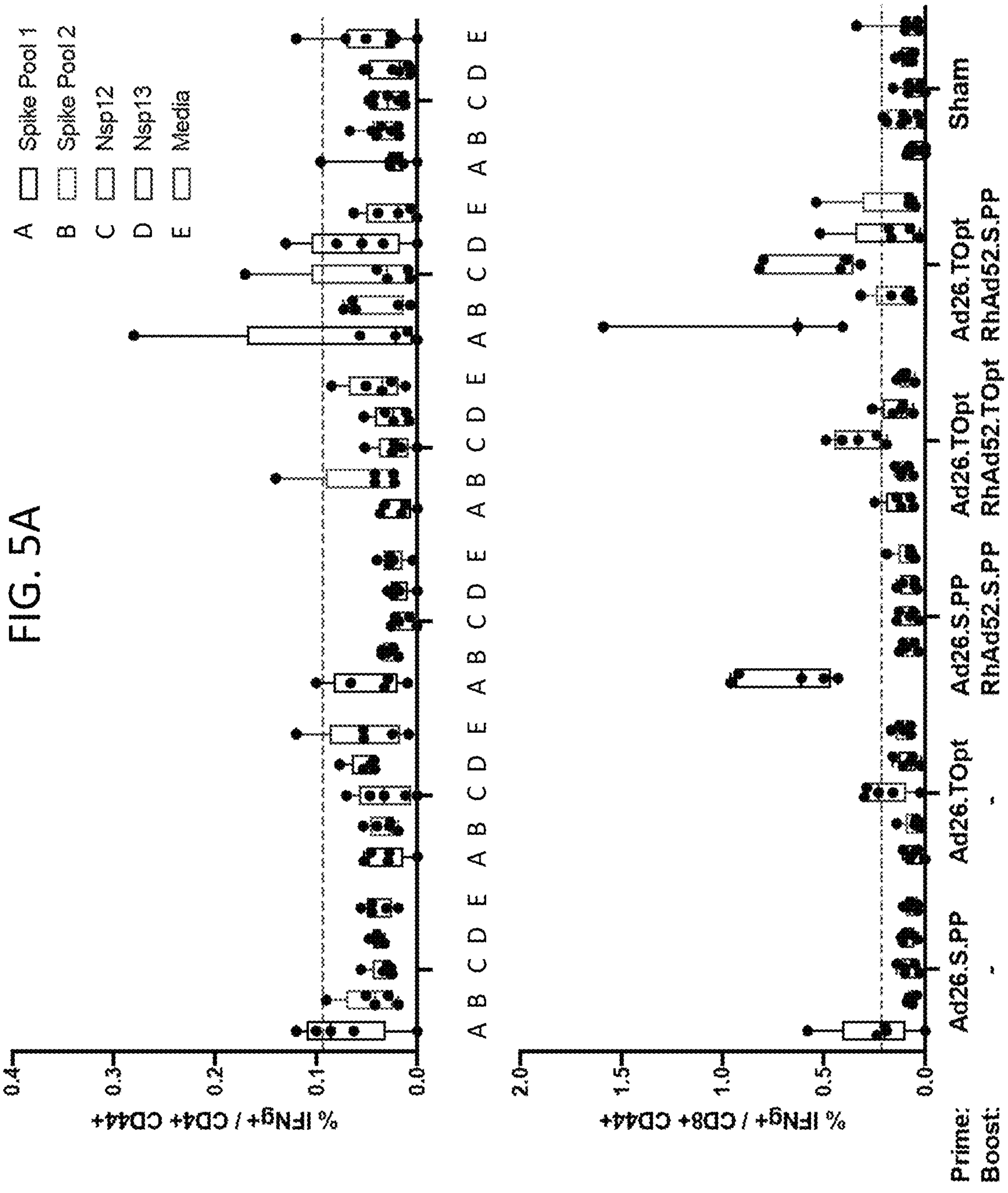
FIGS. 5A and 5B show intracellular IFNγ staining in lung (FIG. 5A) and spleen (FIG. 5B) in response to the indicated proteins in mice vaccinated with the indicated protocols.
Figure 5B:
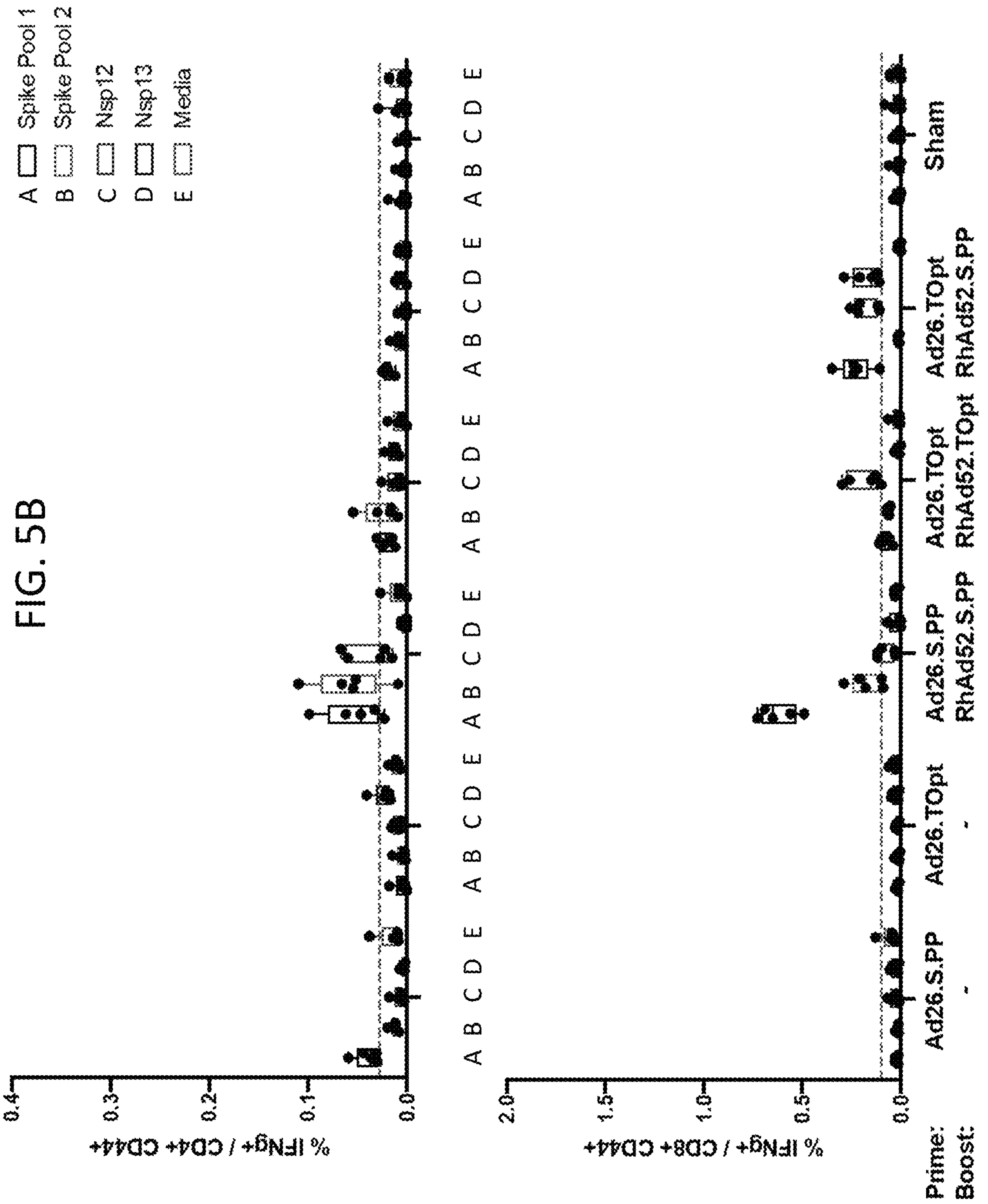

Interferon γ (IFNγ) in spleen was analyzed by ELIspot assay (FIG. 4) and IFNγ intracellular cytokine staining was analyzed in lung (FIG. 5A) and spleen (FIG. 5B).

Example 3

Figures 6A, 6B:
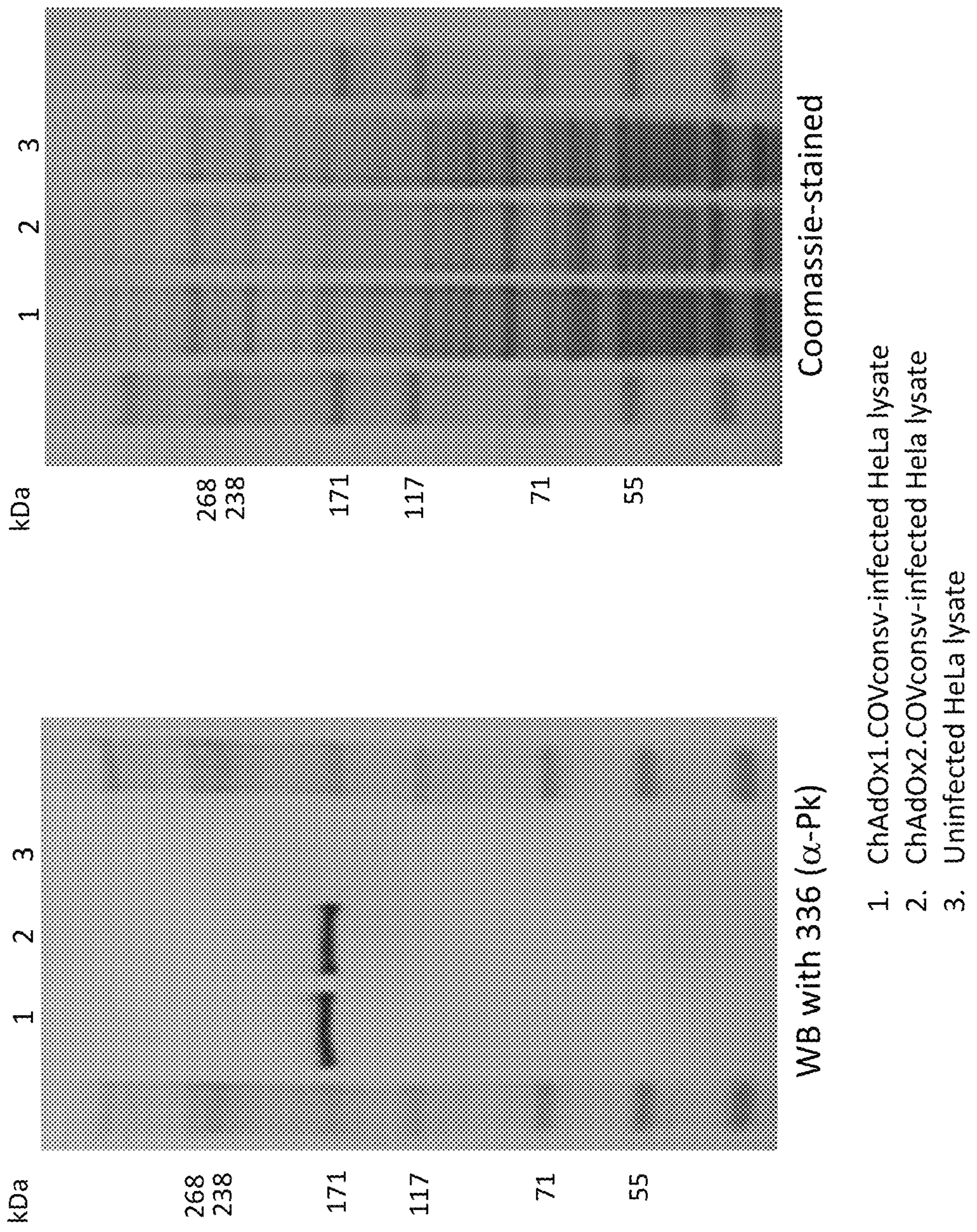
FIGS. 6A and 6B show expression of conserved region protein SEQ ID NO: 18 in 6wp HeLa cells infected with ChAdOx1·COVconsv or ChAdOx2·COVconsv. Samples were run on 3-8% Tris Acetate gel and analysed by Western blot (FIG. 6A) and Coomassie staining (FIG. 6B). Left panel shows size marker ladder. COVconsv theoretical size=182.57 kDa. Note that COVconsv has a C-terminal tag Pk recognized by monoclonal antibody 336.

Evaluation of Immunogenicity of Chimpanzee Adenovirus Vector Delivered SARS-CoV2 Conserved Region Immunogen 6wp HeLa cells were infected with MOI 10 ($1\times10^7$ IU) of ChAdOx1.COVconsv or ChAdOx2·COVconsv in 1 ml volume for 2 h. COVconsv has the amino acid sequence of SEQ ID NO: 18. D10 was added and incubated for 24 h. Cells were lysed in 200 ml M-PER+HALT. Samples (10 μl inclusive of 4× sample buffer and 10× reducing agent) were run on 3-8% Tris Acetate gel and analysed by Western blot and Coomassie staining (FIGS. 6A and 6B). Full-size proteins were readily expressed from both vaccines were readily detectable. Note that the COVconsv protein has a Pk tag at its C-terminus recognized by mAb 336, which facilitated the protein detection. Mice were immunized intramuscularly with one dose of ChAdOx1·COVconsv. A group of 3 BALB/c mice were immunized i.m. with $10^8$ infectious units and sacrificed 9 day later. IFNγ ELISpot assay was performed on pooled splenocytes using 201 peptides 18/10 from across the COVconsv sequence.

Figure 7:
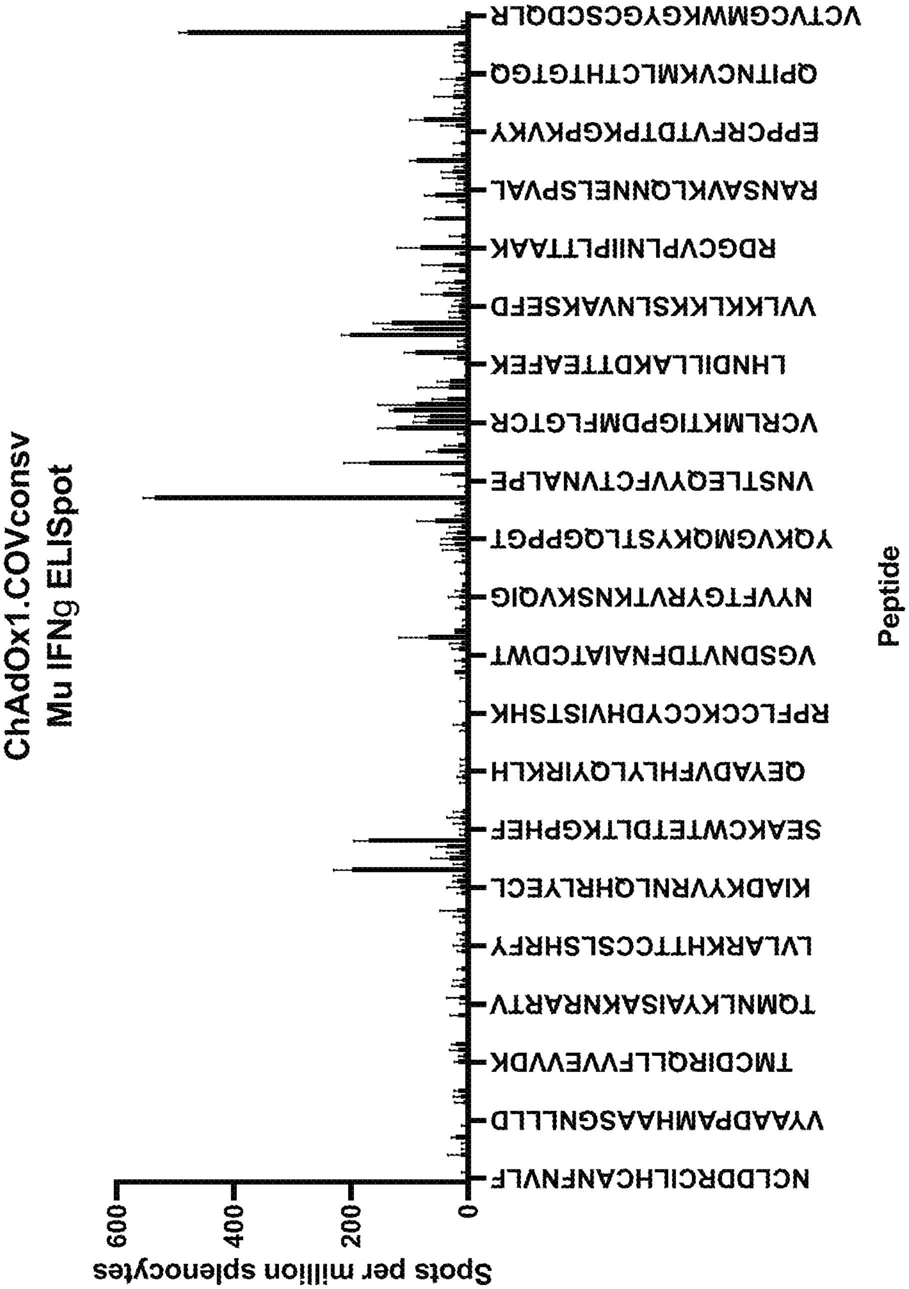
FIG. 7 is a graph showing IFNγ ELISpot assay results of immune BALB/c splenocytes tested against 18-mer peptides overlapping by 11 amino acids spanning the entire the COVconsv (region 1 and region 2) immunogen 9 days after a single intramuscular vaccination. Every $10^{th}$ peptide is listed.
Figure 8A:
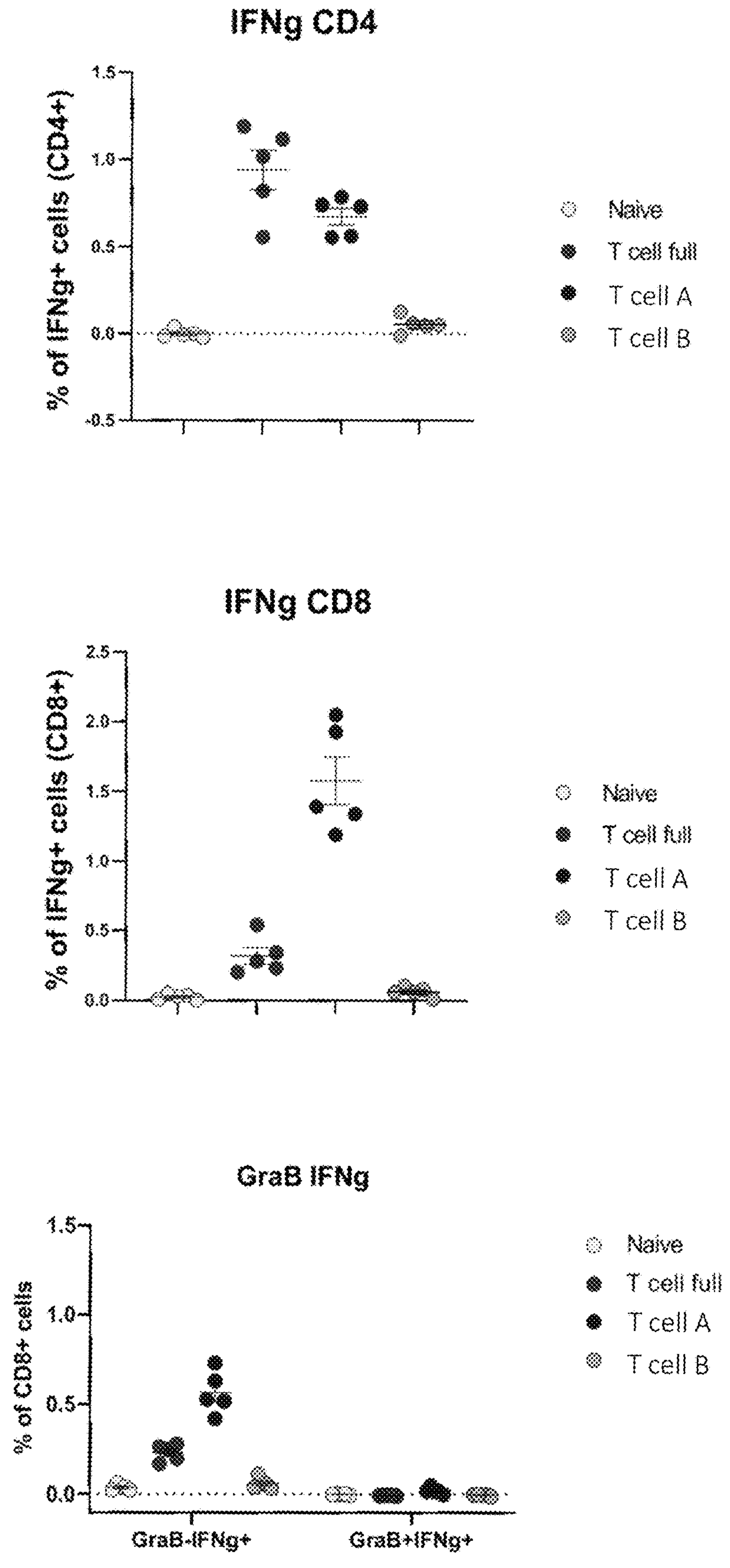
Figure 8B:
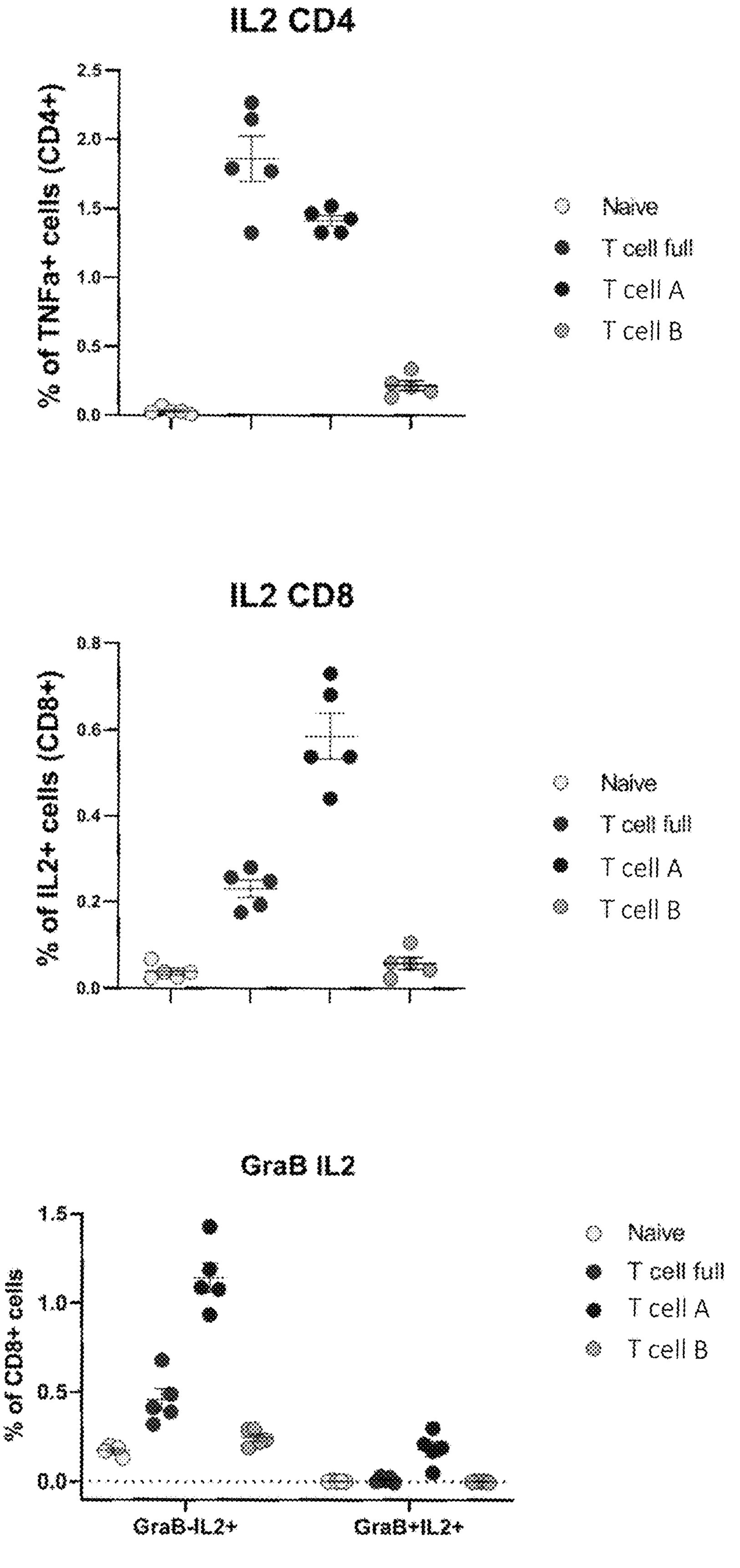
Figure 8C:
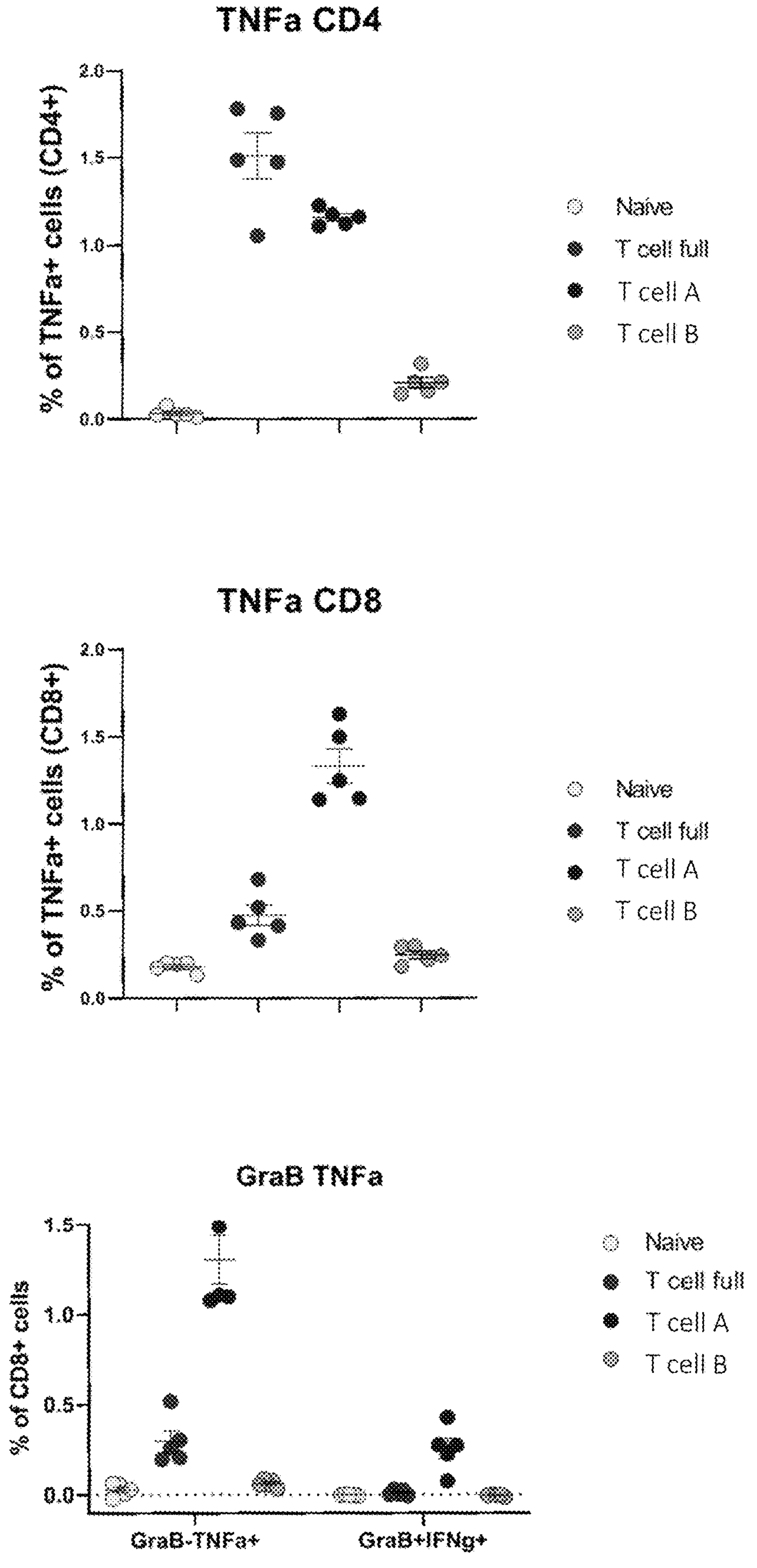
Figure 8D:
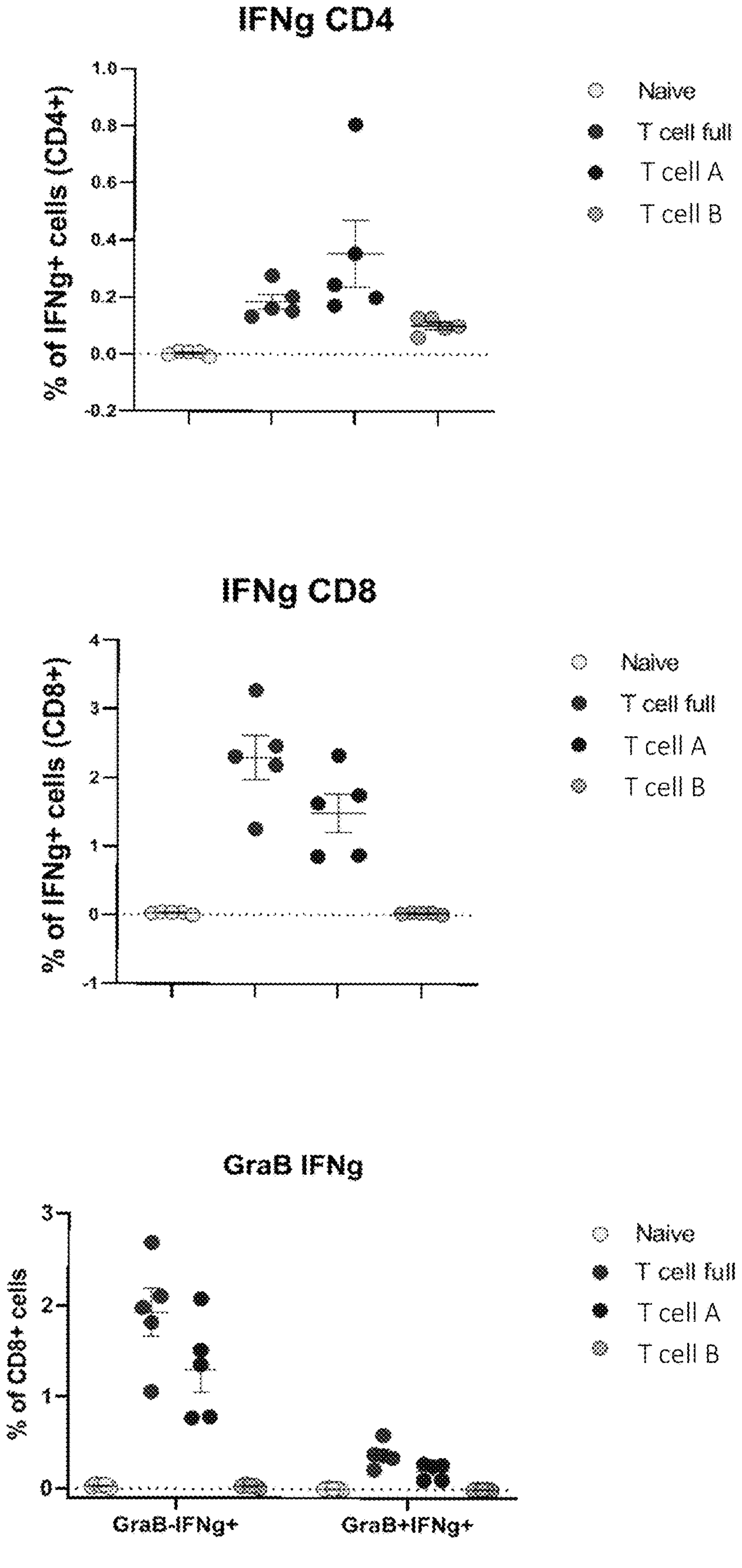
Figure 8F:
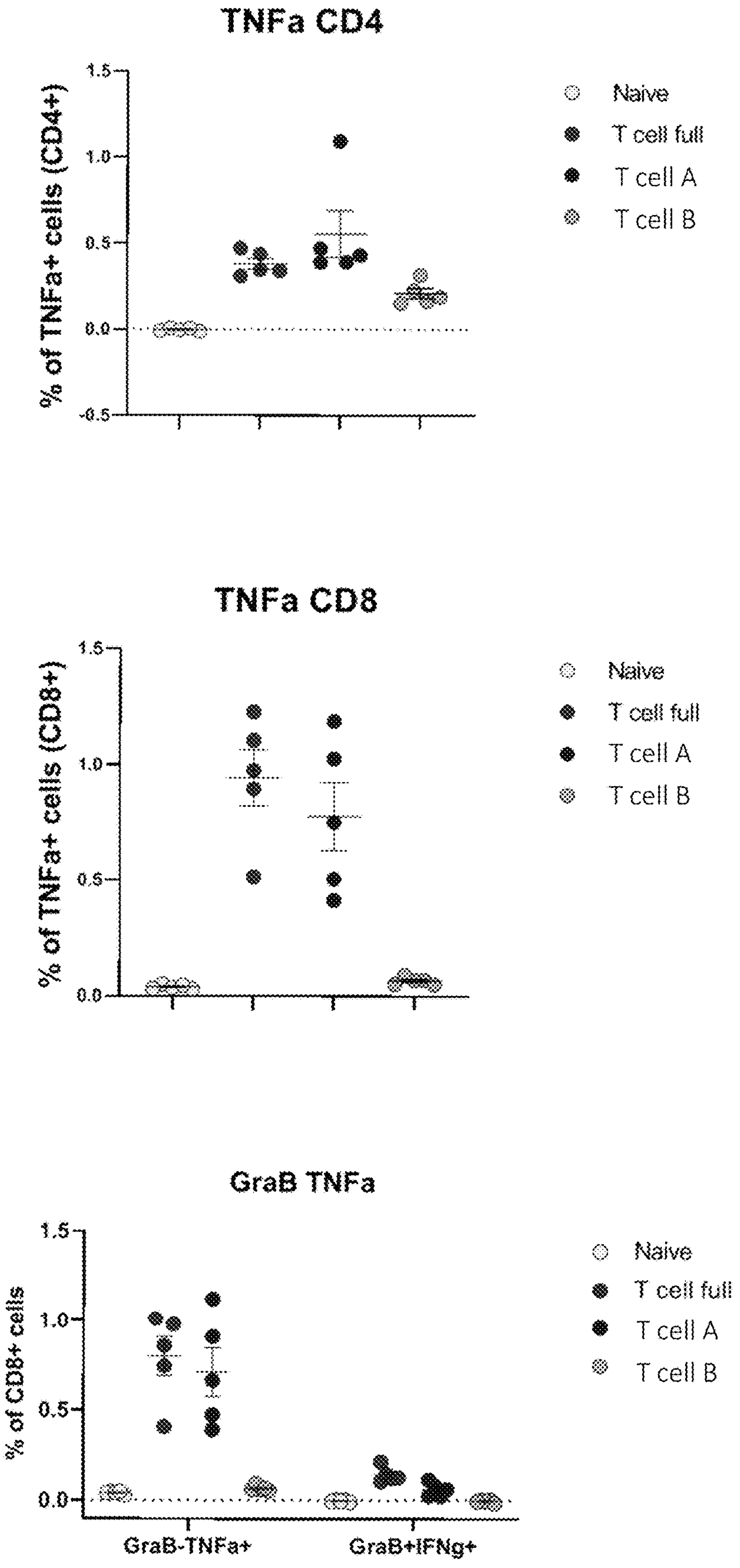

A broad T cell response was induced dominated by two strong specificities and further five medium strong peptides (FIG. 7). These T cell responses can complement antibodies recognizing other coronavirus proteins elicited by currently available vaccines, and may further improve virus control and perhaps help resolve long COVID symptoms.

Example 4

Evaluation of Immunogenicity of SARS-CoV2 Conserved Region Immunogen Using Lipid Nanoparticle mRNA Delivery Balb/c or C57/B16 mice (8-10 weeks old) were immunized with nucleoside-modified mRNA-LNP vaccines encoding conserved regions of CoVs (SEQ ID NOs: 15-17). Ten days later, spleen cells were obtained and stimulated with peptide pools encompassing the immunogen used to vaccinate. Multicolor flow cytometry was performed. Data show CD4+ and CD8+ T cell responses (FIGS. 8A-8F).

Example 5

Evaluation of Efficacy of Adenovirus Delivery in SARS-CoV-2 Mouse Adapted Virus Model This example describes particular methods that can be used to evaluate vaccine efficacy. However, one skilled in the art will appreciate that methods that deviate from these specific methods can also be used. In addition, alternative coronavirus polypeptides (such as one or more of the polypeptides described herein) can be encoded by the adenovirus construct(s).

Figure 9:
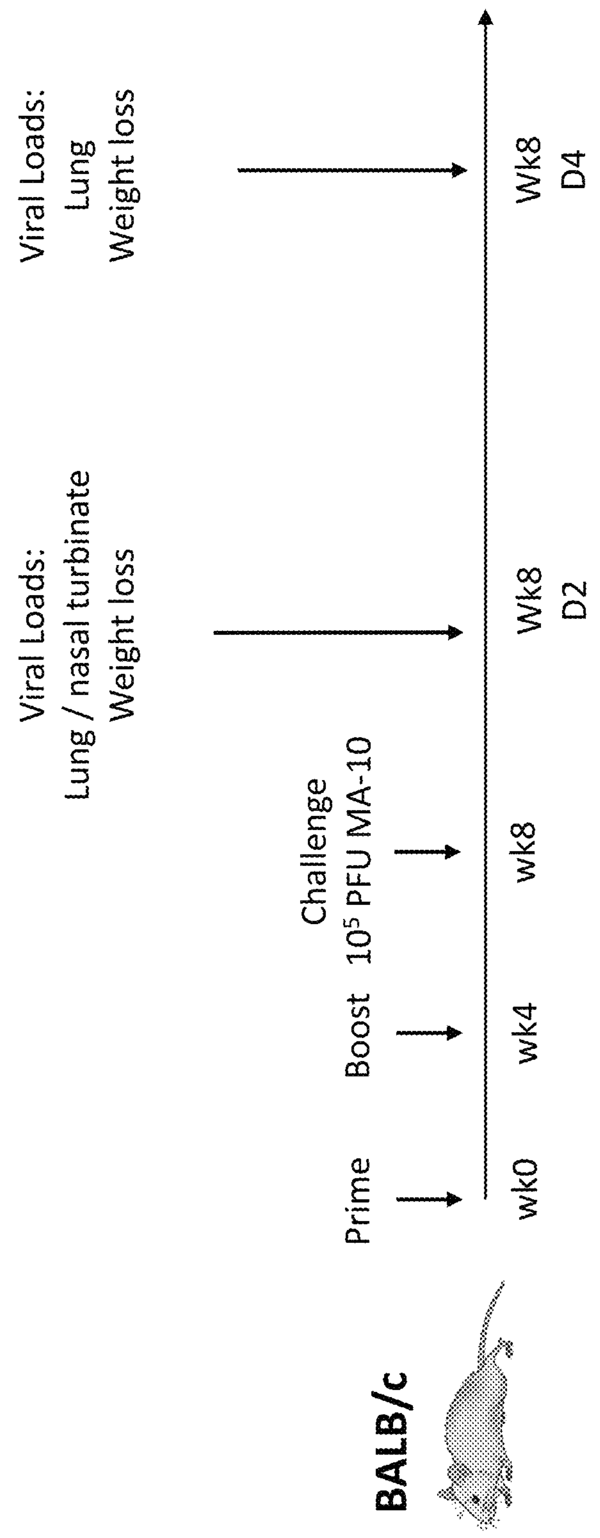
FIG. 9 is a schematic diagram showing an exemplary protocol for testing a disclosed immunogenic composition.

In some examples, adenovirus delivery of a conserved region polypeptide is tested in a mouse-adapted model of SARS-CoV-2. An exemplary protocol is shown in FIG. 9. The vaccination regimen is provided in Table 3. The adenovirus vectors are as described in Example 2.

TABLE 3

Vaccination regimen

| Group | Week 0 (prime) | Week 4 (boost) |
|---|---|---|
| 1 | Sham | Sham |
| 2 | $10^9$ vp RhAd52.S.PP | $10^9$ vp RhAd52.S.PP |
| 3 | — | $10^7$ vp RhAd52.S.PP |
| 4 | $10^7$ vp RhAd52.S.PP | — |
| 5 | $10^9$ vp RhAd52.TOpt | $10^9$ vp RhAd52.Topt |
| 6 | $10^7$ vp RhAd52.S.PP + 10^9 vp RhAd52.TOpt | $10^9$ vp RhAd52.TOpt |
| 7 | $10^9$ vp RhAd52.TOpt | $10^7$ vp RhAd52.S.PP + 10^9 vp RhAd52.TOpt |

Four weeks following the boost, mice are challenged with SARS-CoV-2 intranasally and assessed for viral load and weight loss 2 days and 4 days later. A decrease in viral load or weight loss compared to a control indicates efficacy of the immunization.

Example 6

Epigraph Sequence Development

Initially it was important to resolve that the regions of high potential epitope identified in Example 1 would be immunogenic using the COVID-19 vaccine delivery strategies; this proved to be the case using the SARS-CoV-2 ancestral sequence as a prototype (Examples 2-4). As even the most conserved regions of the virus show some variability, epigraph sequences were designed spanning Region 1 and Region 2. These Epigraphs were designed serially using the SARS-CoV-2 sequence as a baseline, and provide complementary sequences to provide 9-mer coverage using either the Sarbecovirus alignment for a pan-Sarbecovirus vaccine (FIG. 1), or a global alignment from GISAID for a SARS-CoV-2 vaccine that best covers known pandemic diversity based on ~461,092 sequences sampled from GISAID on Mar. 24, 2021. These epigraphs can be utilized in a combination of 2 or 3 vaccine antigens to prevent escape in SARS-CoV-2 infections and increase breadth of coverage: either (i) the Wuhan reference plus one epigraph, for a bivalent vaccine, or (ii) the Wuhan reference plus two epigraphs for a trivalent vaccine.

In the sequences provided herein, the first epigraph is complementary to the ancestral Wuhan form, and is an artificial sequence designed to provide optimal 9-mer diversity coverage of the input sequence alignment when combined with the Wuhan form; the second epigraph is complementary to the combination of the first two, and provides potentially optimal coverage for a trivalent vaccine.

Example 7

Region 1 Epigraphs

Epigraphs were designed to best cover known global SARS-CoV-2 9-mer diversity in conserved region 1 (SEQ ID NO: 5), as maintained in GISAID, based on the Mar. 24, 2021, full proteome SARS-COV-2 global alignment. The cov.lanl.gov FULL.ORFlab.protein.Human.fasta alignment on that day included 461,092 sequences.

Figure 10:
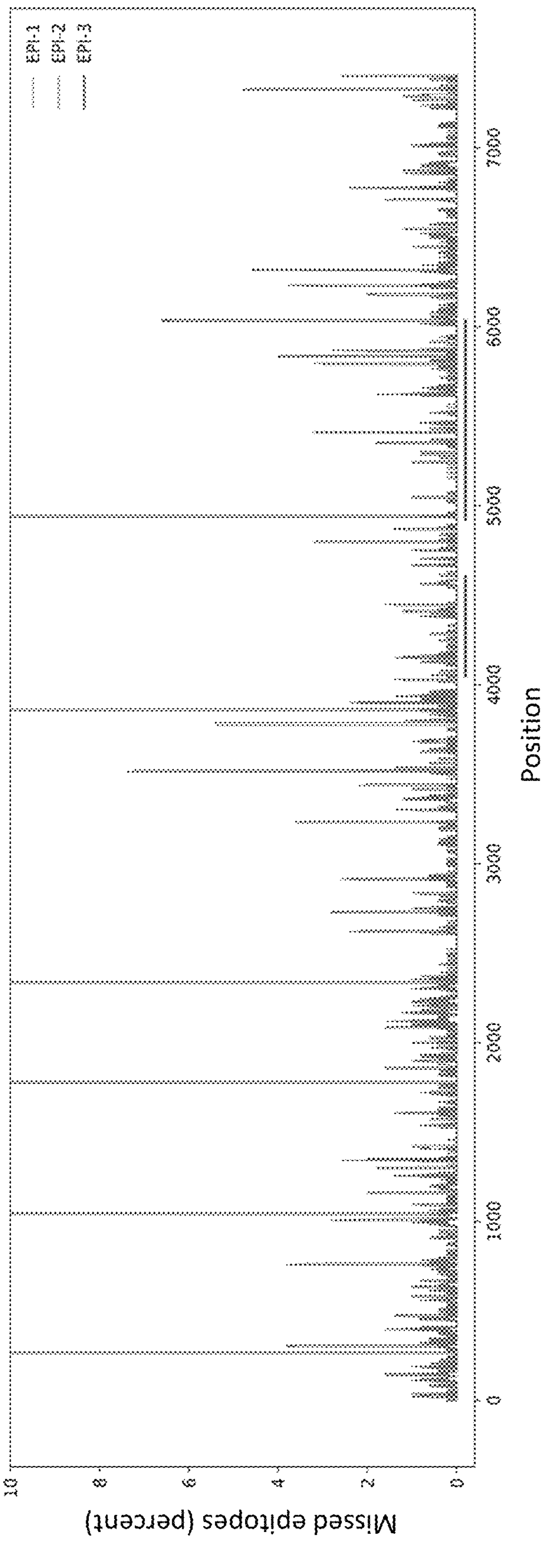
FIG. 10 is a plot showing the percent of missed 9-mers, or potential T cell epitopes, using the Wuhan reference strain (GenBank® Accession No. NC_045512) alone (EPI-1; GenBank® Accession No. NC_045512), or using the combination of the Wuhan sequence plus one epigraph (EPI-2; SEQ ID NO: 6) or plus two epigraphs (EPI-3; SEQ ID NO: 6 and SEQ ID NO: 7), spanning the lab polyprotein. EPI-2 provides a substantial increase in coverage. Region 2 is very highly conserved to date among pandemic strains. Region 1, despite being the most conserved region across Sarbecoviruses, has both some very highly conserved regions and some modestly conserved regions.

Two epigraphs were selected: Region 1 SARS-CoV-2-EG-2.1 (SEQ ID NO: 6) and Region 1 SARS-CoV-2-EG-2.2 (SEQ ID NO: 7). The percentage of missed 9-mers (potential T cell epitopes) using SEQ ID NO: 5 alone, SEQ ID NO: 5 plus SEQ ID NO: 6, or all of SEQ ID NOs: 5-7 (FIG. 10). The combination of SEQ ID NO: 5 and SEQ ID NO: 6 provided a substantial increase in coverage; addition of SEQ ID NO: 7 provided an additional improvement (Table 4), with less than 0.1% of missed 9-mers (>99.9% coverage). An alignment of SEQ ID NOs: 1, 6, and 7 is shown in FIG. 11.

TABLE 4

Potential T cell epitopes missed by combinations of Region 1 SARS-CoV2 polypeptides (percentage) across SARS-CoV-2

| | All (A) | Positions 4044-4605 (B) | Positions 4921-6041 (C) | All except B and C |
|---|---|---|---|---|
| Region 1 | 0.5959 | 0.2750 | 1.1459 | 0.5168 |
| Region 1 + Region 1 SARS-CoV-2-EG-2.1 | 0.1397 | 0.1177 | 0.0904 | 0.1518 |

TABLE 4-continued

| Potential T cell epitopes missed by combinations of Region 1 SARS-CoV2 polypeptides (percentage) across SARS-CoV-2 | All (A) | Positions 4044-4605 (B) | Positions 4921-6041 (C) | All except B and C |
|---|---|---|---|---|
| Region 1 + Region 1 SARS-CoV-2-EG-2.1 + Region 1 SARS-CoV-2-EG-2.2 | 0.0931 | 0.0683 | 0.0584 | 0.1026 |

Figure 12:
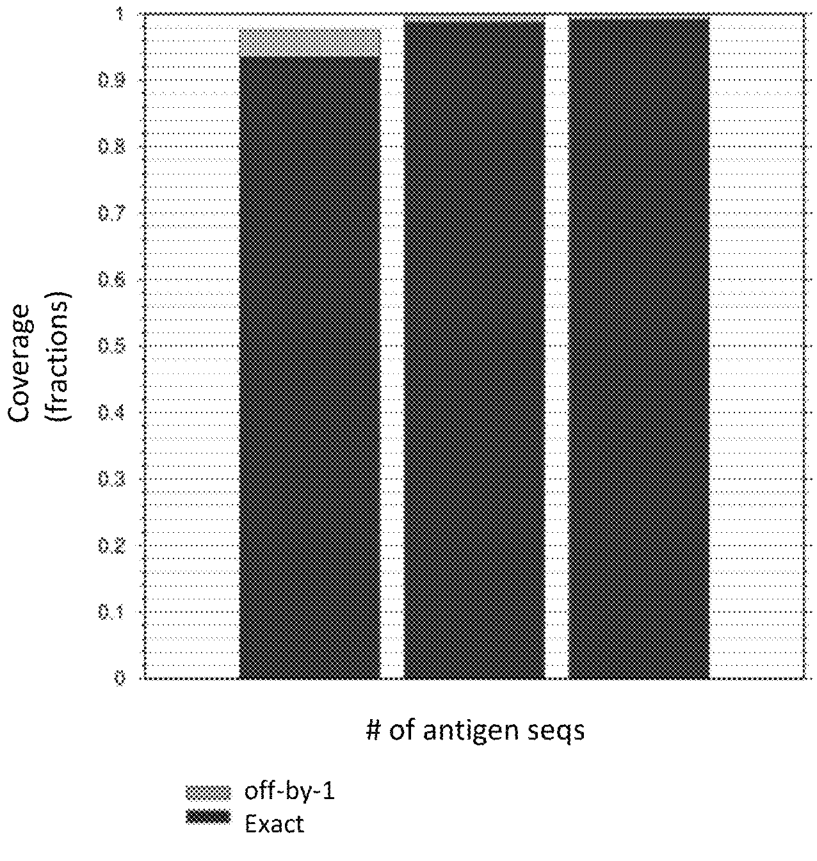
FIG. 12 is a graph showing coverage of pan-Sarbecovirus Region 1 of Wuhan alone (SEQ ID NO: 5, left), Wuhan Region 1 plus Region 1 SARBECO-EG-2.1 (SEQ ID NO: 8, center), and Wuhan Region 1 plus Region 1 SARBECO-EG-2.1, and Region 1 SARBECO-EG-2.2 (SEQ ID NO: 9, right).

Region 1 is extremely conserved among Sarbecoviruses, such that the Wuhan strain alone captures much of the diversity in the Sarbecovirus aligned sequences (FIG. 1). A single epigraph (SEQ ID NO: 8) provided additional coverage given the diversity of the input sample; the addition of the second epigraph (SEQ ID NO: 9) provides an incremental benefit (Table 5 and FIG. 12). An alignment of SEQ ID NOs: 1, 8, and 9 is shown in FIG. 13.

TABLE 5

| Sarbecovirus coverage for Region 1 | Coverage (exact) | Coverage (offby ≤1) |
|---|---|---|
| Wuhan (SEQ ID NO: 5) | 0.935196 | 0.975149 |
| Wuhan plus epigraph 1 (SEQ ID NO: 5 and SEQ ID NO: 8) | 0.987062 | 0.999574 |
| Wuhan plus epigraphs 1 and 2 (SEQ ID NOs: 5, 8, and 9) | 0.990941 | 0.999574 |

Example 8

Region 2 Epigraphs

Figure 14:
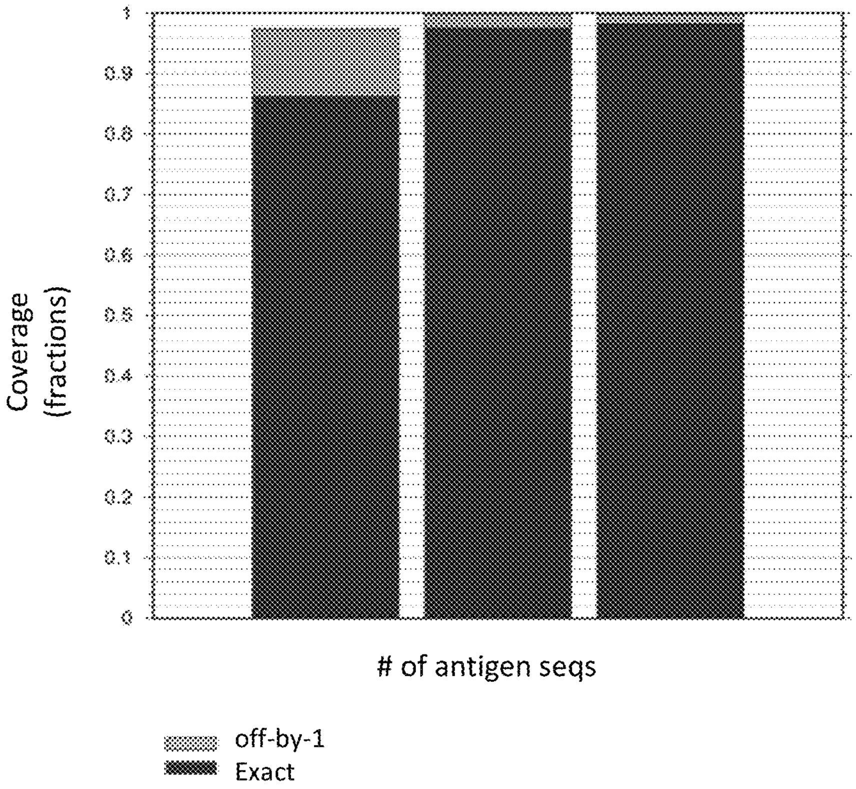
FIG. 14 is a graph showing coverage of pan-Sarbecovirus Region 2 of Wuhan alone (SEQ ID NO: 10, left), Wuhan Region 2 plus Region 2 SARBECO-EG-2.1 (SEQ ID NO: 13, center), and Wuhan Region 2 plus Region 2 SARBECO-EG-2.1, and region 2 SARBECO-EG-2.2 (SEQ ID NO: 14, right).

Region 2 was the second most conserved long stretch in the Sarbecovirus proteome. It was defined to be ~600 amino acids, which is compatible with RNA (such as mRNA-LNP) delivery systems. Epigraphs to best cover known global SARS-CoV-2 9-mer diversity and in Sarbecoviruses were designed as described above. The SARS-CoV-2 epigraphs are SEQ ID NOs: 11 and 12, and pan-Sarbecovirus epigraphs are SEQ ID NOs: 13 and 14. Table 6 and FIG. 14 summarize the Sarbecovirus coverage for Region 2 provided by the Wuhan reference sequence (SEQ ID NO: 10), and one or two of the pan-Sarbecovirus epigraphs. Alignments of the sequences are shown in FIGS. 15 and 16.

TABLE 6

| Sarbecovirus coverage for Region 2 | Coverage (exact) | Coverage (offby ≤1) |
|---|---|---|
| Wuhan (SEQ ID NO: 10) | 0.862376 | 0.974106 |
| Wuhan plus epigraph 1 (SEQ ID NO: 10 and SEQ ID NO: 13) | 0.975516 | 0.996945 |
| Wuhan plus epigraphs 1 and 2 (SEQ ID NOs: 10, 13, and 14) | 03982260 | 0.998355 |

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. An immunogenic composition comprising:

one or more polypeptides comprising the amino acid sequence of any one of SEQ ID NOs:5-7, or a nucleic acid encoding the one or more polypeptides; and a pharmaceutically acceptable carrier.

2. The immunogenic composition of claim 1, wherein the one or more polypeptides comprise:

SEQ ID NO: 6; or

SEQ ID NO: 5 and SEQ ID NO: 6; or

SEQ ID NO: 6 and SEQ ID NO: 7; or

SEQ ID NO: 5, SEQ ID NO: 6, and SEQ ID NO: 7.

3. The immunogenic composition of claim 1, wherein the nucleic acid is an mRNA and the mRNA is formulated in a lipid nanoparticle, and wherein the lipid nanoparticle comprises ALC-0315.

4. The immunogenic composition of claim 1, wherein the one or more polypeptides comprise two or more polypeptides, and at least one of the two or more polypeptides further comprise SEQ ID NO: 1.

5. The immunogenic composition of claim 4, wherein at least one of the two or more polypeptides comprise SEQ ID NO: 6.

6. The immunogenic composition of claim 4, wherein the two or more polypeptides comprise:

SEQ ID NO: 1 and SEQ ID NO: 5; or

SEQ ID NO: 1 and SEQ ID NO: 6; or

SEQ ID NO: 1 and SEQ ID NO: 7; or

SEQ ID NO: 1, SEQ ID NO: 5, and SEQ ID NO: 6; or

SEQ ID NO: 1, SEQ ID NO: 5, and SEQ ID NO: 7; or

SEQ ID NO: 1, SEQ ID NO: 6, and SEQ ID NO: 7.

7. A vector, wherein the vector comprises a nucleic acid sequence encoding any one of SEQ ID NOs: 5-7.

8. The vector of claim 7, wherein the vector is an adenovirus vector.

9. The vector of claim 8, wherein the adenovirus vector is an Ad5, Ad26, Ad35, or Ad52 adenovirus vector or a ChAdO×1 or ChAdO×2 adenovirus vector.

10. A method of eliciting an immune response to a coronavirus in a subject, comprising administering to the subject the immunogenic composition of claim 1, thereby eliciting an immune response to the coronavirus.

11. The method of claim 10, wherein the one or more polypeptides of the immunogenic composition comprise:

SEQ ID NO: 6; or

SEQ ID NO: 5 and SEQ ID NO: 6; or

SEQ ID NO: 6 and SEQ ID NO: 7.

12. The method of claim 10, wherein the immunogenic composition comprises the nucleic acid sequence encoding the one or more polypeptides, and the nucleic acid is mRNA.

13. The method of claim 12, wherein the mRNA is formulated in a lipid nanoparticle, and wherein the lipid nanoparticle comprises ALC-0315.

14. The method of claim 10, wherein the immunogenic composition comprises the nucleic acid sequence encoding the one or more polypeptides, and administering the nucleic acid comprises administering an adenovirus vector comprising the nucleic acid.

15. The method of claim 14, wherein the adenovirus vector is an Ad5, Ad26, Ad35, or Ad52 adenovirus vector or a ChAdOx1 or ChAdOx2 adenovirus vector.

* * * * *

SEQUENCE LISTING

```
<160> NUMBER OF SEQ ID NOS: 18

<210> SEQ ID NO 1
<211> LENGTH: 1094
<212> TYPE: PRT
<213> ORGANISM: Artificial Sequence
<220> FEATURE:
<223> OTHER INFORMATION: SARS-CoV-2 RNA-dependent RNA
      polymerase/helicase region

<400> SEQUENCE: 1

Asn Cys Leu Asp Asp Arg Cys Ile Leu His Cys Ala Asn Phe Asn Val
1               5                   10                  15

Leu Phe Ser Thr Val Phe Pro Pro Thr Ser Phe Gly Pro Leu Val Arg
            20                  25                  30

Lys Ile Phe Val Asp Gly Val Pro Phe Val Val Ser Thr Gly Tyr His
        35                  40                  45

Phe Arg Glu Leu Gly Val Val His Asn Gln Asp Val Asn Leu His Ser
    50                  55                  60

Ser Arg Leu Ser Phe Lys Glu Leu Leu Val Tyr Ala Ala Asp Pro Ala
65                  70                  75                  80

Met His Ala Ala Ser Gly Asn Leu Leu Leu Asp Lys Arg Thr Thr Cys
```

-continued

```
                85                  90                  95

Phe Ser Val Ala Ala Leu Thr Asn Asn Val Ala Phe Gln Thr Val Lys
            100                 105                 110

Pro Gly Asn Phe Asn Lys Asp Phe Tyr Asp Phe Ala Val Ser Lys Gly
        115                 120                 125

Phe Phe Lys Glu Gly Ser Ser Val Glu Leu Lys His Phe Phe Phe Ala
    130                 135                 140

Gln Asp Gly Asn Ala Ala Ile Ser Asp Tyr Asp Tyr Tyr Arg Tyr Asn
145                 150                 155                 160

Leu Pro Thr Met Cys Asp Ile Arg Gln Leu Leu Phe Val Val Glu Val
                165                 170                 175

Val Asp Lys Tyr Phe Asp Cys Tyr Asp Gly Gly Cys Ile Asn Ala Asn
            180                 185                 190

Gln Val Ile Val Asn Asn Leu Asp Lys Ser Ala Gly Phe Pro Phe Asn
        195                 200                 205

Lys Trp Gly Lys Ala Arg Leu Tyr Tyr Asp Ser Met Ser Tyr Glu Asp
    210                 215                 220

Gln Asp Ala Leu Phe Ala Tyr Thr Lys Arg Asn Val Ile Pro Thr Ile
225                 230                 235                 240

Thr Gln Met Asn Leu Lys Tyr Ala Ile Ser Ala Lys Asn Arg Ala Arg
                245                 250                 255

Thr Val Ala Gly Val Ser Ile Cys Ser Thr Met Thr Asn Arg Gln Phe
            260                 265                 270

His Gln Lys Leu Leu Lys Ser Ile Ala Ala Thr Arg Gly Ala Thr Val
        275                 280                 285

Val Ile Gly Thr Ser Lys Phe Tyr Gly Gly Trp His Asn Met Leu Lys
    290                 295                 300

Thr Val Tyr Ser Asp Val Glu Asn Pro His Leu Met Gly Trp Asp Tyr
305                 310                 315                 320

Pro Lys Cys Asp Arg Ala Met Pro Asn Met Leu Arg Ile Met Ala Ser
                325                 330                 335

Leu Val Leu Ala Arg Lys His Thr Thr Cys Cys Ser Leu Ser His Arg
            340                 345                 350

Phe Tyr Arg Leu Ala Asn Glu Cys Ala Gln Val Leu Ser Glu Met Val
        355                 360                 365

Met Cys Gly Gly Ser Leu Tyr Val Lys Pro Gly Gly Thr Ser Ser Gly
    370                 375                 380

Asp Ala Thr Thr Ala Tyr Ala Asn Ser Val Phe Asn Ile Cys Gln Ala
385                 390                 395                 400

Val Thr Ala Asn Val Asn Ala Leu Leu Ser Thr Asp Gly Asn Lys Ile
                405                 410                 415

Ala Asp Lys Tyr Val Arg Asn Leu Gln His Arg Leu Tyr Glu Cys Leu
            420                 425                 430

Tyr Arg Asn Arg Asp Val Asp Thr Asp Phe Val Asn Glu Phe Tyr Ala
        435                 440                 445

Tyr Leu Arg Lys His Phe Ser Met Met Ile Leu Ser Asp Asp Ala Val
    450                 455                 460

Val Cys Phe Asn Ser Thr Tyr Ala Ser Gln Gly Leu Val Ala Ser Ile
465                 470                 475                 480

Lys Asn Phe Lys Ser Val Leu Tyr Tyr Gln Asn Asn Val Phe Met Ser
                485                 490                 495

Glu Ala Lys Cys Trp Thr Glu Thr Asp Leu Thr Lys Gly Pro His Glu
            500                 505                 510
```

-continued

```
Phe Cys Ser Gln His Thr Met Leu Val Lys Gln Gly Asp Asp Tyr Val
        515                 520                 525

Tyr Leu Pro Tyr Pro Asp Pro Ser Arg Ile Leu Gly Ala Gly Cys Phe
    530                 535                 540

Val Asp Asp Ile Val Lys Thr Asp Gly Thr Leu Met Ile Glu Arg Phe
545                 550                 555                 560

Val Ser Leu Ala Ile Asp Ala Tyr Pro Leu Thr Lys His Pro Asn Gln
                565                 570                 575

Glu Tyr Ala Asp Val Phe His Leu Tyr Leu Gln Tyr Ile Arg Lys Leu
            580                 585                 590

His Asp Glu Leu Thr Gly His Met Leu Asp Met Tyr Ser Val Met Leu
        595                 600                 605

Thr Asn Asp Asn Thr Ser Arg Tyr Trp Glu Pro Glu Phe Tyr Glu Ala
    610                 615                 620

Met Tyr Thr Pro His Thr Val Leu Gln Ala Val Gly Ala Cys Val Leu
625                 630                 635                 640

Cys Asn Ser Gln Thr Ser Leu Arg Cys Gly Ala Cys Ile Arg Arg Pro
                645                 650                 655

Phe Leu Cys Cys Lys Cys Cys Tyr Asp His Val Ile Ser Thr Ser His
            660                 665                 670

Lys Leu Val Leu Ser Val Asn Pro Tyr Val Cys Asn Ala Pro Gly Cys
        675                 680                 685

Asp Val Thr Asp Val Thr Gln Leu Tyr Leu Gly Gly Met Ser Tyr Tyr
    690                 695                 700

Cys Lys Ser His Lys Pro Pro Ile Ser Phe Pro Leu Cys Ala Asn Gly
705                 710                 715                 720

Gln Val Phe Gly Leu Tyr Lys Asn Thr Cys Val Gly Ser Asp Asn Val
                725                 730                 735

Thr Asp Phe Asn Ala Ile Ala Thr Cys Asp Trp Thr Asn Ala Gly Asp
            740                 745                 750

Tyr Ile Leu Ala Asn Thr Cys Thr Glu Arg Leu Lys Leu Phe Ala Ala
        755                 760                 765

Glu Thr Leu Lys Ala Thr Glu Glu Thr Phe Lys Leu Ser Tyr Gly Ile
    770                 775                 780

Ala Thr Val Arg Glu Val Leu Ser Asp Arg Glu Leu His Leu Ser Trp
785                 790                 795                 800

Glu Val Gly Lys Pro Arg Pro Pro Leu Asn Arg Asn Tyr Val Phe Thr
                805                 810                 815

Gly Tyr Arg Val Thr Lys Asn Ser Lys Val Gln Ile Gly Glu Tyr Thr
            820                 825                 830

Phe Glu Lys Gly Asp Tyr Gly Asp Ala Val Val Tyr Arg Gly Thr Thr
        835                 840                 845

Thr Tyr Lys Leu Asn Val Gly Asp Tyr Phe Val Leu Thr Ser His Thr
    850                 855                 860

Val Met Pro Leu Ser Ala Pro Thr Leu Val Pro Gln Glu His Tyr Val
865                 870                 875                 880

Arg Ile Thr Gly Leu Tyr Pro Thr Leu Asn Ile Ser Asp Glu Phe Ser
                885                 890                 895

Ser Asn Val Ala Asn Tyr Gln Lys Val Gly Met Gln Lys Tyr Ser Thr
            900                 905                 910

Leu Gln Gly Pro Pro Gly Thr Gly Lys Ser His Phe Ala Ile Gly Leu
        915                 920                 925
```

-continued

```
Ala Leu Tyr Tyr Pro Ser Ala Arg Ile Val Tyr Thr Ala Cys Ser His
    930                 935                 940

Ala Ala Val Asp Ala Leu Cys Glu Lys Ala Leu Lys Tyr Leu Pro Ile
945                 950                 955                 960

Asp Lys Cys Ser Arg Ile Ile Pro Ala Arg Ala Arg Val Glu Cys Phe
                965                 970                 975

Asp Lys Phe Lys Val Asn Ser Thr Leu Glu Gln Tyr Val Phe Cys Thr
            980                 985                 990

Val Asn Ala Leu Pro Glu Thr Thr  Ala Asp Ile Val Val  Phe Asp Glu
        995                 1000                1005

Ile Ser  Met Ala Thr Asn Tyr  Asp Leu Ser Val Val  Asn Ala Arg
    1010                1015                1020

Leu Arg  Ala Lys His Tyr Val  Tyr Ile Gly Asp Pro  Ala Gln Leu
    1025                1030                1035

Pro Ala  Pro Arg Thr Leu Leu  Thr Lys Gly Thr Leu  Glu Pro Glu
    1040                1045                1050

Tyr Phe  Asn Ser Val Cys Arg  Leu Met Lys Thr Ile  Gly Pro Asp
    1055                1060                1065

Met Phe  Leu Gly Thr Cys Arg  Arg Cys Pro Ala Glu  Ile Val Asp
    1070                1075                1080

Thr Val  Ser Ala Leu Val Tyr  Asp Asn Lys Leu
    1085                1090
```

<210> SEQ ID NO 2
<211> LENGTH: 204
<212> TYPE: PRT
<213> ORGANISM: Artificial Sequence
<220> FEATURE:
<223> OTHER INFORMATION: SARS-CoV-2 RNA-dependent RNA polymerase region

<400> SEQUENCE: 2

```
Phe Gln Thr Val Lys Pro Gly Asn Phe Asn Lys Asp Phe Tyr Asp Phe
1               5                   10                  15

Ala Val Ser Lys Gly Phe Phe Lys Glu Gly Ser Ser Val Glu Leu Lys
            20                  25                  30

His Phe Phe Phe Ala Gln Asp Gly Asn Ala Ala Ile Ser Asp Tyr Asp
        35                  40                  45

Tyr Tyr Arg Tyr Asn Leu Pro Thr Met Cys Asp Ile Arg Gln Leu Leu
    50                  55                  60

Phe Val Val Glu Val Val Asp Lys Tyr Phe Asp Cys Tyr Asp Gly Gly
65                  70                  75                  80

Cys Ile Asn Ala Asn Gln Val Ile Val Asn Asn Leu Asp Lys Ser Ala
                85                  90                  95

Gly Phe Pro Phe Asn Lys Trp Gly Lys Ala Arg Leu Tyr Tyr Asp Ser
            100                 105                 110

Met Ser Tyr Glu Asp Gln Asp Ala Leu Phe Ala Tyr Thr Lys Arg Asn
        115                 120                 125

Val Ile Pro Thr Ile Thr Gln Met Asn Leu Lys Tyr Ala Ile Ser Ala
    130                 135                 140

Lys Asn Arg Ala Arg Thr Val Ala Gly Val Ser Ile Cys Ser Thr Met
145                 150                 155                 160

Thr Asn Arg Gln Phe His Gln Lys Leu Leu Lys Ser Ile Ala Ala Thr
                165                 170                 175

Arg Gly Ala Thr Val Val Ile Gly Thr Ser Lys Phe Tyr Gly Gly Trp
            180                 185                 190
```

-continued

```
His Asn Met Leu Lys Thr Val Tyr Ser Asp Val Glu
        195                 200


<210> SEQ ID NO 3
<211> LENGTH: 201
<212> TYPE: PRT
<213> ORGANISM: Artificial Sequence
<220> FEATURE:
<223> OTHER INFORMATION: SARS-CoV-2 helicase region

<400> SEQUENCE: 3

Glu Phe Ser Ser Asn Val Ala Asn Tyr Gln Lys Val Gly Met Gln Lys
1               5                   10                  15

Tyr Ser Thr Leu Gln Gly Pro Pro Gly Thr Gly Lys Ser His Phe Ala
            20                  25                  30

Ile Gly Leu Ala Leu Tyr Tyr Pro Ser Ala Arg Ile Val Tyr Thr Ala
        35                  40                  45

Cys Ser His Ala Ala Val Asp Ala Leu Cys Glu Lys Ala Leu Lys Tyr
    50                  55                  60

Leu Pro Ile Asp Lys Cys Ser Arg Ile Ile Pro Ala Arg Ala Arg Val
65                  70                  75                  80

Glu Cys Phe Asp Lys Phe Lys Val Asn Ser Thr Leu Glu Gln Tyr Val
                85                  90                  95

Phe Cys Thr Val Asn Ala Leu Pro Glu Thr Thr Ala Asp Ile Val Val
            100                 105                 110

Phe Asp Glu Ile Ser Met Ala Thr Asn Tyr Asp Leu Ser Val Val Asn
        115                 120                 125

Ala Arg Leu Arg Ala Lys His Tyr Val Tyr Ile Gly Asp Pro Ala Gln
    130                 135                 140

Leu Pro Ala Pro Arg Thr Leu Leu Thr Lys Gly Thr Leu Glu Pro Glu
145                 150                 155                 160

Tyr Phe Asn Ser Val Cys Arg Leu Met Lys Thr Ile Gly Pro Asp Met
                165                 170                 175

Phe Leu Gly Thr Cys Arg Arg Cys Pro Ala Glu Ile Val Asp Thr Val
            180                 185                 190

Ser Ala Leu Val Tyr Asp Asn Lys Leu
        195                 200


<210> SEQ ID NO 4
<211> LENGTH: 538
<212> TYPE: PRT
<213> ORGANISM: Artificial Sequence
<220> FEATURE:
<223> OTHER INFORMATION: SARS-CoV-2 nsp6-10 region

<400> SEQUENCE: 4

Gly Gly Lys Pro Cys Ile Lys Val Ala Thr Val Gln Ser Lys Met Ser
1               5                   10                  15

Asp Val Lys Cys Thr Ser Val Val Leu Leu Ser Val Leu Gln Gln Leu
            20                  25                  30

Arg Val Glu Ser Ser Ser Lys Leu Trp Ala Gln Cys Val Gln Leu His
        35                  40                  45

Asn Asp Ile Leu Leu Ala Lys Asp Thr Thr Glu Ala Phe Glu Lys Met
    50                  55                  60

Val Ser Leu Val Leu Leu Ser Met Gln Gly Ala Val Asp Ile Asn Lys
65                  70                  75                  80

Leu Cys Glu Glu Met Leu Asp Asn Arg Ala Thr Leu Gln Ala Ile Ala
                85                  90                  95
```

-continued

```
Ser Glu Phe Ser Ser Leu Pro Ser Tyr Ala Ala Phe Ala Thr Ala Gln
            100                 105                 110

Glu Ala Tyr Glu Gln Ala Val Ala Asn Gly Asp Ser Glu Val Val Leu
        115                 120                 125

Lys Lys Leu Lys Lys Ser Leu Asn Val Ala Lys Ser Glu Phe Asp Arg
    130                 135                 140

Asp Ala Ala Met Gln Arg Lys Leu Glu Lys Met Ala Asp Gln Ala Met
145                 150                 155                 160

Thr Gln Met Tyr Lys Gln Ala Arg Ser Glu Asp Lys Arg Ala Lys Val
                165                 170                 175

Thr Ser Ala Met Gln Thr Met Leu Phe Thr Met Leu Arg Lys Leu Asp
            180                 185                 190

Asn Asp Ala Leu Asn Asn Ile Ile Asn Asn Ala Arg Asp Gly Cys Val
        195                 200                 205

Pro Leu Asn Ile Ile Pro Leu Thr Thr Ala Ala Lys Leu Met Val Val
    210                 215                 220

Ile Pro Asp Tyr Asn Thr Tyr Lys Asn Thr Cys Asp Gly Thr Thr Phe
225                 230                 235                 240

Thr Tyr Ala Ser Ala Leu Trp Glu Ile Gln Gln Val Val Asp Ala Asp
                245                 250                 255

Ser Lys Ile Val Gln Leu Ser Glu Ile Ser Met Asp Asn Ser Pro Asn
            260                 265                 270

Leu Ala Trp Pro Leu Ile Val Thr Ala Leu Arg Ala Asn Ser Ala Val
        275                 280                 285

Lys Leu Gln Asn Asn Glu Leu Ser Pro Val Ala Leu Arg Gln Met Ser
    290                 295                 300

Cys Ala Ala Gly Thr Thr Gln Thr Ala Cys Thr Asp Asp Asn Ala Leu
305                 310                 315                 320

Ala Tyr Tyr Asn Thr Thr Lys Gly Gly Arg Phe Val Leu Ala Leu Leu
                325                 330                 335

Ser Asp Leu Gln Asp Leu Lys Trp Ala Arg Phe Pro Lys Ser Asp Gly
            340                 345                 350

Thr Gly Thr Ile Tyr Thr Glu Leu Glu Pro Pro Cys Arg Phe Val Thr
        355                 360                 365

Asp Thr Pro Lys Gly Pro Lys Val Lys Tyr Leu Tyr Phe Ile Lys Gly
    370                 375                 380

Leu Asn Asn Leu Asn Arg Gly Met Val Leu Gly Ser Leu Ala Ala Thr
385                 390                 395                 400

Val Arg Leu Gln Ala Gly Asn Ala Thr Glu Val Pro Ala Asn Ser Thr
                405                 410                 415

Val Leu Ser Phe Cys Ala Phe Ala Val Asp Ala Ala Lys Ala Tyr Lys
            420                 425                 430

Asp Tyr Leu Ala Ser Gly Gly Gln Pro Ile Thr Asn Cys Val Lys Met
        435                 440                 445

Leu Cys Thr His Thr Gly Thr Gly Gln Ala Ile Thr Val Thr Pro Glu
    450                 455                 460

Ala Asn Met Asp Gln Glu Ser Phe Gly Gly Ala Ser Cys Cys Leu Tyr
465                 470                 475                 480

Cys Arg Cys His Ile Asp His Pro Asn Pro Lys Gly Phe Cys Asp Leu
                485                 490                 495

Lys Gly Lys Tyr Val Gln Ile Pro Thr Thr Cys Ala Asn Asp Pro Val
            500                 505                 510
```

-continued

```
Gly Phe Thr Leu Lys Asn Thr Val Cys Thr Val Cys Gly Met Trp Lys
        515                 520                 525

Gly Tyr Gly Cys Ser Cys Asp Gln Leu Arg
    530                 535


<210> SEQ ID NO 5
<211> LENGTH: 1094
<212> TYPE: PRT
<213> ORGANISM: Artificial Sequence
<220> FEATURE:
<223> OTHER INFORMATION: Modified RNA-dependent RNA polymerase and
      helicase (region 1)

<400> SEQUENCE: 5

Asn Cys Leu Asp Asp Arg Cys Ile Leu His Cys Ala Asn Phe Asn Val
1               5                   10                  15

Leu Phe Ser Thr Val Phe Pro Pro Thr Ser Phe Gly Pro Leu Val Arg
            20                  25                  30

Lys Ile Phe Val Asp Gly Val Pro Phe Val Val Ser Thr Gly Tyr His
        35                  40                  45

Phe Arg Glu Leu Gly Val Val His Asn Gln Asp Val Asn Leu His Ser
    50                  55                  60

Ser Arg Leu Ser Phe Lys Glu Leu Leu Val Tyr Ala Ala Asp Pro Ala
65                  70                  75                  80

Met His Ala Ala Ser Gly Asn Leu Leu Leu Asp Lys Arg Thr Thr Cys
                85                  90                  95

Phe Ser Val Ala Ala Leu Thr Asn Asn Val Ala Phe Gln Thr Val Lys
            100                 105                 110

Pro Gly Asn Phe Asn Lys Asp Phe Tyr Asp Phe Ala Val Ser Lys Gly
        115                 120                 125

Phe Phe Lys Glu Gly Ser Ser Val Glu Leu Lys His Phe Phe Phe Ala
    130                 135                 140

Gln Asp Gly Asn Ala Ala Ile Ser Asp Tyr Asp Tyr Tyr Arg Tyr Asn
145                 150                 155                 160

Leu Pro Thr Met Cys Asp Ile Arg Gln Leu Leu Phe Val Val Glu Val
                165                 170                 175

Val Asp Lys Tyr Phe Asp Cys Tyr Asp Gly Gly Cys Ile Asn Ala Asn
            180                 185                 190

Gln Val Ile Val Asn Asn Leu Asp Lys Ser Ala Gly Phe Pro Phe Asn
        195                 200                 205

Lys Trp Gly Lys Ala Arg Leu Tyr Tyr Asp Ser Met Ser Tyr Glu Asp
    210                 215                 220

Gln Asp Ala Leu Phe Ala Tyr Thr Lys Arg Asn Val Ile Pro Thr Ile
225                 230                 235                 240

Thr Gln Met Asn Leu Lys Tyr Ala Ile Ser Ala Lys Asn Arg Ala Arg
                245                 250                 255

Thr Val Ala Gly Val Ser Ile Cys Ser Thr Met Thr Asn Arg Gln Phe
            260                 265                 270

His Gln Lys Leu Leu Lys Ser Ile Ala Ala Thr Arg Gly Ala Thr Val
        275                 280                 285

Val Ile Gly Thr Ser Lys Phe Tyr Gly Gly Trp His Asn Met Leu Lys
    290                 295                 300

Thr Val Tyr Ser Asp Val Glu Asn Pro His Leu Met Gly Trp Asp Tyr
305                 310                 315                 320

Pro Lys Cys Asp Arg Ala Met Pro Asn Met Leu Arg Ile Met Ala Ser
                325                 330                 335
```

-continued

```
Leu Val Leu Ala Arg Lys His Thr Thr Cys Cys Ser Leu Ser His Arg
            340                 345                 350

Phe Tyr Arg Leu Ala Asn Glu Cys Ala Gln Val Leu Ser Glu Met Val
        355                 360                 365

Met Cys Gly Gly Ser Leu Tyr Val Lys Pro Gly Gly Thr Ser Ser Gly
    370                 375                 380

Asp Ala Thr Thr Ala Tyr Ala Asn Ser Val Phe Asn Ile Cys Gln Ala
385                 390                 395                 400

Val Thr Ala Asn Val Asn Ala Leu Leu Ser Thr Asp Gly Asn Lys Ile
                405                 410                 415

Ala Asp Lys Tyr Val Arg Asn Leu Gln His Arg Leu Tyr Glu Cys Leu
            420                 425                 430

Tyr Arg Asn Arg Asp Val Asp Thr Asp Phe Val Asn Glu Phe Tyr Ala
        435                 440                 445

Tyr Leu Arg Lys His Phe Ser Met Met Ile Leu Ser Ala Ala Ala Val
    450                 455                 460

Val Cys Phe Asn Ser Thr Tyr Ala Ser Gln Gly Leu Val Ala Ser Ile
465                 470                 475                 480

Lys Asn Phe Lys Ser Val Leu Tyr Tyr Gln Asn Asn Val Phe Met Ser
                485                 490                 495

Glu Ala Lys Cys Trp Thr Glu Thr Asp Leu Thr Lys Gly Pro His Glu
            500                 505                 510

Phe Cys Ser Gln His Thr Met Leu Val Lys Gln Gly Asp Asp Tyr Val
        515                 520                 525

Tyr Leu Pro Tyr Pro Asp Pro Ser Arg Ile Leu Gly Ala Gly Cys Phe
    530                 535                 540

Val Asp Asp Ile Val Lys Thr Asp Gly Thr Leu Met Ile Glu Arg Phe
545                 550                 555                 560

Val Ser Leu Ala Ile Asp Ala Tyr Pro Leu Thr Lys His Pro Asn Gln
                565                 570                 575

Glu Tyr Ala Asp Val Phe His Leu Tyr Leu Gln Tyr Ile Arg Lys Leu
            580                 585                 590

His Asp Glu Leu Thr Gly His Met Leu Asp Met Tyr Ser Val Met Leu
        595                 600                 605

Thr Asn Asp Asn Thr Ser Arg Tyr Trp Glu Pro Glu Phe Tyr Glu Ala
    610                 615                 620

Met Tyr Thr Pro His Thr Val Leu Gln Ala Val Gly Ala Cys Val Leu
625                 630                 635                 640

Cys Asn Ser Gln Thr Ser Leu Arg Cys Gly Ala Cys Ile Arg Arg Pro
                645                 650                 655

Phe Leu Cys Cys Lys Cys Cys Tyr Asp His Val Ile Ser Thr Ser His
            660                 665                 670

Lys Leu Val Leu Ser Val Asn Pro Tyr Val Cys Asn Ala Pro Gly Cys
        675                 680                 685

Asp Val Thr Asp Val Thr Gln Leu Tyr Leu Gly Gly Met Ser Tyr Tyr
    690                 695                 700

Cys Lys Ser His Lys Pro Pro Ile Ser Phe Pro Leu Cys Ala Asn Gly
705                 710                 715                 720

Gln Val Phe Gly Leu Tyr Lys Asn Thr Cys Val Gly Ser Asp Asn Val
                725                 730                 735

Thr Asp Phe Asn Ala Ile Ala Thr Cys Asp Trp Thr Asn Ala Gly Asp
            740                 745                 750
```

```
Tyr Ile Leu Ala Asn Thr Cys Thr Glu Arg Leu Lys Leu Phe Ala Ala
        755                 760                 765

Glu Thr Leu Lys Ala Thr Glu Glu Thr Phe Lys Leu Ser Tyr Gly Ile
    770                 775                 780

Ala Thr Val Arg Glu Val Leu Ser Asp Arg Glu Leu His Leu Ser Trp
785                 790                 795                 800

Glu Val Gly Lys Pro Arg Pro Pro Leu Asn Arg Asn Tyr Val Phe Thr
                805                 810                 815

Gly Tyr Arg Val Thr Lys Asn Ser Lys Val Gln Ile Gly Glu Tyr Thr
            820                 825                 830

Phe Glu Lys Gly Asp Tyr Gly Asp Ala Val Val Tyr Arg Gly Thr Thr
        835                 840                 845

Thr Tyr Lys Leu Asn Val Gly Asp Tyr Phe Val Leu Thr Ser His Thr
    850                 855                 860

Val Met Pro Leu Ser Ala Pro Thr Leu Val Pro Gln Glu His Tyr Val
865                 870                 875                 880

Arg Ile Thr Gly Leu Tyr Pro Thr Leu Asn Ile Ser Asp Glu Phe Ser
                885                 890                 895

Ser Asn Val Ala Asn Tyr Gln Lys Val Gly Met Gln Lys Tyr Ser Thr
            900                 905                 910

Leu Gln Gly Pro Pro Gly Thr Gly Lys Ser His Phe Ala Ile Gly Leu
        915                 920                 925

Ala Leu Tyr Tyr Pro Ser Ala Arg Ile Val Tyr Thr Ala Cys Ser His
    930                 935                 940

Ala Ala Val Asp Ala Leu Cys Glu Lys Ala Leu Lys Tyr Leu Pro Ile
945                 950                 955                 960

Asp Lys Cys Ser Arg Ile Ile Pro Ala Arg Ala Arg Val Glu Cys Phe
                965                 970                 975

Asp Lys Phe Lys Val Asn Ser Thr Leu Glu Gln Tyr Val Phe Cys Thr
            980                 985                 990

Val Asn Ala Leu Pro Glu Thr Thr  Ala Asp Ile Val Val  Phe Asp Glu
        995                 1000                1005

Ile Ser  Met Ala Thr Asn Tyr  Asp Leu Ser Val Val  Asn Ala Arg
    1010                 1015                1020

Leu Arg  Ala Lys His Tyr Val  Tyr Ile Gly Asp Pro  Ala Gln Leu
    1025                 1030                1035

Pro Ala  Pro Arg Thr Leu Leu  Thr Lys Gly Thr Leu  Glu Pro Glu
    1040                 1045                1050

Tyr Phe  Asn Ser Val Cys Arg  Leu Met Lys Thr Ile  Gly Pro Asp
    1055                 1060                1065

Met Phe  Leu Gly Thr Cys Arg  Arg Cys Pro Ala Glu  Ile Val Asp
    1070                 1075                1080

Thr Val  Ser Ala Leu Val Tyr  Asp Asn Lys Leu
    1085                 1090
```

<210> SEQ ID NO 6
<211> LENGTH: 1094
<212> TYPE: PRT
<213> ORGANISM: Artificial Sequence
<220> FEATURE:
<223> OTHER INFORMATION: Optimized region 1 polypeptide (region 1 EG-2.1)

<400> SEQUENCE: 6

```
Asn Cys Ser Asp Asp Arg Cys Ile Leu His Cys Ser Asn Phe Asn Val
1               5                   10                  15
```

-continued

```
Leu Phe Ser Thr Val Phe Pro Leu Thr Ser Phe Gly Pro Leu Val Arg
            20                  25                  30

Lys Met Phe Val Asp Gly Val Pro Phe Val Ile Ser Thr Gly Tyr His
        35                  40                  45

Phe Arg Glu Leu Gly Val Leu His Asn Gln Asp Val Asn Leu His Ser
    50                  55                  60

Ser Arg Leu Ser Phe Asn Glu Leu Leu Val Tyr Ala Ala Asp Pro Ala
65                  70                  75                  80

Met His Thr Ala Ser Gly Asn Leu Leu Leu Asp Lys Arg Thr Met Cys
                85                  90                  95

Phe Ser Val Ala Ala Leu Thr Asn Asn Val Ala Phe Gln Thr Val Arg
            100                 105                 110

Pro Gly Asn Phe Asn Lys Asp Phe Tyr Asp Phe Val Val Ser Lys Gly
        115                 120                 125

Phe Phe Lys Glu Gly Ser Phe Val Glu Leu Lys His Phe Phe Phe Ala
    130                 135                 140

Gln Asp Gly Asn Ala Val Ile Ser Asp Tyr Asp Tyr Tyr Arg Tyr Asn
145                 150                 155                 160

Leu Pro Thr Ile Cys Asp Ile Arg Gln Leu Leu Phe Val Val Glu Val
                165                 170                 175

Val Asp Asn Tyr Phe Asp Cys Tyr Asp Gly Gly Cys Ile Asn Ala Ser
            180                 185                 190

Gln Val Ile Val Asn Asn Leu Asp Lys Ser Ala Gly Phe Pro Phe Asn
        195                 200                 205

Lys Trp Gly Lys Ala Arg Phe Tyr Tyr Asp Ser Met Ser Tyr Glu Asp
    210                 215                 220

Gln Asp Ala Leu Phe Val Tyr Thr Lys Arg Asn Val Ile Pro Thr Ile
225                 230                 235                 240

Thr Gln Met Asn Leu Lys Tyr Ala Ile Ser Ala Lys Asn Arg Ser Arg
                245                 250                 255

Thr Val Ala Gly Val Ser Ile Phe Ser Thr Met Thr Asn Arg Gln Phe
            260                 265                 270

Tyr Gln Lys Leu Leu Lys Ser Ile Ala Ser Thr Arg Gly Ala Thr Val
        275                 280                 285

Val Ile Gly Ile Ser Lys Phe Tyr Gly Gly Trp His Asn Met Leu Lys
    290                 295                 300

Thr Ile Tyr Ser Asp Val Glu Asn Pro His Phe Met Gly Trp Asp Tyr
305                 310                 315                 320

Pro Lys Cys Asp Arg Ala Met Pro Asn Ile Leu Arg Ile Met Ala Ser
                325                 330                 335

Leu Val Phe Ala Arg Lys His Thr Thr Cys Cys Ile Leu Ser His Arg
            340                 345                 350

Phe Tyr Arg Leu Ser Asn Glu Cys Ala Gln Val Leu Ser Glu Ile Val
        355                 360                 365

Met Cys Gly Gly Ser Leu Tyr Val Lys Pro Gly Gly Thr Ser Ser Gly
    370                 375                 380

Glu Ala Thr Thr Ala Tyr Ala Asn Ser Val Phe Asn Ile Cys Gln Ser
385                 390                 395                 400

Val Thr Ala Asn Val Asn Ala Leu Leu Ser Thr Asp Gly Asn Lys Ile
                405                 410                 415

Ala Asp Lys Tyr Ile Arg Asn Leu Gln His Arg Leu Tyr Ala Cys Leu
            420                 425                 430
```

```
Tyr Arg Asn Arg Asp Val Asp Ile Asp Phe Val Asn Glu Phe Tyr Ala
        435                 440                 445

Tyr Leu Arg Lys His Phe Ser Ile Met Ile Leu Ser Ala Ala Ala Val
    450                 455                 460

Val Cys Val Asn Ser Thr Tyr Ala Ser Gln Gly Leu Leu Ala Ser Ile
465                 470                 475                 480

Lys Asn Phe Lys Ser Val Leu Tyr Tyr Gln Asn Asn Ile Phe Met Ser
                485                 490                 495

Glu Ala Lys Cys Trp Thr Glu Ile Asp Leu Thr Lys Gly Pro His Glu
            500                 505                 510

Phe Cys Ser Gln His Thr Met Leu Val Lys His Gly Asp Asp Tyr Val
        515                 520                 525

Tyr Leu Ser Tyr Pro Asp Pro Ser Arg Ile Leu Gly Ala Gly Cys Phe
    530                 535                 540

Val Asp Asp Ile Leu Lys Thr Asp Gly Thr Leu Met Ile Glu Arg Phe
545                 550                 555                 560

Val Ser Leu Ala Ile Asp Ala Tyr Pro Leu Ile Lys His Pro Asn Gln
                565                 570                 575

Glu Tyr Ala Asp Val Phe Arg Leu Tyr Leu Gln Tyr Ile Arg Lys Leu
            580                 585                 590

His Tyr Glu Leu Thr Gly His Met Leu Asp Ile Tyr Ser Val Met Leu
        595                 600                 605

Thr Asn Asp Asn Thr Leu Arg Tyr Trp Glu Pro Glu Phe Tyr Asp Ala
    610                 615                 620

Met Tyr Thr Pro His Thr Val Leu Gln Ala Val Gly Val Cys Val Leu
625                 630                 635                 640

Cys Asn Ser Gln Thr Ser Leu Arg Cys Gly Val Cys Ile Arg Arg Pro
                645                 650                 655

Phe Leu Cys Cys Glu Cys Cys Tyr Asp His Val Ile Ser Thr Leu His
            660                 665                 670

Lys Leu Val Leu Ser Val Asn Pro Tyr Val Cys Asn Ala Leu Gly Cys
        675                 680                 685

Asp Val Thr Asp Val Thr Gln Leu Tyr Leu Gly Gly Met Asn Tyr Tyr
    690                 695                 700

Cys Lys Ser His Lys Pro Ser Ile Ser Phe Pro Leu Cys Ala Asn Gly
705                 710                 715                 720

His Val Phe Gly Leu Tyr Lys Asn Thr Cys Phe Gly Ser Asp Asn Val
                725                 730                 735

Thr Asp Phe Asn Ala Ile Ala Thr Cys Asp Trp Ile Asn Ala Gly Asp
            740                 745                 750

Tyr Ile Leu Ala Asn Thr Cys Ile Glu Arg Leu Lys Leu Phe Ala Ala
        755                 760                 765

Glu Thr Leu Lys Ala Ile Glu Glu Thr Phe Lys Leu Ser Tyr Gly Ile
    770                 775                 780

Ala Ile Val Arg Glu Val Leu Ser Asp Arg Glu Leu Tyr Leu Ser Trp
785                 790                 795                 800

Glu Val Gly Lys Pro Arg Pro Pro Phe Asn Arg Asn Tyr Val Phe Thr
                805                 810                 815

Gly Tyr Arg Leu Thr Lys Asn Ser Lys Val Gln Ile Gly Asp Tyr Thr
            820                 825                 830

Phe Glu Lys Gly Asp Tyr Val Asp Ala Val Val Tyr Arg Gly Thr Thr
        835                 840                 845

Thr Tyr Arg Leu Asn Val Gly Asp Tyr Phe Val Leu Thr Ser His Thr
```

```
    850                 855                 860

Val Ile Pro Leu Ser Ala Pro Thr Leu Val Pro Gln Asp His Tyr Val
865                 870                 875                 880

Arg Ile Thr Gly Leu Tyr Pro Thr Leu Asn Ile Ser Asp Asp Phe Ser
                885                 890                 895

Ser Asn Val Ala Asn Tyr Gln Lys Val Gly Ile Gln Lys Tyr Ser Thr
            900                 905                 910

Leu Gln Gly Pro Pro Gly Thr Gly Lys Ser Tyr Phe Ala Ile Gly Leu
        915                 920                 925

Ala Leu Tyr Tyr Leu Ser Ala Arg Ile Val Tyr Thr Ala Cys Ser His
    930                 935                 940

Ala Ala Val Tyr Thr Leu Cys Glu Lys Ala Leu Lys Tyr Phe Pro Ile
945                 950                 955                 960

Asp Lys Cys Ser Arg Ile Ile Pro Ala Arg Ala Arg Val Asp Cys Phe
                965                 970                 975

Asp Lys Phe Lys Val Asn Leu Thr Leu Glu Gln Tyr Val Phe Cys Thr
            980                 985                 990

Val Asn Ala Leu Pro Asp Thr Thr  Ala Asp Ile Val Val  Phe Asp Glu
        995                 1000                1005

Ile Ser  Met Thr Thr Asn Tyr  Asp Leu Ser Val Val  Asn Ala Arg
    1010                 1015                 1020

Leu Cys  Ala Lys His Tyr Val  Tyr Ile Gly Asp Ser  Ala Gln Leu
    1025                 1030                 1035

Pro Ala  Pro Arg Thr Leu Leu  Ile Lys Gly Thr Leu  Glu Pro Glu
    1040                 1045                 1050

Tyr Phe  Asn Ser Val Cys Arg  Phe Met Lys Thr Ile  Gly Pro Asp
    1055                 1060                 1065

Met Phe  Leu Gly Thr Cys Arg  Arg Cys Pro Ser Glu  Ile Val Asp
    1070                 1075                 1080

Thr Val  Ser Ala Leu Val Tyr  Asp Asn Arg Leu
    1085                 1090


<210> SEQ ID NO 7
<211> LENGTH: 1094
<212> TYPE: PRT
<213> ORGANISM: Artificial Sequence
<220> FEATURE:
<223> OTHER INFORMATION: Additional optimized region 1 polypeptide
      (region 1 EG-2.2)

<400> SEQUENCE: 7

Asn Cys Leu Asp Asp Arg Cys Val Leu His Cys Ala Asn Phe Asn Val
1               5                   10                  15

Leu Phe Ser Thr Val Phe Pro Phe Thr Ser Phe Gly Pro Leu Val Arg
            20                  25                  30

Lys Ile Cys Val Asp Gly Val Pro Phe Val Val Ser Thr Gly His His
        35                  40                  45

Phe Arg Glu Leu Gly Val Val Tyr Asn Gln Asp Val Asn Leu His Ser
    50                  55                  60

Phe Arg Leu Ser Phe Lys Glu Leu Leu Leu Tyr Ala Ala Asp Pro Ala
65                  70                  75                  80

Met His Val Ala Ser Gly Asn Leu Leu Leu Asp Arg Arg Thr Thr Cys
                85                  90                  95

Phe Ser Val Ala Ala Leu Thr Asn Asn Phe Ala Phe Gln Thr Val Lys
            100                 105                 110
```

-continued

```
Pro Gly Asn Phe Asn Lys Asp Phe Tyr Asp Phe Ala Leu Ser Lys Gly
        115                 120                 125

Phe Phe Lys Glu Gly Ser Pro Val Glu Leu Lys His Phe Phe Phe Val
    130                 135                 140

Gln Asp Gly Asn Ala Ala Ile Ser Asp Tyr Glu Tyr Tyr Arg Tyr Asn
145                 150                 155                 160

Leu Pro Thr Met Phe Asp Ile Arg Gln Leu Leu Phe Val Phe Glu Val
                165                 170                 175

Val Asp Lys Tyr Phe Asp Cys Tyr Asp Gly Gly Cys Ile Asn Ala Asn
            180                 185                 190

Gln Val Thr Val Asn Asn Leu Asp Lys Ser Ala Gly Phe Pro Phe Asn
        195                 200                 205

Lys Trp Gly Lys Ala Arg Leu Tyr Tyr Glu Ser Met Ser Tyr Glu Asp
    210                 215                 220

Gln Asp Val Leu Phe Ala Tyr Thr Lys Arg Asn Val Thr Pro Thr Ile
225                 230                 235                 240

Thr Gln Met Asn Leu Lys Tyr Ala Ile Ser Val Lys Asn Arg Ala Arg
                245                 250                 255

Thr Val Ala Gly Val Ser Ile Cys Ser Thr Ile Thr Asn Arg Gln Phe
            260                 265                 270

His Gln Lys Leu Leu Lys Ser Ile Ala Ala Thr Gly Gly Ala Thr Val
        275                 280                 285

Val Ile Gly Thr Ser Lys Phe Tyr Gly Gly Trp His Asn Ile Leu Lys
    290                 295                 300

Thr Val Tyr Ser Asp Val Glu Asn Pro Tyr Leu Met Gly Trp Asp Tyr
305                 310                 315                 320

Pro Lys Cys Asp Arg Ala Met Pro Asn Met Leu Arg Ile Val Ala Ser
                325                 330                 335

Leu Val Leu Ala Arg Lys His Thr Met Cys Cys Ser Leu Ser His Arg
            340                 345                 350

Phe Tyr Arg Leu Thr Asn Glu Cys Ala Gln Val Leu Ser Glu Met Val
        355                 360                 365

Ile Cys Gly Gly Ser Leu Tyr Val Lys Pro Gly Gly Thr Ser Ser Gly
    370                 375                 380

Asp Ala Thr Thr Ala Tyr Ala Asn Ser Val Phe Asn Ile Phe Gln Ala
385                 390                 395                 400

Val Thr Ala Asn Val Asn Thr Leu Leu Ser Thr Asp Gly Asn Lys Ile
                405                 410                 415

Ala Asp Asn Tyr Val Arg Asn Leu Gln His Arg Leu Tyr Gly Cys Leu
            420                 425                 430

Tyr Arg Asn Arg Asp Val Tyr Thr Asp Phe Val Asn Glu Phe Tyr Thr
        435                 440                 445

Tyr Leu Arg Lys His Phe Ser Met Ile Ile Leu Ser Ala Ala Ala Val
    450                 455                 460

Val Cys Phe Asn Ser Thr Tyr Val Ser Gln Gly Leu Val Ala Ser Ile
465                 470                 475                 480

Arg Asn Phe Lys Ser Val Leu Tyr Tyr Gln Asn Asn Val Phe Met Ser
                485                 490                 495

Glu Val Lys Cys Trp Thr Glu Thr Asp Leu Ile Lys Gly Pro His Glu
            500                 505                 510

Phe Cys Ser Gln His Thr Ile Leu Val Lys Gln Gly Asp Asp Tyr Val
        515                 520                 525

Tyr Phe Pro Tyr Pro Asp Pro Ser Arg Ile Leu Gly Ala Gly Cys Phe
```

-continued

```
    530                 535                 540

Val Asp Asp Val Val Lys Thr Asp Gly Thr Leu Met Val Glu Arg Phe
545                 550                 555                 560

Val Ser Leu Ala Ile Asp Ala Tyr Pro Phe Thr Lys His Pro Asn Gln
                565                 570                 575

Glu Tyr Ala Tyr Val Phe His Leu Tyr Leu Gln Tyr Ile Lys Lys Leu
            580                 585                 590

His Asp Glu Leu Thr Gly His Ile Leu Asp Met Tyr Ser Val Met Leu
        595                 600                 605

Ile Asn Asp Asn Thr Ser Arg Tyr Trp Glu Ser Glu Phe Tyr Glu Ala
    610                 615                 620

Met Tyr Thr Ser His Thr Val Leu Gln Ala Val Gly Ser Cys Val Leu
625                 630                 635                 640

Cys Asn Ser Gln Thr Leu Leu Arg Cys Gly Ala Cys Ile Arg Lys Pro
                645                 650                 655

Phe Leu Cys Cys Lys Cys Cys Tyr Asp His Ile Ile Ser Thr Ser His
            660                 665                 670

Lys Leu Val Phe Ser Val Asn Pro Tyr Val Cys Asn Val Pro Gly Cys
        675                 680                 685

Asp Val Thr Asp Val Thr Gln Leu Cys Leu Gly Gly Met Ser Tyr Tyr
    690                 695                 700

Cys Lys Pro His Lys Pro Pro Ile Ser Phe Pro Leu Cys Val Asn Gly
705                 710                 715                 720

Gln Val Phe Gly Leu Tyr Lys Asn Thr Cys Ala Gly Ser Asp Asn Val
                725                 730                 735

Thr Asp Phe Asn Ala Ile Ser Thr Cys Asp Trp Thr Asn Ala Gly Asp
            740                 745                 750

Tyr Ile Leu Ala Asn Ala Cys Thr Glu Arg Leu Lys Leu Phe Ala Ala
        755                 760                 765

Glu Met Leu Lys Ala Thr Glu Glu Thr Phe Lys Leu Ser Tyr Gly Val
    770                 775                 780

Ala Thr Val Arg Glu Val Leu Ser Asp Lys Glu Leu His Leu Ser Trp
785                 790                 795                 800

Glu Val Gly Arg Pro Arg Pro Pro Leu Asn Arg Asn Tyr Val Phe Thr
                805                 810                 815

Gly Tyr His Val Thr Lys Asn Ser Lys Val Gln Thr Gly Glu Tyr Thr
            820                 825                 830

Phe Glu Lys Gly Tyr Tyr Gly Asp Ala Val Val Tyr Arg Gly Ile Thr
        835                 840                 845

Thr Tyr Lys Leu Asn Val Gly Asp Tyr Phe Leu Leu Thr Ser His Thr
    850                 855                 860

Val Met Pro Leu Ser Ala Pro Ile Leu Val Pro Gln Glu His Tyr Val
865                 870                 875                 880

Arg Ile Ile Gly Leu Tyr Pro Thr Leu Asn Ile Ser Tyr Glu Phe Ser
                885                 890                 895

Ser Asn Val Ala Asn Tyr Gln Lys Val Gly Met Gln Arg Tyr Ser Thr
            900                 905                 910

Leu Gln Gly Pro Pro Gly Thr Gly Lys Ser His Phe Ala Ile Gly Leu
        915                 920                 925

Ser Leu Tyr Tyr Pro Ser Ala Arg Ile Met Tyr Thr Ala Cys Ser His
    930                 935                 940

Ala Ala Val Asp Ala Leu Cys Asp Lys Ala Leu Lys Tyr Leu Pro Ile
945                 950                 955                 960
```

-continued

```
Asp Lys Cys Ser Arg Ile Ile Pro Ala Arg Ala Leu Val Glu Cys Phe
            965                 970                 975

Asp Lys Phe Lys Leu Asn Ser Thr Leu Glu Gln Tyr Val Phe Cys Thr
        980                 985                 990

Val Asn Ala Leu Pro Glu Thr Thr  Val Asp Ile Val Val  Phe Asp Glu
    995                 1000                 1005

Ile Ser  Met Thr Thr Asn Tyr  Asp Leu Ser Val Val  Asn Val Arg
    1010                 1015                 1020

Leu Arg  Ala Lys His Tyr Val  Tyr Val Gly Asp Pro  Ala Gln Leu
    1025                 1030                 1035

Pro Ala  Pro Arg Thr Leu Leu  Thr Lys Gly Ile Leu  Glu Pro Glu
    1040                 1045                 1050

Tyr Phe  Asn Ser Val Cys Arg  Leu Ile Lys Thr Ile  Gly Pro Asp
    1055                 1060                 1065

Met Phe  Leu Arg Thr Cys Arg  Arg Cys Pro Ala Glu  Ile Val Asp
    1070                 1075                 1080

Thr Leu  Ser Ala Leu Val Tyr  Asp Asn Lys Leu
    1085                 1090


<210> SEQ ID NO 8
<211> LENGTH: 1094
<212> TYPE: PRT
<213> ORGANISM: Artificial Sequence
<220> FEATURE:
<223> OTHER INFORMATION: Sarbecovirus optimized region 1 polypeptide
      (region 1 SARBECO-EG-2.1)

<400> SEQUENCE: 8

Asn Cys Leu Asp Asp Arg Cys Ile Leu His Cys Ala Asn Phe Asn Val
1               5                   10                  15

Leu Phe Ser Thr Val Phe Pro Leu Thr Ser Phe Gly Pro Leu Val Arg
            20                  25                  30

Lys Ile Phe Val Asp Gly Val Pro Phe Val Val Ser Thr Gly Tyr His
        35                  40                  45

Phe Arg Glu Leu Gly Val Val His Asn Gln Asp Val Asn Ile His Ser
    50                  55                  60

Ser Arg Leu Ser Phe Lys Glu Leu Leu Val Tyr Ala Ala Asp Pro Ala
65                  70                  75                  80

Met His Ala Ala Ser Gly Asn Leu Leu Leu Asp Lys Arg Thr Thr Cys
                85                  90                  95

Phe Ser Val Ala Ala Leu Thr Asn Asn Val Ser Phe Gln Thr Val Lys
            100                 105                 110

Pro Gly Asn Phe Asn Lys Asp Phe Tyr Asp Phe Ala Val Ser Lys Gly
        115                 120                 125

Phe Phe Lys Glu Gly Ser Ser Val Glu Leu Lys His Phe Phe Phe Ala
    130                 135                 140

Gln Asp Gly Asn Ala Ala Ile Ser Asp Tyr Asp Tyr Tyr Arg Tyr Asn
145                 150                 155                 160

Leu Pro Thr Met Cys Asp Ile Arg Gln Leu Leu Phe Val Val Glu Val
                165                 170                 175

Val Asp Lys Tyr Phe Asp Cys Tyr Asp Gly Gly Cys Ile Asn Ala Asn
            180                 185                 190

Gln Val Ile Val Asn Asn Leu Asp Lys Ser Ala Gly Phe Pro Phe Asn
        195                 200                 205

Lys Trp Gly Lys Ala Arg Leu Tyr Tyr Asp Ser Met Ser Tyr Glu Asp
```

-continued

```
    210                 215                 220

Gln Asp Ala Leu Phe Ala Tyr Thr Lys Arg Asn Val Leu Pro Thr Ile
225                 230                 235                 240

Thr Gln Met Asn Leu Lys Tyr Ala Ile Ser Ala Lys Asn Arg Ala Arg
                245                 250                 255

Thr Val Ala Gly Val Ser Ile Cys Ser Thr Met Thr Asn Arg Gln Phe
            260                 265                 270

His Gln Lys Leu Leu Lys Ser Ile Ala Ala Thr Arg Gly Ala Thr Val
        275                 280                 285

Val Ile Gly Thr Ser Lys Phe Tyr Gly Gly Trp Asn Asn Met Leu Lys
    290                 295                 300

Thr Val Tyr Ser Asp Val Glu Thr Pro His Leu Met Gly Trp Asp Tyr
305                 310                 315                 320

Pro Lys Cys Asp Arg Ala Met Pro Asn Met Leu Arg Ile Met Ala Ser
                325                 330                 335

Leu Val Leu Ala Arg Lys His Ser Thr Cys Cys Asn Leu Ser His Arg
            340                 345                 350

Phe Tyr Arg Leu Ala Asn Glu Cys Ala Gln Val Leu Ser Glu Met Val
        355                 360                 365

Met Cys Gly Gly Ser Leu Tyr Val Lys Pro Gly Gly Thr Ser Ser Gly
    370                 375                 380

Asp Ala Thr Thr Ala Tyr Ala Asn Ser Val Phe Asn Ile Cys Gln Ala
385                 390                 395                 400

Val Thr Ala Asn Val Asn Ala Leu Leu Ser Thr Asp Gly Asn Lys Ile
                405                 410                 415

Gly Asp Lys Tyr Ile Arg Asn Leu Gln His Arg Leu Tyr Glu Cys Leu
            420                 425                 430

Tyr Arg Asn Arg Asp Val Asp His Glu Phe Val Asp Glu Phe Tyr Ala
        435                 440                 445

Tyr Leu Arg Lys His Phe Ser Met Met Ile Leu Ser Ala Ala Ala Val
    450                 455                 460

Val Cys Tyr Asn Ser Asn Tyr Ala Ala Gln Gly Leu Val Ala Ser Ile
465                 470                 475                 480

Lys Asn Phe Lys Ala Val Leu Tyr Tyr Gln Asn Asn Val Phe Met Ser
                485                 490                 495

Glu Ala Lys Cys Trp Thr Glu Thr Asp Leu Thr Arg Gly Pro His Glu
            500                 505                 510

Phe Cys Ser Gln His Thr Met Leu Val Lys Gln Gly Asp Asp Tyr Val
        515                 520                 525

Tyr Leu Pro Tyr Pro Asp Pro Ser Arg Ile Leu Gly Ala Gly Cys Phe
    530                 535                 540

Val Asp Asp Ile Val Lys Thr Asp Gly Thr Leu Met Ile Glu Arg Phe
545                 550                 555                 560

Val Ser Leu Ala Ile Asp Ala Tyr Pro Leu Thr Lys His Pro Asn Gln
                565                 570                 575

Glu Tyr Ala Asp Val Phe His Leu Tyr Leu Gln Tyr Ile Arg Lys Leu
            580                 585                 590

His Asp Glu Leu Thr Gly His Met Leu Asp Met Tyr Ser Val Met Leu
        595                 600                 605

Thr Asn Asp Ser Thr Ser Arg Tyr Trp Glu Pro Glu Phe Tyr Glu Ala
    610                 615                 620

Met Tyr Thr Pro His Thr Ile Leu Gln Ala Val Gly Ala Cys Val Leu
625                 630                 635                 640
```

-continued

Cys Asn Ser Gln Thr Ser Leu Arg Cys Gly Ala Cys Ile Arg Arg Pro
645 650 655

Phe Leu Cys Cys Lys Cys Cys Tyr Asp His Val Ile Ser Thr Ser His
660 665 670

Lys Leu Val Leu Ser Val Asn Pro Tyr Val Cys Asn Ala Thr Gly Cys
675 680 685

Asp Val Thr Asp Val Thr Gln Leu Tyr Leu Gly Gly Met Ser Tyr Tyr
690 695 700

Cys Lys Ala His Lys Pro Pro Ile Ser Phe Pro Leu Cys Ala Asn Gly
705 710 715 720

Gln Val Phe Gly Leu Tyr Lys Asn Thr Cys Val Gly Ser Asp Asn Val
725 730 735

Thr Asp Phe Asn Ala Ile Ala Thr Cys Asp Trp Thr Asn Ala Gly Asp
740 745 750

Tyr Ile Leu Ala Asn Thr Cys Thr Glu Arg Leu Lys Leu Phe Ala Ala
755 760 765

Glu Thr Leu Lys Ala Thr Glu Glu Thr Phe Lys Leu Ser Tyr Gly Ile
770 775 780

Ala Thr Val Arg Glu Val Leu Ser Asp Arg Glu Leu Tyr Leu Ser Trp
785 790 795 800

Glu Val Gly Lys Pro Arg Pro Pro Leu Asn Arg Asn Tyr Val Phe Thr
805 810 815

Gly Tyr Arg Val Thr Lys Asn Ser Lys Thr Gln Ile Gly Glu Tyr Thr
820 825 830

Phe Glu Lys Gly Asp Tyr Gly Asp Ala Val Val Tyr Arg Gly Thr Thr
835 840 845

Thr Tyr Lys Leu Asn Val Gly Asp Tyr Phe Val Leu Thr Ser His Thr
850 855 860

Val Met Pro Leu Ser Ala Pro Thr Leu Val Pro Gln Glu His Tyr Val
865 870 875 880

Arg Ile Thr Gly Leu Tyr Pro Thr Leu Asn Ile Ser Glu Glu Phe Ser
885 890 895

Ser Asn Val Ala Asn Tyr Gln Lys Ile Gly Met Gln Lys Tyr Ser Thr
900 905 910

Leu Gln Gly Pro Pro Gly Thr Gly Lys Ser His Phe Ala Ile Gly Leu
915 920 925

Ala Leu Tyr Tyr Pro Ser Ala Arg Ile Val Tyr Thr Ala Cys Ser His
930 935 940

Ala Ala Val Asp Ala Leu Cys Glu Lys Ala Leu Lys Tyr Leu Pro Ile
945 950 955 960

Asp Lys Cys Ser Arg Ile Ile Pro Ala Arg Ala Arg Val Glu Cys Phe
965 970 975

Asp Lys Phe Lys Val Asn Ser Thr Leu Glu Gln Tyr Val Phe Cys Thr
980 985 990

Val Asn Ala Leu Pro Glu Thr Thr Ala Asp Ile Val Val Phe Asp Glu
995 1000 1005

Ile Ser Met Ala Thr Asn Tyr Asp Leu Ser Val Val Asn Ala Arg
1010 1015 1020

Leu Arg Ala Lys His Tyr Val Tyr Ile Gly Asp Pro Ala Gln Leu
1025 1030 1035

Pro Ala Pro Arg Thr Leu Leu Thr Lys Gly Thr Leu Glu Pro Glu
1040 1045 1050

```
Tyr Phe  Asn Ser Val Cys Arg  Leu Met Lys Thr Ile  Gly Pro Asp
    1055                 1060                 1065

Met Phe  Leu Gly Thr Cys Arg  Arg Cys Pro Ala Glu  Ile Val Asp
    1070                 1075                 1080

Thr Val  Ser Ala Leu Val Tyr  Asp Asn Lys Leu
    1085                 1090


<210> SEQ ID NO 9
<211> LENGTH: 1094
<212> TYPE: PRT
<213> ORGANISM: Artificial Sequence
<220> FEATURE:
<223> OTHER INFORMATION: Additional sarbecovirus optimized region 1
      polypeptide (region 1 SARBECO-EG-2.2):

<400> SEQUENCE: 9

Asn Cys Leu Asp Asp Arg Cys Ile Leu His Cys Ala Asn Phe Asn Val
1               5                   10                  15

Leu Phe Ser Thr Val Phe Pro Pro Thr Ser Phe Gly Pro Leu Val Arg
            20                  25                  30

Lys Ile Phe Val Asp Gly Val Pro Phe Val Val Ser Thr Gly Tyr His
        35                  40                  45

Phe Arg Glu Leu Gly Val Val His Asn Gln Asp Val Asn Ile His Ser
    50                  55                  60

Ser Arg Leu Ser Phe Lys Glu Leu Leu Val Tyr Ala Ala Asp Pro Ala
65                  70                  75                  80

Met His Ala Ala Ser Gly Asn Leu Leu Leu Asp Lys Arg Thr Thr Cys
                85                  90                  95

Phe Ser Val Ala Ala Leu Thr Asn Ser Val Ala Phe Gln Thr Val Lys
            100                 105                 110

Pro Gly Asn Phe Asn Lys Asp Phe Tyr Asp Phe Ala Val Ser Lys Gly
        115                 120                 125

Phe Phe Lys Glu Gly Ser Ser Val Glu Leu Lys His Phe Phe Phe Ala
    130                 135                 140

Gln Asp Gly Asn Ala Ala Ile Ser Asp Tyr Asp Tyr Tyr Arg Tyr Asn
145                 150                 155                 160

Leu Pro Thr Met Cys Asp Ile Arg Gln Leu Leu Phe Val Val Glu Val
                165                 170                 175

Val Asp Lys Tyr Phe Asp Cys Tyr Asp Gly Gly Cys Ile Asn Ala Asn
            180                 185                 190

Gln Val Ile Val Asn Asn Leu Asp Lys Ser Ala Gly Phe Pro Phe Asn
        195                 200                 205

Lys Trp Gly Lys Ala Arg Leu Tyr Tyr Asp Ser Met Ser Tyr Glu Asp
    210                 215                 220

Gln Asp Ala Leu Phe Ala Tyr Thr Lys Arg Asn Val Leu Pro Thr Ile
225                 230                 235                 240

Thr Gln Met Asn Leu Lys Tyr Ala Ile Ser Ala Lys Asn Arg Ala Arg
                245                 250                 255

Thr Val Ala Gly Val Ser Ile Cys Ser Thr Met Thr Asn Arg Gln Phe
            260                 265                 270

His Gln Lys Leu Leu Lys Ser Ile Ala Ala Thr Arg Gly Ala Thr Val
        275                 280                 285

Val Ile Gly Thr Ser Lys Phe Tyr Gly Gly Trp Asn Asn Met Leu Lys
    290                 295                 300

Thr Val Tyr Ser Asp Val Glu Ser Pro His Leu Met Gly Trp Asp Tyr
305                 310                 315                 320
```

-continued

```
Pro Lys Cys Asp Arg Ala Met Pro Asn Met Leu Arg Ile Met Ala Ser
                325                 330                 335

Leu Val Leu Ala Arg Lys His Asn Thr Cys Cys Asn Leu Ser His Arg
            340                 345                 350

Phe Tyr Arg Leu Ala Asn Glu Cys Ala Gln Val Leu Ser Glu Met Val
        355                 360                 365

Met Cys Gly Gly Ser Leu Tyr Val Lys Pro Gly Gly Thr Ser Ser Gly
    370                 375                 380

Asp Ala Thr Thr Ala Tyr Ala Asn Ser Val Phe Asn Ile Cys Gln Ala
385                 390                 395                 400

Val Thr Ala Asn Val Asn Ala Leu Leu Ser Thr Asp Gly Asn Lys Ile
                405                 410                 415

Ala Asp Lys Tyr Val Arg Asn Leu Gln His Arg Leu Tyr Glu Cys Leu
            420                 425                 430

Tyr Arg Asn Arg Asp Val Asp Thr Asp Phe Val Asn Glu Phe Tyr Ala
        435                 440                 445

Tyr Leu Arg Lys His Phe Ser Met Met Ile Leu Ser Ala Ala Ala Val
    450                 455                 460

Val Cys Tyr Asn Ser Asn Tyr Ala Ala Gln Gly Leu Val Ala Ser Ile
465                 470                 475                 480

Lys Asn Phe Lys Ser Val Leu Tyr Tyr Gln Asn Asn Val Phe Met Ser
                485                 490                 495

Glu Ala Lys Cys Trp Thr Glu Thr Asp Leu Thr Arg Gly Pro His Glu
            500                 505                 510

Phe Cys Ser Gln His Thr Met Leu Val Lys Gln Gly Asp Asp Tyr Val
        515                 520                 525

Tyr Leu Pro Tyr Pro Asp Pro Ser Arg Ile Leu Gly Ala Gly Cys Phe
    530                 535                 540

Val Asp Asp Ile Val Lys Thr Asp Gly Thr Leu Met Ile Glu Arg Phe
545                 550                 555                 560

Val Ser Leu Ala Ile Asp Ala Tyr Pro Leu Thr Lys His Pro Asn Gln
                565                 570                 575

Glu Tyr Ala Asp Val Phe His Leu Tyr Leu Gln Tyr Ile Arg Lys Leu
            580                 585                 590

His Asp Glu Leu Thr Gly His Met Leu Asp Met Tyr Ser Val Met Leu
        595                 600                 605

Thr Asn Asp Asn Thr Ser Arg Tyr Trp Glu Pro Glu Phe Tyr Glu Ala
    610                 615                 620

Met Tyr Thr Pro His Thr Val Leu Gln Ala Val Gly Ala Cys Val Leu
625                 630                 635                 640

Cys Asn Ser Gln Thr Ser Leu Arg Cys Gly Ala Cys Ile Arg Arg Pro
                645                 650                 655

Phe Leu Cys Cys Lys Cys Cys Tyr Asp His Val Ile Ser Thr Ser His
            660                 665                 670

Lys Leu Val Leu Ser Val Asn Pro Tyr Val Cys Asn Ala Pro Gly Cys
        675                 680                 685

Asp Val Thr Asp Val Thr Gln Leu Tyr Leu Gly Gly Met Ser Tyr Tyr
    690                 695                 700

Cys Lys Leu His Lys Pro Pro Ile Ser Phe Pro Leu Cys Ala Asn Gly
705                 710                 715                 720

Gln Val Phe Gly Leu Tyr Lys Asn Thr Cys Val Gly Ser Asp Asn Val
                725                 730                 735
```

-continued

```
Thr Asp Phe Asn Ala Ile Ala Thr Cys Asp Trp Thr Asn Ala Gly Asp
            740                 745                 750

Tyr Ile Leu Ala Asn Thr Cys Thr Glu Arg Leu Lys Leu Phe Ala Ala
        755                 760                 765

Glu Thr Leu Lys Ala Thr Glu Glu Thr Phe Lys Leu Ser Tyr Gly Ile
    770                 775                 780

Ala Thr Val Arg Glu Val Leu Ser Asp Arg Glu Leu His Leu Ser Trp
785                 790                 795                 800

Glu Val Gly Lys Pro Arg Pro Pro Leu Asn Arg Asn Tyr Val Phe Thr
                805                 810                 815

Gly Tyr Arg Val Thr Lys Asn Ser Lys Val Gln Ile Gly Glu Tyr Thr
            820                 825                 830

Phe Glu Lys Gly Asp Tyr Gly Asp Ala Val Val Tyr Arg Gly Thr Thr
        835                 840                 845

Thr Tyr Lys Leu Asn Val Gly Asp Tyr Phe Val Leu Thr Ser His Thr
    850                 855                 860

Val Met Pro Leu Ser Ala Pro Thr Leu Val Pro Gln Glu His Tyr Val
865                 870                 875                 880

Arg Ile Thr Gly Leu Tyr Pro Thr Leu Asn Ile Ser Asp Glu Phe Ser
                885                 890                 895

Ser Asn Val Ala Asn Tyr Gln Lys Ile Gly Met Gln Lys Tyr Ser Thr
            900                 905                 910

Leu Gln Gly Pro Pro Gly Thr Gly Lys Ser His Phe Ala Ile Gly Leu
        915                 920                 925

Ala Leu Tyr Tyr Pro Ser Ala Arg Ile Val Tyr Thr Ala Cys Ser His
    930                 935                 940

Ala Ala Val Asp Ala Leu Cys Glu Lys Ala Leu Lys Tyr Leu Pro Ile
945                 950                 955                 960

Asp Lys Cys Ser Arg Ile Ile Pro Ala Arg Ala Arg Val Glu Cys Phe
                965                 970                 975

Asp Lys Phe Lys Val Asn Ser Thr Leu Glu Gln Tyr Val Phe Cys Thr
            980                 985                 990

Val Asn Ala Leu Pro Glu Thr Thr  Ala Asp Ile Val Val  Phe Asp Glu
        995                 1000                1005

Ile Ser  Met Ala Thr Asn Tyr  Asp Leu Ser Val Val  Asn Ala Arg
    1010                1015                1020

Leu Arg  Ala Lys His Tyr Val  Tyr Ile Gly Asp Pro  Ala Gln Leu
    1025                1030                1035

Pro Ala  Pro Arg Thr Leu Leu  Thr Lys Gly Thr Leu  Glu Pro Glu
    1040                1045                1050

Tyr Phe  Asn Ser Val Cys Arg  Leu Met Lys Thr Ile  Gly Pro Asp
    1055                1060                1065

Met Phe  Leu Gly Thr Cys Arg  Arg Cys Pro Ala Glu  Ile Val Asp
    1070                1075                1080

Thr Val  Ser Ala Leu Val Tyr  Asp Asn Lys Leu
    1085                1090
```

<210> SEQ ID NO 10
<211> LENGTH: 540
<212> TYPE: PRT
<213> ORGANISM: Artificial Sequence
<220> FEATURE:
<223> OTHER INFORMATION: Alternative SARS-CoV-2 nsp6-10 polypeptide
(region 2)

<400> SEQUENCE: 10

-continued

```
Gly Gly Lys Pro Cys Ile Lys Val Ala Thr Val Gln Ser Lys Met Ser
1               5                   10                  15

Asp Val Lys Cys Thr Ser Val Val Leu Leu Ser Val Leu Gln Gln Leu
            20                  25                  30

Arg Val Glu Ser Ser Ser Lys Leu Trp Ala Gln Cys Val Gln Leu His
        35                  40                  45

Asn Asp Ile Leu Leu Ala Lys Asp Thr Thr Glu Ala Phe Glu Lys Met
    50                  55                  60

Val Ser Leu Leu Ser Val Leu Leu Ser Met Gln Gly Ala Val Asp Ile
65                  70                  75                  80

Asn Lys Leu Cys Glu Glu Met Leu Asp Asn Arg Ala Thr Leu Gln Ala
                85                  90                  95

Ile Ala Ser Glu Phe Ser Ser Leu Pro Ser Tyr Ala Ala Phe Ala Thr
            100                 105                 110

Ala Gln Glu Ala Tyr Glu Gln Ala Val Ala Asn Gly Asp Ser Glu Val
        115                 120                 125

Val Leu Lys Lys Leu Lys Lys Ser Leu Asn Val Ala Lys Ser Glu Phe
    130                 135                 140

Asp Arg Asp Ala Ala Met Gln Arg Lys Leu Glu Lys Met Ala Asp Gln
145                 150                 155                 160

Ala Met Thr Gln Met Tyr Lys Gln Ala Arg Ser Glu Asp Lys Arg Ala
                165                 170                 175

Lys Val Thr Ser Ala Met Gln Thr Met Leu Phe Thr Met Leu Arg Lys
            180                 185                 190

Leu Asp Asn Asp Ala Leu Asn Asn Ile Ile Asn Asn Ala Arg Asp Gly
        195                 200                 205

Cys Val Pro Leu Asn Ile Ile Pro Leu Thr Thr Ala Ala Lys Leu Met
    210                 215                 220

Val Val Ile Pro Asp Tyr Asn Thr Tyr Lys Asn Thr Cys Asp Gly Thr
225                 230                 235                 240

Thr Phe Thr Tyr Ala Ser Ala Leu Trp Glu Ile Gln Gln Val Val Asp
                245                 250                 255

Ala Asp Ser Lys Ile Val Gln Leu Ser Glu Ile Ser Met Asp Asn Ser
            260                 265                 270

Pro Asn Leu Ala Trp Pro Leu Ile Val Thr Ala Leu Arg Ala Asn Ser
        275                 280                 285

Ala Val Lys Leu Gln Asn Asn Glu Leu Ser Pro Val Ala Leu Arg Gln
    290                 295                 300

Met Ser Cys Ala Ala Gly Thr Thr Gln Thr Ala Cys Thr Asp Asp Asn
305                 310                 315                 320

Ala Leu Ala Tyr Tyr Asn Thr Thr Lys Gly Gly Arg Phe Val Leu Ala
                325                 330                 335

Leu Leu Ser Asp Leu Gln Asp Leu Lys Trp Ala Arg Phe Pro Lys Ser
            340                 345                 350

Asp Gly Thr Gly Thr Ile Tyr Thr Glu Leu Glu Pro Pro Cys Arg Phe
        355                 360                 365

Val Thr Asp Thr Pro Lys Gly Pro Lys Val Lys Tyr Leu Tyr Phe Ile
    370                 375                 380

Lys Gly Leu Asn Asn Leu Asn Arg Gly Met Val Leu Gly Ser Leu Ala
385                 390                 395                 400

Ala Thr Val Arg Leu Gln Ala Gly Asn Ala Thr Glu Val Pro Ala Asn
                405                 410                 415
```

-continued

```
Ser Thr Val Leu Ser Phe Cys Ala Phe Ala Val Asp Ala Ala Lys Ala
            420                 425                 430

Tyr Lys Asp Tyr Leu Ala Ser Gly Gly Gln Pro Ile Thr Asn Cys Val
        435                 440                 445

Lys Met Leu Cys Thr His Thr Gly Thr Gly Gln Ala Ile Thr Val Thr
    450                 455                 460

Pro Glu Ala Asn Met Asp Gln Glu Ser Phe Gly Gly Ala Ser Cys Cys
465                 470                 475                 480

Leu Tyr Cys Arg Cys His Ile Asp His Pro Asn Pro Lys Gly Phe Cys
                485                 490                 495

Asp Leu Lys Gly Lys Tyr Val Gln Ile Pro Thr Thr Cys Ala Asn Asp
            500                 505                 510

Pro Val Gly Phe Thr Leu Lys Asn Thr Val Cys Thr Val Cys Gly Met
        515                 520                 525

Trp Lys Gly Tyr Gly Cys Ser Cys Asp Gln Leu Arg
    530                 535                 540


<210> SEQ ID NO 11
<211> LENGTH: 540
<212> TYPE: PRT
<213> ORGANISM: Artificial Sequence
<220> FEATURE:
<223> OTHER INFORMATION: SARS-CoV-2 region 2 optimized polypeptide
      (region 2 SARS-CoV2-EG-2.1)

<400> SEQUENCE: 11

Gly Gly Lys Pro Cys Val Lys Val Ala Thr Val Gln Ser Lys Ile Ser
1               5                   10                  15

Asp Val Lys Cys Thr Ser Val Val Leu Leu Leu Val Leu Gln Gln Leu
            20                  25                  30

Arg Val Glu Ser Leu Ser Lys Leu Trp Ala Gln Cys Val Gln Leu His
        35                  40                  45

Asn Asp Ile Ile Leu Ala Lys Asp Thr Thr Glu Ala Phe Gly Lys Met
    50                  55                  60

Val Ser Leu Leu Ser Val Leu Leu Ser Met Gln Arg Ala Val Asp Ile
65                  70                  75                  80

Asn Lys Leu Cys Glu Glu Ile Leu Asp Asn Arg Ala Thr Leu Gln Ser
                85                  90                  95

Ile Ala Ser Glu Phe Ser Ser Leu Ser Ser Tyr Ala Ala Phe Ala Thr
            100                 105                 110

Ala Gln Glu Ala Tyr Glu Arg Ala Val Ala Asn Gly Asp Ser Glu Val
        115                 120                 125

Phe Leu Lys Lys Leu Lys Lys Ser Leu Asn Val Ala Lys Ser Glu Phe
    130                 135                 140

Asp Cys Asp Ala Ala Met Gln Arg Lys Leu Glu Asn Met Ala Asp Gln
145                 150                 155                 160

Ala Met Thr Gln Met Tyr Lys Gln Val Arg Ser Glu Asp Lys Arg Ala
                165                 170                 175

Lys Val Thr Ser Ala Met Gln Ile Met Leu Phe Thr Met Leu Arg Lys
            180                 185                 190

Phe Asp Asn Asp Ala Leu Asn Asn Ile Val Asn Asn Ala Arg Asp Gly
        195                 200                 205

Cys Val Pro Leu Asn Ile Ile Pro Phe Thr Thr Ala Ala Lys Leu Met
    210                 215                 220

Val Val Ile Ser Asp Tyr Asn Thr Tyr Lys Asn Thr Cys Asp Gly Ile
225                 230                 235                 240
```

-continued

```
Thr Phe Thr Tyr Ala Ser Ala Leu Trp Glu Ile Gln His Val Val Asp
                245                 250                 255

Ala Asp Ser Lys Ile Val Gln Phe Ser Glu Ile Ser Met Asp Asn Ser
            260                 265                 270

Ser Asn Leu Ala Trp Pro Leu Ile Val Ile Ala Leu Arg Ala Asn Ser
        275                 280                 285

Ala Val Lys Leu Gln Asn Asn Glu Leu Ser Pro Val Val Leu Arg Gln
    290                 295                 300

Met Ser Cys Ala Ala Gly Thr Thr Gln Thr Ala Cys Ile Asp Asp Asn
305                 310                 315                 320

Ala Leu Ala Tyr Tyr Asn Thr Ile Lys Gly Gly Arg Phe Val Leu Ala
                325                 330                 335

Leu Leu Ser Asn Leu Gln Asp Leu Lys Trp Ala Arg Phe Pro Lys Ser
            340                 345                 350

Asp Gly Thr Gly Thr Val Tyr Thr Glu Leu Glu Pro Pro Cys Gly Phe
        355                 360                 365

Val Thr Asp Thr Pro Lys Gly Leu Lys Val Lys Tyr Leu Tyr Phe Ile
    370                 375                 380

Arg Gly Leu Asn Asn Leu Asn Arg Gly Ile Val Leu Gly Ser Leu Ala
385                 390                 395                 400

Ala Thr Val Arg Leu Gln Ala Gly Lys Ala Thr Glu Val Pro Ala Asn
                405                 410                 415

Ser Ile Val Leu Ser Phe Cys Ala Phe Ala Ile Asp Ala Ala Lys Ala
            420                 425                 430

Tyr Lys Asp Tyr Leu Val Ser Gly Gly Gln Pro Ile Thr Asn Cys Val
        435                 440                 445

Lys Met Leu Cys Thr His Ile Gly Thr Gly Gln Ala Ile Thr Val Ile
    450                 455                 460

Pro Glu Ala Asn Met Asp Gln Glu Ser Phe Gly Gly Ala Ser Cys Cys
465                 470                 475                 480

Met Tyr Cys Arg Cys His Ile Asp His Pro Asp Pro Lys Gly Phe Cys
                485                 490                 495

Asp Leu Lys Gly Lys Tyr Val Gln Ile Pro Thr Ile Cys Ala Asn Asp
            500                 505                 510

Pro Val Gly Phe Ile Leu Lys Asn Thr Val Cys Thr Val Cys Ser Met
        515                 520                 525

Trp Lys Gly Tyr Gly Cys Ser Cys Asp Gln Leu Cys
    530                 535                 540
```

<210> SEQ ID NO 12
<211> LENGTH: 540
<212> TYPE: PRT
<213> ORGANISM: Artificial Sequence
<220> FEATURE:
<223> OTHER INFORMATION: Additional SARS-CoV-2 optimized region 2 polypeptide (region 2 SARS-CoV2-EG-2.2)

<400> SEQUENCE: 12

```
Gly Gly Lys Pro Cys Ile Lys Val Ala Thr Val Gln Ser Lys Thr Ser
1               5                   10                  15

Asp Val Lys Cys Thr Ser Val Val Leu Leu Ser Val Phe Gln Gln Leu
            20                  25                  30

Arg Val Glu Ser Ser Phe Lys Leu Trp Ala Gln Cys Val Gln Leu His
        35                  40                  45

Asn Asp Ile Leu Leu Ala Arg Asp Thr Thr Glu Ala Phe Glu Lys Met
```

-continued

```
    50                  55                  60

Val Ser Leu Leu Ser Val Leu Phe Ser Met Gln Gly Ala Val Asp Ile
65                  70                  75                  80

Asn Lys Phe Cys Glu Glu Met Leu Asp Asn Arg Ala Ile Leu Gln Ala
                85                  90                  95

Ile Ala Ser Glu Phe Ser Ser Leu Pro Ser Tyr Ala Ala Leu Ala Thr
            100                 105                 110

Ala Gln Glu Ala Tyr Glu Gln Ala Val Val Asn Gly Asp Ser Glu Val
        115                 120                 125

Val Leu Lys Asn Leu Lys Lys Ser Leu Asn Val Ala Lys Ser Glu Phe
    130                 135                 140

Asp Leu Asp Ala Ala Met Gln Arg Lys Leu Glu Lys Met Ser Asp Gln
145                 150                 155                 160

Ala Met Thr Gln Met Tyr Lys Gln Ala Lys Ser Glu Asp Lys Arg Ala
                165                 170                 175

Lys Val Ile Ser Ala Met Gln Thr Met Leu Phe Thr Met Phe Arg Lys
            180                 185                 190

Leu Asp Asn Asp Ala Leu Asn Asn Ile Ile Asp Asn Ala Arg Asp Gly
        195                 200                 205

Cys Val Pro Leu Asn Ile Ile Pro Leu Ile Thr Ala Ala Lys Leu Met
    210                 215                 220

Val Val Thr Pro Asp Tyr Asn Thr Tyr Lys Asn Met Cys Asp Gly Thr
225                 230                 235                 240

Thr Phe Ile Tyr Ala Ser Ala Leu Trp Glu Ile Gln Gln Val Val Asn
                245                 250                 255

Ala Asp Ser Lys Ile Val Gln Leu Ser Glu Val Ser Met Asp Asn Ser
            260                 265                 270

Pro Asn Leu Ala Trp Pro Leu Val Val Thr Ala Leu Arg Ala Asn Ser
        275                 280                 285

Ala Ile Lys Leu Gln Asn Asn Glu Leu Ser Pro Ile Ala Leu Arg Gln
    290                 295                 300

Met Ser Cys Ala Ala Gly Thr Ile Gln Thr Ala Cys Thr Asp Asp Asn
305                 310                 315                 320

Ala Leu Val Tyr Tyr Asn Thr Thr Lys Gly Gly Arg Phe Val Phe Ala
                325                 330                 335

Leu Leu Ser Asp Leu Gln Asp Leu Lys Trp Ala Arg Phe Ser Lys Ser
            340                 345                 350

Asp Gly Thr Gly Thr Ile Tyr Ile Glu Leu Glu Pro Pro Cys Arg Phe
        355                 360                 365

Val Thr Asp Thr Leu Lys Gly Pro Lys Val Lys Tyr Leu Tyr Phe Ile
    370                 375                 380

Lys Arg Leu Asn Asn Leu Asn Arg Gly Met Val Leu Gly Ser Leu Ala
385                 390                 395                 400

Ala Ile Val Arg Leu Gln Ala Gly Asn Ala Ile Glu Val Pro Ala Asn
                405                 410                 415

Ser Thr Val Leu Phe Phe Cys Ala Phe Ala Val Asp Ala Ser Lys Ala
            420                 425                 430

Tyr Lys Asp Tyr Leu Ala Ser Gly Gly Gln Pro Ile Ile Asn Cys Val
        435                 440                 445

Lys Met Leu Cys Thr His Thr Gly Ile Gly Gln Ala Ile Thr Val Thr
    450                 455                 460

Pro Glu Ala Asn Met Glu Gln Glu Ser Phe Gly Gly Ala Ser Cys Cys
465                 470                 475                 480
```

```
Leu Tyr Cys Arg Cys His Ile Asp His Ser Asn Pro Lys Gly Phe Cys
                485                 490                 495

Asp Leu Lys Gly Arg Tyr Val Gln Ile Pro Thr Thr Cys Val Asn Asp
            500                 505                 510

Pro Val Gly Phe Thr Leu Lys Asn Thr Val Cys Thr Ile Cys Gly Met
        515                 520                 525

Trp Lys Gly Tyr Gly Cys Gly Cys Asp Gln Leu Arg
    530                 535                 540


<210> SEQ ID NO 13
<211> LENGTH: 540
<212> TYPE: PRT
<213> ORGANISM: Artificial Sequence
<220> FEATURE:
<223> OTHER INFORMATION: sarbecovirus region 2 optimized polypeptide
      (region 2 SARBECO-EG-2.1):

<400> SEQUENCE: 13

Gly Gly Lys Pro Cys Ile Lys Val Ala Thr Val Gln Ser Lys Met Ser
1               5                   10                  15

Asp Val Lys Cys Thr Ser Val Val Leu Leu Ser Val Leu Gln Gln Leu
            20                  25                  30

Arg Val Glu Ser Ser Ser Lys Leu Trp Ala Gln Cys Val Gln Leu His
        35                  40                  45

Asn Asp Ile Leu Leu Ala Lys Asp Thr Thr Glu Ala Phe Glu Lys Met
    50                  55                  60

Val Ser Leu Leu Ser Val Leu Leu Ser Met Gln Gly Ala Val Asp Ile
65                  70                  75                  80

Asn Arg Leu Cys Glu Glu Met Leu Asp Asn Arg Ala Thr Leu Gln Ala
                85                  90                  95

Ile Ala Ser Glu Phe Ser Ser Leu Pro Ser Tyr Ala Ala Tyr Ala Thr
            100                 105                 110

Ala Gln Glu Ala Tyr Glu Gln Ala Val Ser Asn Gly Asp Ser Glu Val
        115                 120                 125

Val Leu Lys Lys Leu Lys Lys Ser Leu Asn Val Ala Lys Ser Glu Phe
    130                 135                 140

Asp His Asp Ala Ala Met Gln Arg Lys Leu Glu Lys Met Ala Asp Gln
145                 150                 155                 160

Ala Met Thr Gln Met Tyr Lys Gln Ala Arg Ser Glu Asp Lys Arg Ala
                165                 170                 175

Lys Val Thr Ser Ala Met Gln Thr Met Leu Phe Thr Met Leu Arg Lys
            180                 185                 190

Leu Asp Asn Asp Ala Leu Asn Asn Ile Ile Asn Asn Ala Arg Asp Gly
        195                 200                 205

Cys Val Pro Leu Asn Ile Ile Pro Leu Thr Thr Ala Ala Lys Leu Met
    210                 215                 220

Val Val Val Pro Asp Tyr Gly Thr Tyr Lys Asn Thr Cys Asp Gly Asn
225                 230                 235                 240

Thr Phe Thr Tyr Ala Ser Ala Leu Trp Glu Ile Gln Gln Val Val Asp
                245                 250                 255

Ala Asp Ser Lys Ile Val Gln Leu Ser Glu Ile Asn Met Asp Asn Ser
            260                 265                 270

Pro Asn Leu Ala Trp Pro Leu Ile Val Thr Ala Leu Arg Ala Asn Ser
        275                 280                 285

Ala Val Lys Leu Gln Asn Asn Glu Leu Ser Pro Val Ala Leu Arg Gln
```

```
    290                 295                 300

Met Ser Cys Ala Ala Gly Thr Thr Gln Thr Ala Cys Asn Glu Asp Asn
305                 310                 315                 320

Ala Leu Ala Tyr Tyr Asn Asn Ser Lys Gly Gly Arg Phe Val Leu Ala
                325                 330                 335

Leu Leu Ser Asp His Gln Asp Leu Lys Trp Ala Arg Phe Pro Lys Ser
            340                 345                 350

Asp Gly Thr Gly Thr Ile Tyr Thr Glu Leu Glu Pro Pro Cys Arg Phe
        355                 360                 365

Val Thr Asp Thr Pro Lys Gly Pro Lys Val Lys Tyr Leu Tyr Phe Ile
    370                 375                 380

Lys Gly Leu Asn Asn Leu Asn Arg Gly Met Val Leu Gly Ser Leu Ala
385                 390                 395                 400

Ala Thr Val Arg Leu Gln Ala Gly Asn Ala Thr Glu Val Pro Ala Asn
                405                 410                 415

Ser Thr Val Leu Ser Phe Cys Ala Phe Ala Val Asp Pro Ala Lys Ala
            420                 425                 430

Tyr Lys Asp Tyr Leu Ser Ser Gly Gly Gln Pro Ile Thr Asn Cys Val
        435                 440                 445

Lys Met Leu Cys Thr His Thr Gly Thr Gly Gln Ala Ile Thr Val Thr
    450                 455                 460

Pro Glu Ala Asn Met Asp Gln Glu Ser Phe Gly Gly Ala Ser Cys Cys
465                 470                 475                 480

Leu Tyr Cys Arg Cys His Ile Asp His Pro Asn Pro Lys Gly Tyr Cys
                485                 490                 495

Glu Leu Lys Gly Lys Tyr Val Gln Ile Pro Thr Thr Cys Ala Asn Asp
            500                 505                 510

Pro Val Gly Phe Thr Leu Arg Asn Thr Val Cys Thr Val Cys Gly Met
        515                 520                 525

Trp Lys Gly Tyr Gly Cys Ser Cys Asp Gln Leu Arg
    530                 535                 540


<210> SEQ ID NO 14
<211> LENGTH: 540
<212> TYPE: PRT
<213> ORGANISM: Artificial Sequence
<220> FEATURE:
<223> OTHER INFORMATION: Additional sarbecovirus region 2 optimized
      polypeptide (region 2 SARBECO-EG-2.2)

<400> SEQUENCE: 14

Gly Gly Lys Pro Cys Ile Lys Val Ala Thr Val Gln Ser Lys Met Ser
1               5                   10                  15

Asp Val Lys Cys Thr Ser Val Val Leu Leu Ser Val Leu Gln Gln Leu
            20                  25                  30

Arg Val Glu Ser Ser Ser Lys Leu Trp Ala Gln Cys Val Gln Leu His
        35                  40                  45

Asn Asp Ile Leu Leu Ala Lys Asp Thr Thr Glu Ala Phe Glu Lys Met
    50                  55                  60

Val Ser Leu Leu Ser Val Leu Leu Ser Met Gln Gly Ala Val Asp Ile
65                  70                  75                  80

Asn Arg Leu Cys Glu Glu Met Leu Asp Asn Arg Ala Thr Leu Gln Ala
                85                  90                  95

Ile Ala Ser Glu Phe Ser Ser Leu Pro Ser Tyr Ala Ala Phe Ala Thr
            100                 105                 110
```

-continued

```
Ala Gln Glu Ala Tyr Glu Gln Ala Val Ala Asn Gly Asp Ser Glu Val
        115                 120                 125

Val Leu Lys Lys Leu Lys Lys Ser Leu Asn Val Ala Lys Ser Glu Phe
    130                 135                 140

Asp Arg Asp Ala Ala Met Gln Arg Lys Leu Glu Lys Met Ala Asp Gln
145                 150                 155                 160

Ala Met Thr Gln Met Tyr Lys Gln Ala Arg Ser Glu Asp Lys Arg Ala
                165                 170                 175

Lys Val Thr Ser Ala Met Gln Thr Met Leu Phe Thr Met Leu Arg Lys
            180                 185                 190

Leu Asp Asn Asp Ala Leu Asn Asn Ile Ile Asn Asn Ala Arg Asp Gly
        195                 200                 205

Cys Val Pro Leu Asn Ile Ile Pro Leu Thr Thr Ala Ala Lys Leu Met
    210                 215                 220

Val Val Val Pro Asp Tyr Asn Thr Tyr Lys Asn Thr Cys Glu Gly Ser
225                 230                 235                 240

Thr Phe Thr Tyr Ala Ser Ala Leu Trp Glu Ile Gln Gln Val Val Asp
                245                 250                 255

Ala Asp Ser Lys Ile Val Pro Leu Ser Glu Ile Asn Met Asp Asn Ser
            260                 265                 270

Gln Asn Leu Ala Trp Pro Leu Ile Val Thr Ala Leu Arg Ala Asn Ser
        275                 280                 285

Ala Val Lys Leu Gln Asn Asn Glu Leu Ser Pro Val Ala Leu Arg Gln
    290                 295                 300

Met Ser Cys Ala Ala Gly Thr Thr Gln Thr Ala Cys Thr Asp Asp Asn
305                 310                 315                 320

Ala Leu Ala Tyr Tyr Asn Thr Ser Lys Gly Gly Arg Phe Val Leu Ala
                325                 330                 335

Leu Leu Ser Asp Leu Gln Asp Leu Lys Trp Ala Arg Phe Pro Lys Ser
            340                 345                 350

Asp Gly Thr Gly Thr Ile Tyr Thr Glu Leu Glu Pro Pro Cys Arg Phe
        355                 360                 365

Val Thr Asp Thr Pro Lys Gly Pro Lys Val Lys Tyr Leu Tyr Phe Ile
    370                 375                 380

Lys Gly Leu Asn Asn Leu Asn Arg Gly Met Val Leu Gly Ser Leu Ala
385                 390                 395                 400

Ala Thr Val Arg Leu Gln Ala Gly Asn Ala Thr Glu Val Pro Ala Asn
                405                 410                 415

Ser Thr Val Leu Ser Phe Cys Ala Phe Ala Val Asp Ala Ser Lys Ala
            420                 425                 430

Tyr Arg Asp Tyr Leu Ala Ser Gly Gly Gln Pro Ile Thr Asn Cys Val
        435                 440                 445

Lys Met Leu Cys Thr His Thr Gly Thr Gly Gln Ala Ile Thr Val Thr
    450                 455                 460

Pro Glu Ala Asn Met Asp Gln Glu Ser Phe Gly Gly Ala Ser Cys Cys
465                 470                 475                 480

Leu Tyr Cys Arg Cys His Ile Asp His Pro Asn Pro Lys Gly Phe Cys
                485                 490                 495

Asp Leu Lys Gly Lys Tyr Val Gln Ile Pro Thr Thr Cys Ala Asn Asp
            500                 505                 510

Pro Val Gly Phe Thr Leu Arg Asn Thr Val Cys Thr Val Cys Gly Met
        515                 520                 525

Trp Lys Gly Tyr Gly Cys Ser Cys Asp Gln Leu Arg
```

530    535    540

<210> SEQ ID NO 15
<211> LENGTH: 3288
<212> TYPE: DNA
<213> ORGANISM: Artificial Sequence
<220> FEATURE:
<223> OTHER INFORMATION: Nucleic acid encoding modified conserved region
    SARS-CoV-2 polypeptide spanning RNA-dependent RNA polymerase and
    helicase proteins (region 1)

<400> SEQUENCE: 15
atgaactgcc tggacgaccg ctgcatcctg cactgcgcca acttcaacgt gctgttctcc 60
accgtgttcc cccccacctc cttcggcccc ctggtgcgca agatcttcgt ggacggcgtg 120
cccttcgtgg tgtccaccgg ctaccacttc cgcgagctgg gcgtggtgca caaccaggac 180
gtgaacctgc actcctcccg cctgtccttc aaggagctgc tggtgtacgc cgccgacccc 240
gccatgcacg ccgcctccgg caacctgctg ctggacaagc gcaccacctg cttctccgtg 300
gccgccctga ccaacaacgt ggccttccag accgtgaagc ccggcaactt caacaaggac 360
ttctacgact tcgccgtgtc caagggcttc ttcaaggagg gctcctccgt ggagctgaag 420
cacttcttct tcgcccagga cggcaacgcc gccatctccg actacgacta ctaccgctac 480
aacctgccca ccatgtgcga catccgccag ctgctgttcg tggtggaggt ggtggacaag 540
tacttcgact gctacgacgg cggctgcatc aacgccaacc aggtgatcgt gaacaacctg 600
gacaagtccg ccggcttccc cttcaacaag tggggcaagg cccgcctgta ctacgactcc 660
atgtcctacg aggaccagga cgccctgttc gcctacacca agcgcaacgt gatccccacc 720
atcacccaga tgaacctgaa gtacgccatc tccgccaaga accgcgcccg caccgtggcc 780
ggcgtgtcca tctgctccac catgaccaac cgccagttcc accagaagct gctgaagtcc 840
atcgccgcca cccgcggcgc caccgtggtg atcggcacct ccaagttcta cggcggctgg 900
cacaacatgc tgaagaccgt gtactccgac gtggagaacc cccacctgat gggctgggac 960
taccccaagt gcgaccgcgc catgcccaac atgctgcgca tcatggcctc cctggtgctg 1020
gcccgcaagc acaccacctg ctgctccctg tcccaccgct tctaccgcct ggccaacgag 1080
tgcgcccagg tgctgtccga gatggtgatg tgcggcggct ccctgtacgt gaagcccggc 1140
ggcacctcct ccggcgacgc caccaccgcc tacgccaact ccgtgttcaa catctgccag 1200
gccgtgaccg ccaacgtgaa cgccctgctg tccaccgacg gcaacaagat cgccgacaag 1260
tacgtgcgca acctgcagca ccgcctgtac gagtgcctgt accgcaaccg cgacgtggac 1320
accgacttcg tgaacgagtt ctacgcctac ctgcgcaagc acttctccat gatgatcctg 1380
tccgccgccg ccgtggtgtg cttcaactcc acctacgcct cccagggcct ggtggcctcc 1440
atcaagaact tcaagtccgt gctgtactac cagaacaacg tgttcatgtc cgaggccaag 1500
tgctggaccg agaccgacct gaccaagggc ccccacgagt tctgctccca gcacaccatg 1560
ctggtgaagc agggcgacga ctacgtgtac ctgccctacc ccgacccctc ccgcatcctg 1620
ggcgccggct gcttcgtgga cgacatcgtg aagaccgacg gcaccctgat gatcgagcgg 1680
ttcgtgtccc tggccatcga cgcctacccc ctgaccaagc accccaacca ggagtacgcc 1740
gacgtgttcc acctgtacct gcagtacatc cgcaagctgc acgacgagct gaccggccac 1800
atgctggaca tgtactccgt gatgctgacc aacgacaaca cctcccgcta ctgggagccc 1860
gagttctacg aggccatgta caccccccac accgtgctgc aggccgtggg cgcctgcgtg 1920
ctgtgcaact cccagacctc cctgcgctgc ggcgcctgca tccgccgccc cttcctgtgc 1980
tgcaagtgct gctacgacca cgtgatctcc acctcccaca agctggtgct gtccgtgaac 2040
ccctacgtgt gcaacgcccc cggctgcgac gtgaccgacg tgacccagct gtacctgggc 2100
ggcatgtcct actactgcaa gtcccacaag cccccccatct ccttcccccct gtgcgccaac 2160 ggccaggtgt tcggcctgta caagaacacc tgcgtgggct ccgacaacgt gaccgacttc 2220
aacgccatcg ccacctgcga ctggaccaac gccggcgact acatcctggc caacacctgc 2280
accgagcgcc tgaagctgtt cgccgccgag accctgaagg ccaccgagga gaccttcaag 2340
ctgtcctacg gcatcgccac cgtgcgcgag gtgctgtccg accgcgagct gcacctgtcc 2400
tgggaggtgg gcaagccccg cccccccctg aaccgcaact acgtgttcac cggctaccgc 2460
gtgaccaaga actccaaggt gcagatcggc gagtacacct tcgagaaggg cgactacggc 2520
gacgccgtgg tgtaccgcgg caccaccacc tacaagctga acgtgggcga ctacttcgtg 2580
ctgacctccc acaccgtgat gcccctgtcc gcccccaccc tggtgcccca ggagcactac 2640
gtgcgcatca ccggcctgta ccccaccctg aacatctccg acgagttctc ctccaacgtg 2700
gccaactacc agaaggtggg catgcagaag tactccaccc tgcagggccc ccccggcacc 2760
ggcaagtccc acttcgccat cggcctggcc ctgtactacc cctccgcccg catcgtgtac 2820
accgcctgct cccacgccgc cgtggacgcc ctgtgcgaga aggccctgaa gtacctgccc 2880
atcgacaagt gctcccgcat catccccgcc cgcgcccgcg tggagtgctt cgacaagttc 2940
aaggtgaact ccaccctgga gcagtacgtg ttctgcaccg tgaacgccct gcccgagacc 3000
accgccgaca tcgtggtgtt cgacgagatc tccatggcca ccaactacga cctgtccgtg 3060
gtgaacgccc gcctgcgcgc caagcactac gtgtacatcg gcgaccccgc ccagctgccc 3120
gccccccgca ccctgctgac caagggcacc ctggagcccg agtacttcaa ctccgtgtgc 3180
cgcctgatga agaccatcgg ccccgacatg ttcctgggca cctgccgccg ctgccccgcc 3240
gagatcgtgg acaccgtgtc cgccctggtg tacgacaaca agctgtaa 3288

<210> SEQ ID NO 16
<211> LENGTH: 609
<212> TYPE: DNA
<213> ORGANISM: Artificial Sequence
<220> FEATURE:
<223> OTHER INFORMATION: Nucleic acid encoding conserved region SARS-CoV-2 polypeptide from helicase

<400> SEQUENCE: 16
atggagttct cctccaacgt ggccaactac cagaaggtgg gcatgcagaa gtactccacc 60
ctgcagggcc cccccggcac cggcaagtcc cacttcgcca tcggcctggc cctgtactac 120
ccctccgccc gcatcgtgta caccgcctgc tcccacgccg ccgtggacgc cctgtgcgag 180
aaggccctga agtacctgcc catcgacaag tgctcccgca tcatccccgc ccgcgcccgc 240
gtggagtgct tcgacaagtt caaggtgaac tccaccctgg agcagtacgt gttctgcacc 300
gtgaacgccc tgcccgagac caccgccgac atcgtggtgt tcgacgagat ctccatggcc 360
accaactacg acctgtccgt ggtgaacgcc cgcctgcgcg ccaagcacta cgtgtacatc 420
ggcgaccccg cccagctgcc cgccccccgc accctgctga ccaagggcac cctggagccc 480
gagtacttca actccgtgtg ccgcctgatg aagaccatcg gccccgacat gttcctgggc 540
acctgccgcc gctgccccgc cgagatcgtg gacaccgtgt ccgccctggt gtacgacaac 600
aagctgtaa 609

-continued

<210> SEQ ID NO 17
<211> LENGTH: 618
<212> TYPE: DNA
<213> ORGANISM: Artificial Sequence
<220> FEATURE:
<223> OTHER INFORMATION: Nucleic acid encoding conserved region
SARS-CoV-2 polypeptide from RNA-dependent RNA polymerase

<400> SEQUENCE: 17
atgttccaga ccgtgaagcc cggcaacttc aacaaggact tctacgactt cgccgtgtcc 60
aagggcttct tcaaggaggg ctcctccgtg gagctgaagc acttcttctt cgcccaggac 120
ggcaacgccg ccatctccga ctacgactac taccgctaca acctgcccac catgtgcgac 180
atccgccagc tgctgttcgt ggtggaggtg gtggacaagt acttcgactg ctacgacggc 240
ggctgcatca acgccaacca ggtgatcgtg aacaacctgg acaagtccgc cggcttcccc 300
ttcaacaagt ggggcaaggc ccgcctgtac tacgactcca tgtcctacga ggaccaggac 360
gccctgttcg cctacaccaa gcgcaacgtg atccccacca tcacccagat gaacctgaag 420
tacgccatct ccgccaagaa ccgcgcccgc accgtggccg gcgtgtccat ctgctccacc 480
atgaccaacc gccagttcca ccagaagctg ctgaagtcca tcgccgccac ccgcggcgcc 540
accgtggtga tcggcacctc caagttctac ggcggctggc acaacatgct gaagaccgtg 600
tactccgacg tggagtaa 618

<210> SEQ ID NO 18
<211> LENGTH: 1642
<212> TYPE: PRT
<213> ORGANISM: Artificial Sequence
<220> FEATURE:
<223> OTHER INFORMATION: COVconsv amino acid sequence

<400> SEQUENCE: 18

Met Asn Cys Leu Asp Asp Arg Cys Ile Leu His Cys Ala Asn Phe Asn
1               5                   10                  15

Val Leu Phe Ser Thr Val Phe Pro Pro Thr Ser Phe Gly Pro Leu Val
            20                  25                  30

Arg Lys Ile Phe Val Asp Gly Val Pro Phe Val Val Ser Thr Gly Tyr
        35                  40                  45

His Phe Arg Glu Leu Gly Val Val His Asn Gln Asp Val Asn Leu His
    50                  55                  60

Ser Ser Arg Leu Ser Phe Lys Glu Leu Leu Val Tyr Ala Ala Asp Pro
65                  70                  75                  80

Ala Met His Ala Ala Ser Gly Asn Leu Leu Leu Asp Lys Arg Thr Thr
                85                  90                  95

Cys Phe Ser Val Ala Ala Leu Thr Asn Asn Val Ala Phe Gln Thr Val
            100                 105                 110

Lys Pro Gly Asn Phe Asn Lys Asp Phe Tyr Asp Phe Ala Val Ser Lys
        115                 120                 125

Gly Phe Phe Lys Glu Gly Ser Ser Val Glu Leu Lys His Phe Phe Phe
    130                 135                 140

Ala Gln Asp Gly Asn Ala Ala Ile Ser Asp Tyr Asp Tyr Tyr Arg Tyr
145                 150                 155                 160

Asn Leu Pro Thr Met Cys Asp Ile Arg Gln Leu Leu Phe Val Val Glu
                165                 170                 175

Val Val Asp Lys Tyr Phe Asp Cys Tyr Asp Gly Gly Cys Ile Asn Ala
            180                 185                 190

Asn Gln Val Ile Val Asn Asn Leu Asp Lys Ser Ala Gly Phe Pro Phe

```
        195                 200                 205

Asn Lys Trp Gly Lys Ala Arg Leu Tyr Tyr Asp Ser Met Ser Tyr Glu
    210                 215                 220

Asp Gln Asp Ala Leu Phe Ala Tyr Thr Lys Arg Asn Val Ile Pro Thr
225                 230                 235                 240

Ile Thr Gln Met Asn Leu Lys Tyr Ala Ile Ser Ala Lys Asn Arg Ala
                245                 250                 255

Arg Thr Val Ala Gly Val Ser Ile Cys Ser Thr Met Thr Asn Arg Gln
            260                 265                 270

Phe His Gln Lys Leu Leu Lys Ser Ile Ala Ala Thr Arg Gly Ala Thr
        275                 280                 285

Val Val Ile Gly Thr Ser Lys Phe Tyr Gly Gly Trp His Asn Met Leu
    290                 295                 300

Lys Thr Val Tyr Ser Asp Val Glu Asn Pro His Leu Met Gly Trp Asp
305                 310                 315                 320

Tyr Pro Lys Cys Asp Arg Ala Met Pro Asn Met Leu Arg Ile Met Ala
                325                 330                 335

Ser Leu Val Leu Ala Arg Lys His Thr Thr Cys Cys Ser Leu Ser His
            340                 345                 350

Arg Phe Tyr Arg Leu Ala Asn Glu Cys Ala Gln Val Leu Ser Glu Met
        355                 360                 365

Val Met Cys Gly Gly Ser Leu Tyr Val Lys Pro Gly Gly Thr Ser Ser
    370                 375                 380

Gly Asp Ala Thr Thr Ala Tyr Ala Asn Ser Val Phe Asn Ile Cys Gln
385                 390                 395                 400

Ala Val Thr Ala Asn Val Asn Ala Leu Leu Ser Thr Asp Gly Asn Lys
                405                 410                 415

Ile Ala Asp Lys Tyr Val Arg Asn Leu Gln His Arg Leu Tyr Glu Cys
            420                 425                 430

Leu Tyr Arg Asn Arg Asp Val Asp Thr Asp Phe Val Asn Glu Phe Tyr
        435                 440                 445

Ala Tyr Leu Arg Lys His Phe Ser Met Met Ile Leu Ser Ala Ala Ala
    450                 455                 460

Val Val Cys Phe Asn Ser Thr Tyr Ala Ser Gln Gly Leu Val Ala Ser
465                 470                 475                 480

Ile Lys Asn Phe Lys Ser Val Leu Tyr Tyr Gln Asn Asn Val Phe Met
                485                 490                 495

Ser Glu Ala Lys Cys Trp Thr Glu Thr Asp Leu Thr Lys Gly Pro His
            500                 505                 510

Glu Phe Cys Ser Gln His Thr Met Leu Val Lys Gln Gly Asp Asp Tyr
        515                 520                 525

Val Tyr Leu Pro Tyr Pro Asp Pro Ser Arg Ile Leu Gly Ala Gly Cys
    530                 535                 540

Phe Val Asp Asp Ile Val Lys Thr Asp Gly Thr Leu Met Ile Glu Arg
545                 550                 555                 560

Phe Val Ser Leu Ala Ile Asp Ala Tyr Pro Leu Thr Lys His Pro Asn
                565                 570                 575

Gln Glu Tyr Ala Asp Val Phe His Leu Tyr Leu Gln Tyr Ile Arg Lys
            580                 585                 590

Leu His Asp Glu Leu Thr Gly His Met Leu Asp Met Tyr Ser Val Met
        595                 600                 605

Leu Thr Asn Asp Asn Thr Ser Arg Tyr Trp Glu Pro Glu Phe Tyr Glu
    610                 615                 620
```

-continued

Ala Met Tyr Thr Pro His Thr Val Leu Gln Ala Val Gly Ala Cys Val
625 630 635 640

Leu Cys Asn Ser Gln Thr Ser Leu Arg Cys Gly Ala Cys Ile Arg Arg
645 650 655

Pro Phe Leu Cys Cys Lys Cys Cys Tyr Asp His Val Ile Ser Thr Ser
660 665 670

His Lys Leu Val Leu Ser Val Asn Pro Tyr Val Cys Asn Ala Pro Gly
675 680 685

Cys Asp Val Thr Asp Val Thr Gln Leu Tyr Leu Gly Gly Met Ser Tyr
690 695 700

Tyr Cys Lys Ser His Lys Pro Pro Ile Ser Phe Pro Leu Cys Ala Asn
705 710 715 720

Gly Gln Val Phe Gly Leu Tyr Lys Asn Thr Cys Val Gly Ser Asp Asn
725 730 735

Val Thr Asp Phe Asn Ala Ile Ala Thr Cys Asp Trp Thr Asn Ala Gly
740 745 750

Asp Tyr Ile Leu Ala Asn Thr Cys Thr Glu Arg Leu Lys Leu Phe Ala
755 760 765

Ala Glu Thr Leu Lys Ala Thr Glu Glu Thr Phe Lys Leu Ser Tyr Gly
770 775 780

Ile Ala Thr Val Arg Glu Val Leu Ser Asp Arg Glu Leu His Leu Ser
785 790 795 800

Trp Glu Val Gly Lys Pro Arg Pro Pro Leu Asn Arg Asn Tyr Val Phe
805 810 815

Thr Gly Tyr Arg Val Thr Lys Asn Ser Lys Val Gln Ile Gly Glu Tyr
820 825 830

Thr Phe Glu Lys Gly Asp Tyr Gly Asp Ala Val Val Tyr Arg Gly Thr
835 840 845

Thr Thr Tyr Lys Leu Asn Val Gly Asp Tyr Phe Val Leu Thr Ser His
850 855 860

Thr Val Met Pro Leu Ser Ala Pro Thr Leu Val Pro Gln Glu His Tyr
865 870 875 880

Val Arg Ile Thr Gly Leu Tyr Pro Thr Leu Asn Ile Ser Asp Glu Phe
885 890 895

Ser Ser Asn Val Ala Asn Tyr Gln Lys Val Gly Met Gln Lys Tyr Ser
900 905 910

Thr Leu Gln Gly Pro Pro Gly Thr Gly Lys Ser His Phe Ala Ile Gly
915 920 925

Leu Ala Leu Tyr Tyr Pro Ser Ala Arg Ile Val Tyr Thr Ala Cys Ser
930 935 940

His Ala Ala Val Asp Ala Leu Cys Glu Lys Ala Leu Lys Tyr Leu Pro
945 950 955 960

Ile Asp Lys Cys Ser Arg Ile Ile Pro Ala Arg Ala Arg Val Glu Cys
965 970 975

Phe Asp Lys Phe Lys Val Asn Ser Thr Leu Glu Gln Tyr Val Phe Cys
980 985 990

Thr Val Asn Ala Leu Pro Glu Thr Thr Ala Asp Ile Val Val Phe Asp
995 1000 1005

Glu Ile Ser Met Ala Thr Asn Tyr Asp Leu Ser Val Val Asn Ala
1010 1015 1020

Arg Leu Arg Ala Lys His Tyr Val Tyr Ile Gly Asp Pro Ala Gln
1025 1030 1035

```
Leu Pro  Ala Pro Arg Thr Leu  Leu Thr Lys Gly Thr  Leu Glu Pro
    1040                 1045                 1050

Glu Tyr  Phe Asn Ser Val Cys  Arg Leu Met Lys Thr  Ile Gly Pro
    1055                 1060                 1065

Asp Met  Phe Leu Gly Thr Cys  Arg Arg Cys Pro Ala  Glu Ile Val
    1070                 1075                 1080

Asp Thr  Val Ser Ala Leu Val  Tyr Asp Asn Lys Leu  Gly Gly Lys
    1085                 1090                 1095

Pro Cys  Ile Lys Val Ala Thr  Val Gln Ser Lys Met  Ser Asp Val
    1100                 1105                 1110

Lys Cys  Thr Ser Val Val Leu  Leu Ser Val Leu Gln  Gln Leu Arg
    1115                 1120                 1125

Val Glu  Ser Ser Ser Lys Leu  Trp Ala Gln Cys Val  Gln Leu His
    1130                 1135                 1140

Asn Asp  Ile Leu Leu Ala Lys  Asp Thr Thr Glu Ala  Phe Glu Lys
    1145                 1150                 1155

Met Val  Ser Leu Val Leu Leu  Ser Met Gln Gly Ala  Val Asp Ile
    1160                 1165                 1170

Asn Lys  Leu Cys Glu Glu Met  Leu Asp Asn Arg Ala  Thr Leu Gln
    1175                 1180                 1185

Ala Ile  Ala Ser Glu Phe Ser  Ser Leu Pro Ser Tyr  Ala Ala Phe
    1190                 1195                 1200

Ala Thr  Ala Gln Glu Ala Tyr  Glu Gln Ala Val Ala  Asn Gly Asp
    1205                 1210                 1215

Ser Glu  Val Val Leu Lys Lys  Leu Lys Lys Ser Leu  Asn Val Ala
    1220                 1225                 1230

Lys Ser  Glu Phe Asp Arg Asp  Ala Ala Met Gln Arg  Lys Leu Glu
    1235                 1240                 1245

Lys Met  Ala Asp Gln Ala Met  Thr Gln Met Tyr Lys  Gln Ala Arg
    1250                 1255                 1260

Ser Glu  Asp Lys Arg Ala Lys  Val Thr Ser Ala Met  Gln Thr Met
    1265                 1270                 1275

Leu Phe  Thr Met Leu Arg Lys  Leu Asp Asn Asp Ala  Leu Asn Asn
    1280                 1285                 1290

Ile Ile  Asn Asn Ala Arg Asp  Gly Cys Val Pro Leu  Asn Ile Ile
    1295                 1300                 1305

Pro Leu  Thr Thr Ala Ala Lys  Leu Met Val Val Ile  Pro Asp Tyr
    1310                 1315                 1320

Asn Thr  Tyr Lys Asn Thr Cys  Asp Gly Thr Thr Phe  Thr Tyr Ala
    1325                 1330                 1335

Ser Ala  Leu Trp Glu Ile Gln  Gln Val Val Asp Ala  Asp Ser Lys
    1340                 1345                 1350

Ile Val  Gln Leu Ser Glu Ile  Ser Met Asp Asn Ser  Pro Asn Leu
    1355                 1360                 1365

Ala Trp  Pro Leu Ile Val Thr  Ala Leu Arg Ala Asn  Ser Ala Val
    1370                 1375                 1380

Lys Leu  Gln Asn Asn Glu Leu  Ser Pro Val Ala Leu  Arg Gln Met
    1385                 1390                 1395

Ser Cys  Ala Ala Gly Thr Thr  Gln Thr Ala Cys Thr  Asp Asp Asn
    1400                 1405                 1410

Ala Leu  Ala Tyr Tyr Asn Thr  Thr Lys Gly Gly Arg  Phe Val Leu
    1415                 1420                 1425

Ala Leu  Leu Ser Asp Leu Gln  Asp Leu Lys Trp Ala  Arg Phe Pro
```

-continued

```
    1430                1435                1440

Lys Ser  Asp Gly Thr Gly Thr  Ile Tyr Thr Glu Leu  Glu Pro Pro
    1445                1450                1455

Cys Arg  Phe Val Thr Asp Thr  Pro Lys Gly Pro Lys  Val Lys Tyr
    1460                1465                1470

Leu Tyr  Phe Ile Lys Gly Leu  Asn Asn Leu Asn Arg  Gly Met Val
    1475                1480                1485

Leu Gly  Ser Leu Ala Ala Thr  Val Arg Leu Gln Ala  Gly Asn Ala
    1490                1495                1500

Thr Glu  Val Pro Ala Asn Ser  Thr Val Leu Ser Phe  Cys Ala Phe
    1505                1510                1515

Ala Val  Asp Ala Ala Lys Ala  Tyr Lys Asp Tyr Leu  Ala Ser Gly
    1520                1525                1530

Gly Gln  Pro Ile Thr Asn Cys  Val Lys Met Leu Cys  Thr His Thr
    1535                1540                1545

Gly Thr  Gly Gln Ala Ile Thr  Val Thr Pro Glu Ala  Asn Met Asp
    1550                1555                1560

Gln Glu  Ser Phe Gly Gly Ala  Ser Cys Cys Leu Tyr  Cys Arg Cys
    1565                1570                1575

His Ile  Asp His Pro Asn Pro  Lys Gly Phe Cys Asp  Leu Lys Gly
    1580                1585                1590

Lys Tyr  Val Gln Ile Pro Thr  Thr Cys Ala Asn Asp  Pro Val Gly
    1595                1600                1605

Phe Thr  Leu Lys Asn Thr Val  Cys Thr Val Cys Gly  Met Trp Lys
    1610                1615                1620

Gly Tyr  Gly Cys Ser Cys Asp  Gln Leu Arg Ile Pro  Asn Pro Leu
    1625                1630                1635

Leu Gly  Leu Asp
    1640
```